US010626161B2

(12) United States Patent
Gardner et al.

(10) Patent No.: US 10,626,161 B2
(45) Date of Patent: Apr. 21, 2020

(54) METHODS AND COMPOSITIONS FOR PROTECTION AGAINST LENTIVIRAL INFECTIONS

(71) Applicants: Matthew Gardner, Jupiter, FL (US); Michael Farzan, Juno Beach, FL (US)

(72) Inventors: Matthew Gardner, Jupiter, FL (US); Michael Farzan, Juno Beach, FL (US)

(73) Assignee: The Scripps Research Institute, La Jolla, CA (US)

( * ) Notice: Subject to any disclaimer, the term of this patent is extended or adjusted under 35 U.S.C. 154(b) by 290 days.

(21) Appl. No.: 15/140,919

(22) Filed: Apr. 28, 2016

(65) Prior Publication Data

US 2016/0340405 A1 Nov. 24, 2016

Related U.S. Application Data

(60) Provisional application No. 62/153,731, filed on Apr. 28, 2015.

(51) Int. Cl.
*C07K 14/73* (2006.01)
*C12N 9/10* (2006.01)
*A61K 38/00* (2006.01)

(52) U.S. Cl.
CPC .......... *C07K 14/70514* (2013.01); *C12N 9/13* (2013.01); *C12Y 208/0202* (2013.01); *A61K 38/00* (2013.01); *C07K 2319/30* (2013.01); *C07K 2319/33* (2013.01)

(58) Field of Classification Search
CPC ................ C07K 14/70514; C12N 9/13; C12Y 208/0202; A61K 38/00
See application file for complete search history.

(56) References Cited

U.S. PATENT DOCUMENTS

| 7,488,481 B2 | 2/2009 | Farzan et al. |
| 2004/0214285 A1* | 10/2004 | Glass ............... C07H 21/04 435/69.3 |
| 2011/0305670 A1 | 12/2011 | Farzan et al. |

OTHER PUBLICATIONS

Chiang, et al., "Enhanced Recognition and Neutralization of HIV-1 by Antibody-Derived CCR5-Mimetic Peptide Variants", *Journal of Virology* 86 (22): 12417-12421 (2012).
Choe, et al., "Tyrosine Sulfation of Human Antibodies Contributes to Recognition of the CCR5 Binding Region of HIV-1 gp 120"; *Cell* 114: 161-170 (2003).
Dorfman, et al., "A Tryosine-sulfated Peptide Detrived from the Heavy-chain CDR3 Region of an HIV-1-neutralizing Antibody Binds gp120 and Inhibits HIV-1 Infection", *Journal of Biological Chemistry* 281 (39): 28529-28535 (2006).
Gardner, et al. 2013 Abstract/Poster.
Gardner, et al., "AAV-expressed eCD-Ig provides durable protection from multile SHIV challenges", *Nature* 519: 87-91 (2015).
Matthew Gardner 2014 Ph.D Thesis.
Kwong, et al., "A Tyrosine-Sulfated CCR5-Mimetic Pepside Promotes Conformational Transistions in the HIV-1 Envelope Glycorotein", *Journal of Virology* 85 (15): 7563-7571 (2011).
Quinlan, et al., "Direct Expression and Validation of Phage-selected Peptide Variants in Mammalian Cells", *Journal of Biological Chemistry* 288 (26): 18803-18810 (2013).
Quinlan, et al., "A Double-Mimetic Peptide Efficiently Neutralized HIV-1 by Bridging the CD4- and Coreceptor-Binding Sites of gp120", *Journal of Virology* 88 (6): 3353-3358 (2014).

* cited by examiner

*Primary Examiner* — Antonio Galisteo Gonzalez

(57) ABSTRACT

The present invention provides methods and compositions for optimally co-expressing in a primate subject a tyrosyl-protein sulfotransferase (TPST) and a lentiviral gp120-binding molecule to provide potent and long term protection against lentiviral infections.

14 Claims, 16 Drawing Sheets

Specification includes a Sequence Listing.

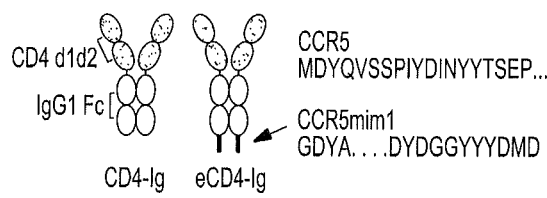
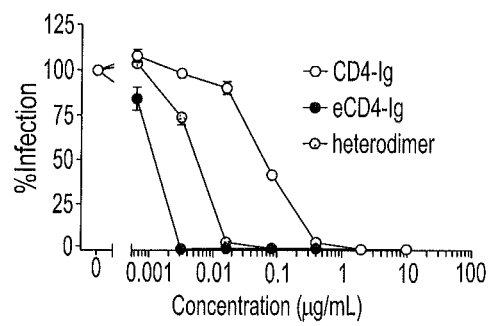
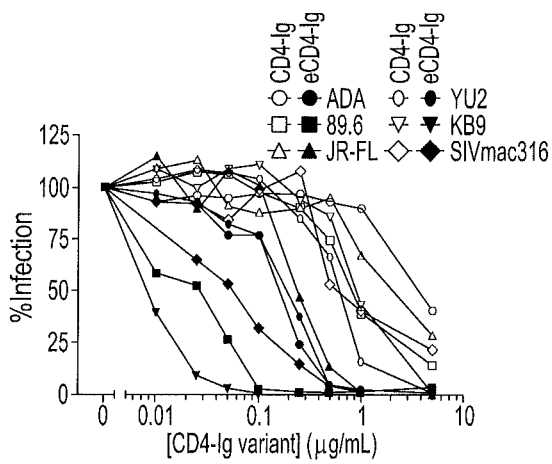
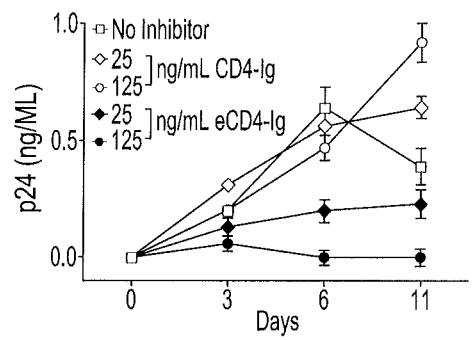
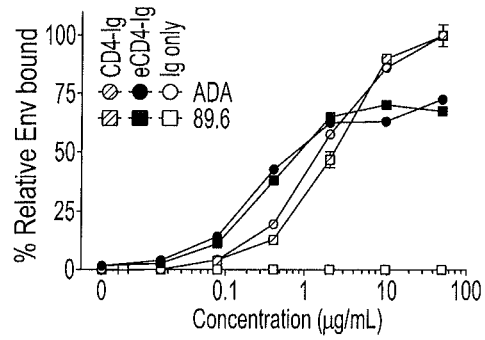
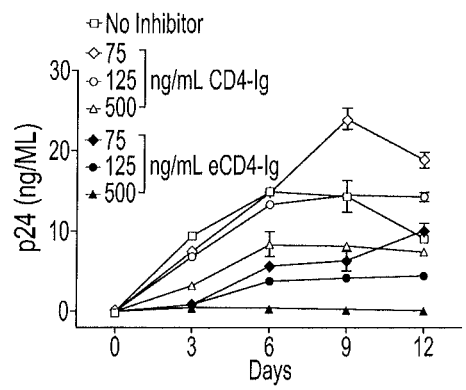
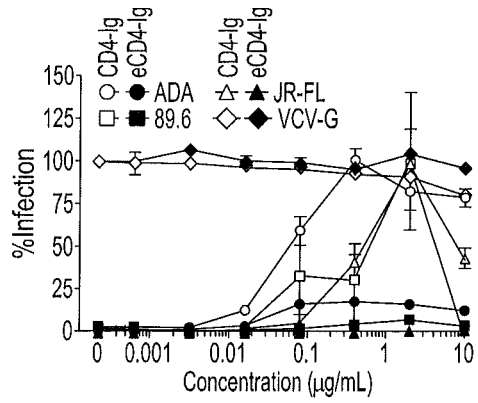
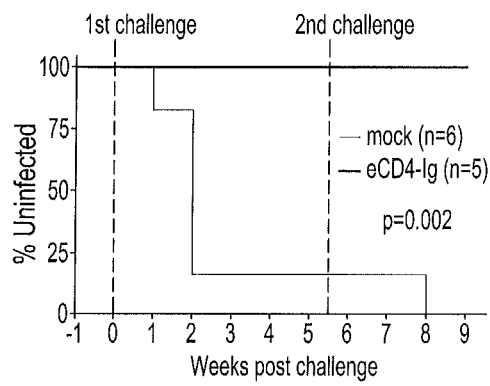

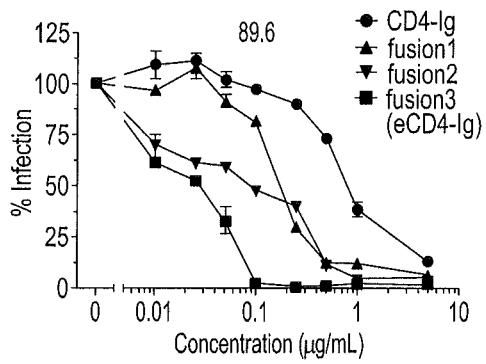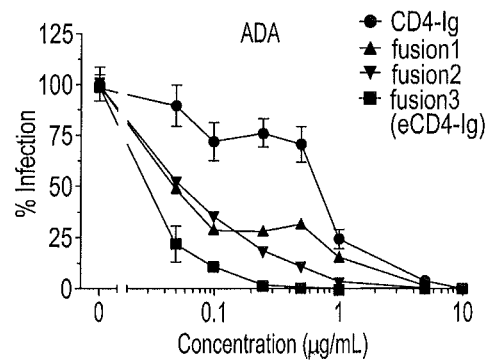
FIG. 5a  FIG. 5b
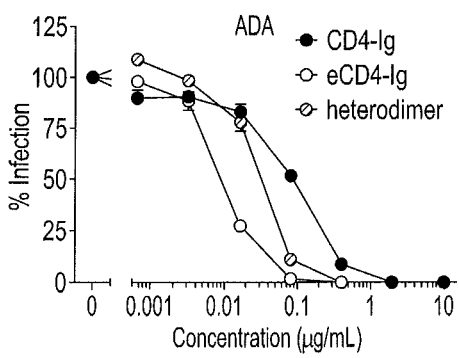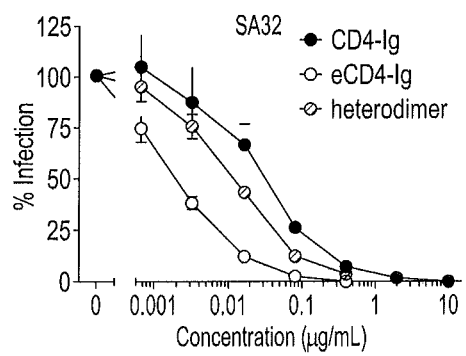
FIG. 5c  FIG. 5d
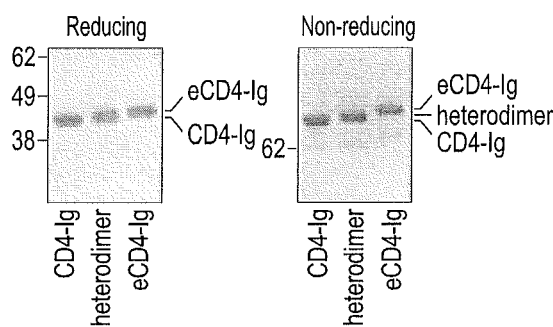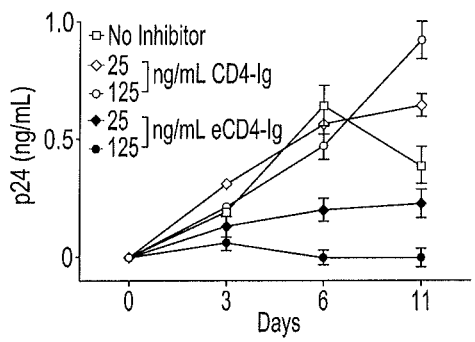
FIG. 5e  FIG. 5f
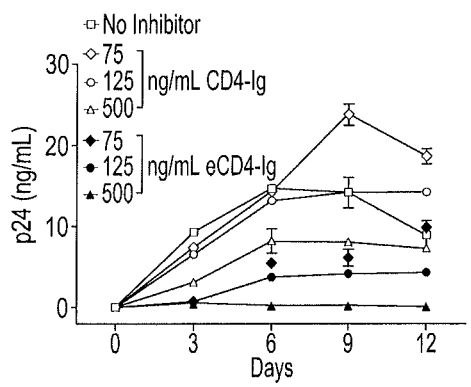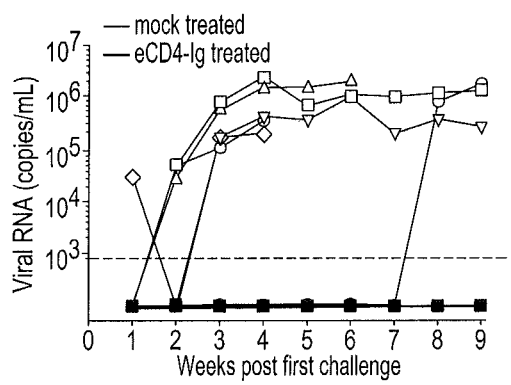
FIG. 5g  FIG. 5h

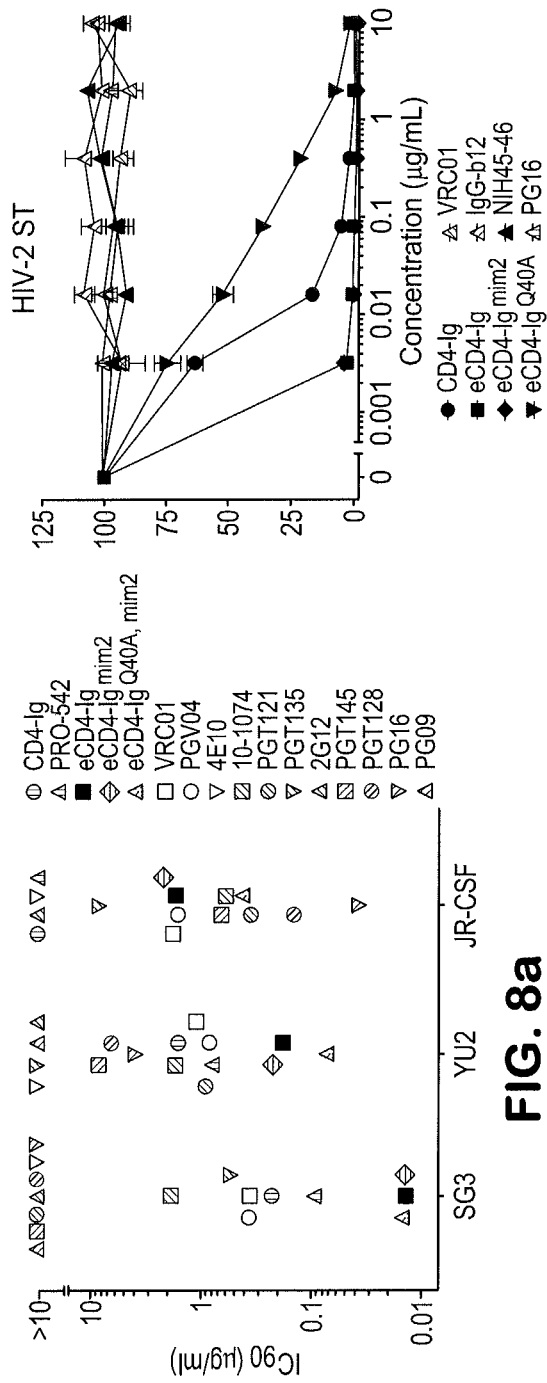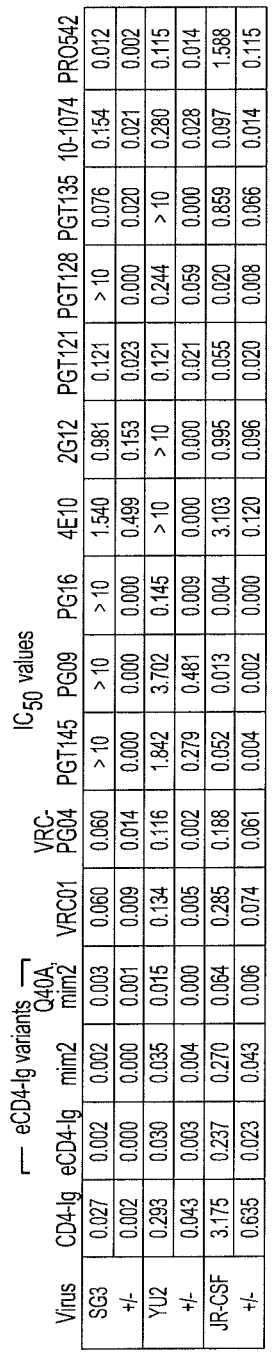
FIG. 8a FIG. 8b FIG. 8c

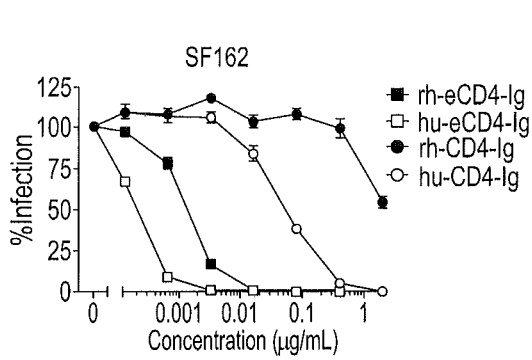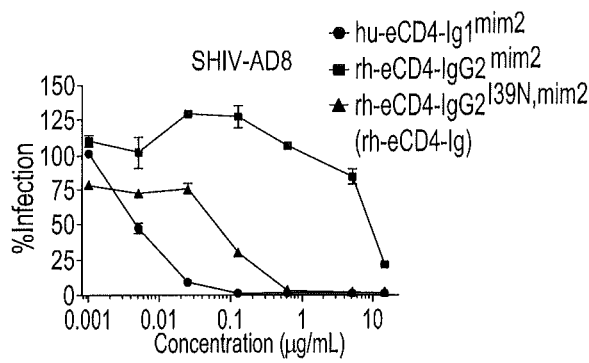
FIG. 10a  FIG. 10b
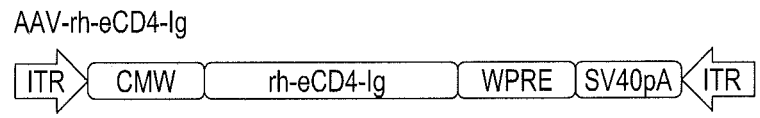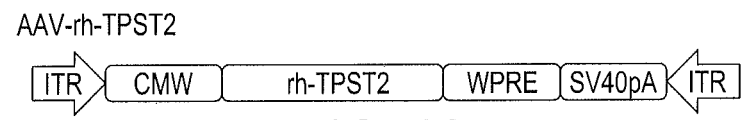
FIG. 10c
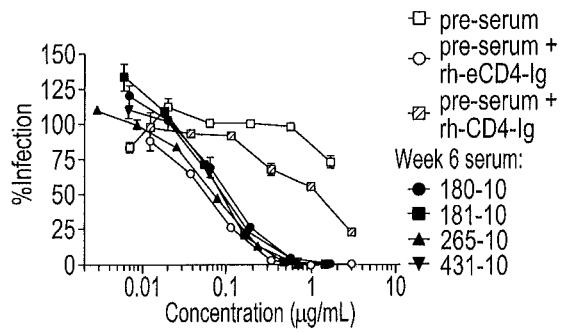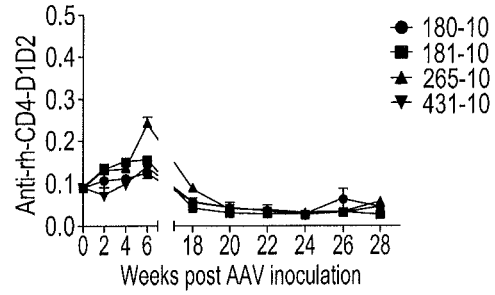
FIG. 10d  FIG. 10e
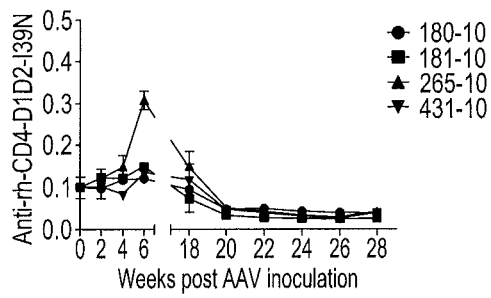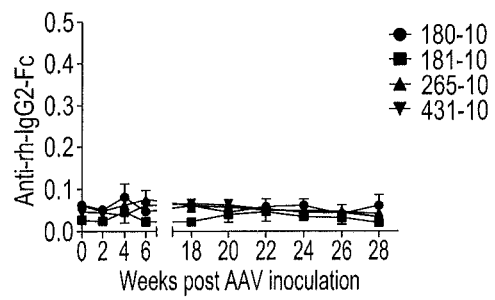
FIG. 10f  FIG. 10g

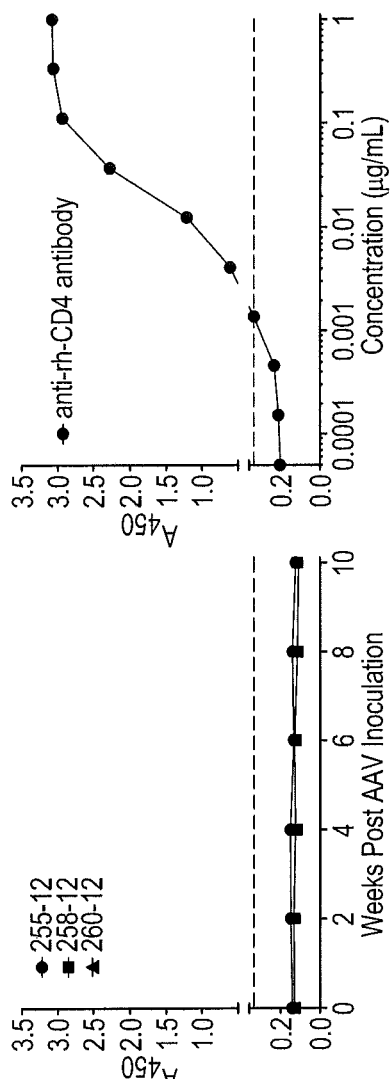
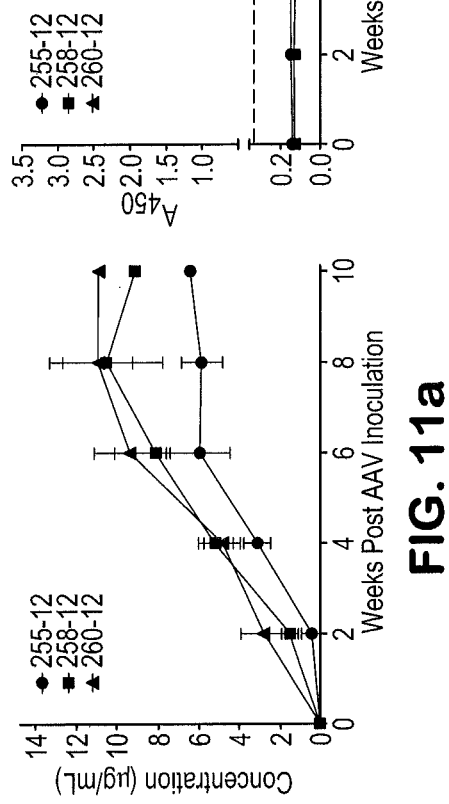
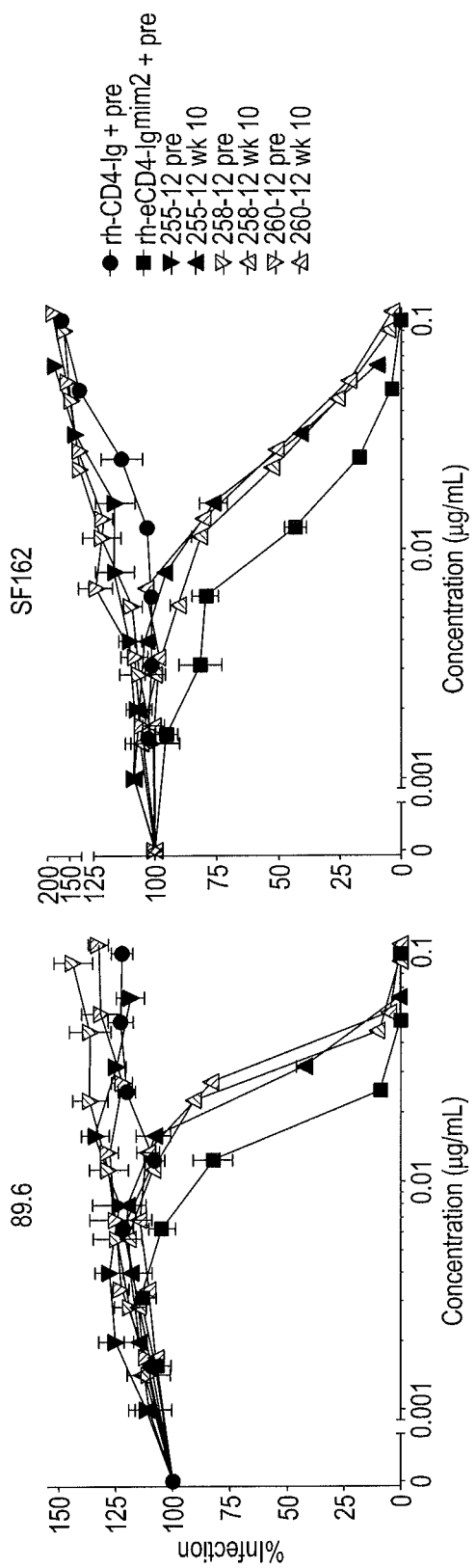
FIG. 11a
FIG. 11b
FIG. 11c
FIG. 11d

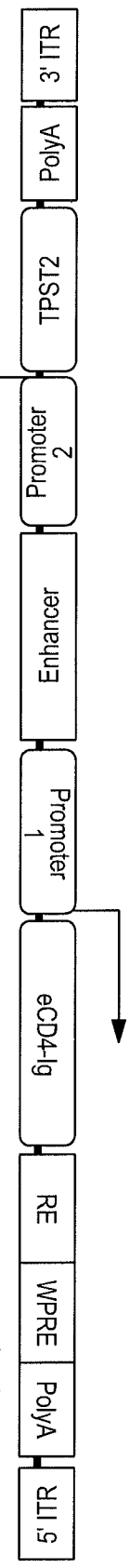
FIG. 12(A) Dual Promoter
FIG. 12(B) Enhancer + Dual Promoter
FIG. 12(C) Promoter + IRES
FIG. 12(D) Bidirectional, Dual Promoter

SEQUENCE LISTING

<160> NUMBER OF SEQ ID NOS: 23

<210> SEQ ID NO 1
<211> LENGTH: 15
<212> TYPE: PRT
<213> ORGANISM: Artificial sequence
<220> FEATURE:
<223> OTHER INFORMATION: Synthetic sequence

<400> SEQUENCE: 1

Gly Asp Tyr Ala Asp Tyr Asp Gly Gly Tyr Tyr Asp Met Asp
1               5                   10                  15

<210> SEQ ID NO 2
<211> LENGTH: 15
<212> TYPE: PRT
<213> ORGANISM: Artificial sequence
<220> FEATURE:
<223> OTHER INFORMATION: Synthetic sequence

<400> SEQUENCE: 2

Gly Asp Tyr Tyr Asp Tyr Asp Gly Gly Tyr Tyr Asp Met Asp
1               5                   10                  15

<210> SEQ ID NO 3
<211> LENGTH: 98
<212> TYPE: PRT
<213> ORGANISM: Homo sapiens

<400> SEQUENCE: 3

Lys Lys Val Val Leu Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
                20                  25                  30

Gln Ile Lys Ile Leu Gly Asn Gln Gly Ser Phe Leu Thr Lys Gly Pro
            35                  40                  45

Ser Lys Leu Asn Asp Arg Ala Asp Ser Arg Arg Ser Leu Trp Asp Gln
        50                  55                  60

Gly Asn Phe Pro Leu Ile Ile Lys Asn Leu Lys Ile Glu Asp Ser Asp
65                  70                  75                  80

Thr Tyr Ile Cys Glu Val Glu Asp Gln Lys Glu Glu Val Gln Leu Leu
                85                  90                  95

Val Phe

<210> SEQ ID NO 4
<211> LENGTH: 178
<212> TYPE: PRT
<213> ORGANISM: Homo sapiens

<400> SEQUENCE: 4

```
Lys Val Val Leu Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
                20              25                  30

Gln Ile Lys Ile Leu Gly Asn Gln Gly Ser Phe Leu Thr Lys Gly Pro
            35              40                  45

Ser Lys Leu Asn Asp Arg Ala Asp Ser Arg Arg Ser Leu Trp Asp Gln
    50                  55                  60

Gly Asn Phe Pro Leu Ile Ile Lys Asn Leu Lys Ile Glu Asp Ser Asp
65                  70                  75                  80

Thr Tyr Ile Cys Glu Val Glu Asp Gln Lys Glu Glu Val Gln Leu Leu
                85                  90                  95

Val Phe Gly Leu Thr Ala Asn Ser Asp Thr His Leu Leu Gln Gly Gln
                100                 105                 110

Ser Leu Thr Leu Thr Leu Glu Ser Pro Pro Gly Ser Ser Pro Ser Val
            115                 120                 125

Gln Cys Arg Ser Pro Arg Gly Lys Asn Ile Gln Gly Gly Lys Thr Leu
130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175

Leu Ala
```

```
<210> SEQ ID NO 5
<211> LENGTH: 232
<212> TYPE: PRT
<213> ORGANISM: Homo sapiens

<400> SEQUENCE: 5
```

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190
```

```
Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 6
<211> LENGTH: 24
<212> TYPE: PRT
<213> ORGANISM: Homo sapiens

<400> SEQUENCE: 6

Met Pro Met Gly Ser Leu Gln Pro Leu Ala Thr Leu Tyr Leu Leu Gly
1               5                   10                  15

Met Leu Val Ala Ser Val Leu Ala
            20

<210> SEQ ID NO 7
<211> LENGTH: 4
<212> TYPE: PRT
<213> ORGANISM: Artificial sequence
<220> FEATURE:
<223> OTHER INFORMATION: Synthetic sequence

<400> SEQUENCE: 7

Ala Ala Asp Pro
1

<210> SEQ ID NO 8
<211> LENGTH: 4
<212> TYPE: PRT
<213> ORGANISM: Artificial sequence
<220> FEATURE:
<223> OTHER INFORMATION: Synthetic sequence

<400> SEQUENCE: 8

Gly Gly Gly Gly
1

<210> SEQ ID NO 9
<211> LENGTH: 457
<212> TYPE: PRT
<213> ORGANISM: Artificial sequence
<220> FEATURE:
<223> OTHER INFORMATION: Synthetic sequence

<400> SEQUENCE: 9

Met Pro Met Gly Ser Leu Gln Pro Leu Ala Thr Leu Tyr Leu Leu Gly
1               5                   10                  15

Met Leu Val Ala Ser Val Leu Ala Gly Asp Tyr Ala Asp Tyr Asp Gly
            20                  25                  30

Gly Tyr Tyr Tyr Asp Met Asp Gly Gly Gly Lys Lys Val Val Leu
        35                  40                  45

Gly Lys Lys Gly Asp Thr Val Glu Leu Thr Cys Thr Ala Ser Gln Lys
    50                  55                  60

Lys Ser Ile Gln Phe His Trp Lys Asn Ser Asn Gln Ile Lys Ile Leu
65                  70                  75                  80

Gly Asn Gln Gly Ser Phe Leu Thr Lys Gly Pro Ser Lys Leu Asn Asp
                85                  90                  95

Arg Ala Asp Ser Arg Arg Ser Leu Trp Asp Gln Gly Asn Phe Pro Leu
```

100                 105                 110
Ile Ile Lys Asn Leu Lys Ile Glu Asp Ser Asp Thr Tyr Ile Cys Glu
            115                 120                 125

Val Glu Asp Gln Lys Glu Val Gln Leu Leu Val Phe Gly Leu Thr
130                 135                 140

Ala Asn Ser Asp Thr His Leu Leu Gln Gly Gln Ser Leu Thr Leu Thr
145                 150                 155                 160

Leu Glu Ser Pro Pro Gly Ser Ser Pro Ser Val Gln Cys Arg Ser Pro
            165                 170                 175

Arg Gly Lys Asn Ile Gln Gly Gly Lys Thr Leu Ser Val Ser Gln Leu
            180                 185                 190

Glu Leu Gln Asp Ser Gly Thr Trp Thr Cys Thr Val Leu Gln Asn Gln
            195                 200                 205

Lys Lys Val Glu Phe Lys Ile Asp Ile Val Val Leu Ala Ala Ala Asp
            210                 215                 220

Pro Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
            245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
            275                 280                 285

Val Asp Gly Val Glu Val His Asn Ala Lys Thr Lys Pro Arg Glu Glu
            290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
            325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
            355                 360                 365

Thr Lys Asn Gln Val Ser Leu Thr Cys Leu Val Lys Gly Phe Tyr Pro
            370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                    405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
            435                 440                 445

Lys Ser Leu Ser Leu Ser Pro Gly Lys
    450                 455

<210> SEQ ID NO 10
<211> LENGTH: 457
<212> TYPE: PRT
<213> ORGANISM: Artificial sequence
<220> FEATURE:
<223> OTHER INFORMATION: Synthetic sequence

<400> SEQUENCE: 10

Met Pro Met Gly Ser Leu Gln Pro Leu Ala Thr Leu Tyr Leu Leu Gly

-continued

```
1               5                   10                  15
Met Leu Val Ala Ser Val Leu Ala Lys Lys Val Leu Gly Lys Lys
                20                  25                  30
Gly Asp Thr Val Glu Leu Thr Cys Thr Ala Ser Gln Lys Lys Ser Ile
                35                  40                  45
Gln Phe His Trp Lys Asn Ser Asn Gln Ile Lys Ile Leu Gly Asn Gln
                50                  55                  60
Gly Ser Phe Leu Thr Lys Gly Pro Ser Lys Leu Asn Asp Arg Ala Asp
65                  70                  75                  80
Ser Arg Arg Ser Leu Trp Asp Gln Gly Asn Phe Pro Leu Ile Ile Lys
                85                  90                  95
Asn Leu Lys Ile Glu Asp Ser Asp Thr Tyr Ile Cys Glu Val Glu Asp
                100                 105                 110
Gln Lys Glu Glu Val Gln Leu Leu Val Phe Gly Leu Thr Ala Asn Ser
                115                 120                 125
Asp Thr His Leu Leu Gln Gly Gln Ser Leu Thr Leu Thr Leu Glu Ser
                130                 135                 140
Pro Pro Gly Ser Ser Pro Ser Val Gln Cys Arg Ser Pro Arg Gly Lys
145                 150                 155                 160
Asn Ile Gln Gly Gly Lys Thr Leu Ser Val Ser Gln Leu Glu Leu Gln
                165                 170                 175
Asp Ser Gly Thr Trp Thr Cys Thr Val Leu Gln Asn Gln Lys Lys Val
                180                 185                 190
Glu Phe Lys Ile Asp Ile Val Val Leu Ala Ala Ala Gly Gly Gly Gly
                195                 200                 205
Gly Asp Tyr Ala Asp Tyr Asp Gly Gly Tyr Tyr Tyr Asp Met Asp Asp
                210                 215                 220
Pro Glu Pro Lys Ser Cys Asp Lys Thr His Thr Cys Pro Pro Cys Pro
225                 230                 235                 240
Ala Pro Glu Leu Leu Gly Gly Pro Ser Val Phe Leu Phe Pro Pro Lys
                245                 250                 255
Pro Lys Asp Thr Leu Met Ile Ser Arg Thr Pro Glu Val Thr Cys Val
                260                 265                 270
Val Val Asp Val Ser His Glu Asp Pro Glu Val Lys Phe Asn Trp Tyr
                275                 280                 285
Val Asp Gly Val Glu Val His Asn Ala Lys Thr Lys Pro Arg Glu Glu
                290                 295                 300
Gln Tyr Asn Ser Thr Tyr Arg Val Val Ser Val Leu Thr Val Leu His
305                 310                 315                 320
Gln Asp Trp Leu Asn Gly Lys Glu Tyr Lys Cys Lys Val Ser Asn Lys
                325                 330                 335
Ala Leu Pro Ala Pro Ile Glu Lys Thr Ile Ser Lys Ala Lys Gly Gln
                340                 345                 350
Pro Arg Glu Pro Gln Val Tyr Thr Leu Pro Pro Ser Arg Asp Glu Leu
                355                 360                 365
Thr Lys Asn Gln Val Ser Leu Thr Cys Leu Val Lys Gly Phe Tyr Pro
                370                 375                 380
Ser Asp Ile Ala Val Glu Trp Glu Ser Asn Gly Gln Pro Glu Asn Asn
385                 390                 395                 400
Tyr Lys Thr Thr Pro Pro Val Leu Asp Ser Asp Gly Ser Phe Phe Leu
                405                 410                 415
Tyr Ser Lys Leu Thr Val Asp Lys Ser Arg Trp Gln Gln Gly Asn Val
                420                 425                 430
```

Phe Ser Cys Ser Val Met His Glu Ala Leu His Asn His Tyr Thr Gln
            435                 440                 445

Lys Ser Leu Ser Leu Ser Pro Gly Lys
    450                 455

<210> SEQ ID NO 11
<211> LENGTH: 457
<212> TYPE: PRT
<213> ORGANISM: Artificial sequence
<220> FEATURE:
<223> OTHER INFORMATION: Synthetic sequence

<400> SEQUENCE: 11

Met Pro Met Gly Ser Leu Gln Pro Leu Ala Thr Leu Tyr Leu Leu Gly
1               5                   10                  15

Met Leu Val Ala Ser Val Leu Ala Lys Lys Val Val Leu Gly Lys Lys
            20                  25                  30

Gly Asp Thr Val Glu Leu Thr Cys Thr Ala Ser Gln Lys Lys Ser Ile
        35                  40                  45

Gln Phe His Trp Lys Asn Ser Asn Gln Ile Lys Ile Leu Gly Asn Gln
    50                  55                  60

Gly Ser Phe Leu Thr Lys Gly Pro Ser Lys Leu Asn Asp Arg Ala Asp
65                  70                  75                  80

Ser Arg Arg Ser Leu Trp Asp Gln Gly Asn Phe Pro Leu Ile Ile Lys
                85                  90                  95

Asn Leu Lys Ile Glu Asp Ser Asp Thr Tyr Ile Cys Glu Val Glu Asp
            100                 105                 110

Gln Lys Glu Glu Val Gln Leu Leu Val Phe Gly Leu Thr Ala Asn Ser
        115                 120                 125

Asp Thr His Leu Leu Gln Gly Gln Ser Leu Thr Leu Thr Leu Glu Ser
    130                 135                 140

Pro Pro Gly Ser Ser Pro Ser Val Gln Cys Arg Ser Pro Arg Gly Lys
145                 150                 155                 160

Asn Ile Gln Gly Gly Lys Thr Leu Ser Val Ser Gln Leu Glu Leu Gln
                165                 170                 175

Asp Ser Gly Thr Trp Thr Cys Thr Val Leu Gln Asn Gln Lys Lys Val
            180                 185                 190

Glu Phe Lys Ile Asp Ile Val Val Leu Ala Ala Ala Asp Pro Glu Pro
        195                 200                 205

Lys Ser Cys Asp Lys Thr His Thr Cys Pro Pro Cys Pro Ala Pro Glu
    210                 215                 220

Leu Leu Gly Gly Pro Ser Val Phe Leu Phe Pro Pro Lys Pro Lys Asp
225                 230                 235                 240

Thr Leu Met Ile Ser Arg Thr Pro Glu Val Thr Cys Val Val Val Asp
                245                 250                 255

Val Ser His Glu Asp Pro Glu Val Lys Phe Asn Trp Tyr Val Asp Gly
            260                 265                 270

Val Glu Val His Asn Ala Lys Thr Lys Pro Arg Glu Glu Gln Tyr Asn
        275                 280                 285

Ser Thr Tyr Arg Val Val Ser Val Leu Thr Val Leu His Gln Asp Trp
    290                 295                 300

Leu Asn Gly Lys Glu Tyr Lys Cys Lys Val Ser Asn Lys Ala Leu Pro
305                 310                 315                 320

Ala Pro Ile Glu Lys Thr Ile Ser Lys Ala Lys Gly Gln Pro Arg Glu
                325                 330                 335

Pro Gln Val Tyr Thr Leu Pro Pro Ser Arg Asp Glu Leu Thr Lys Asn
            340                 345                 350

Gln Val Ser Leu Thr Cys Leu Val Lys Gly Phe Tyr Pro Ser Asp Ile
        355                 360                 365

Ala Val Glu Trp Glu Ser Asn Gly Gln Pro Glu Asn Asn Tyr Lys Thr
    370                 375                 380

Thr Pro Pro Val Leu Asp Ser Asp Gly Ser Phe Phe Leu Tyr Ser Lys
385                 390                 395                 400

Leu Thr Val Asp Lys Ser Arg Trp Gln Gln Gly Asn Val Phe Ser Cys
                405                 410                 415

Ser Val Met His Glu Ala Leu His Asn His Tyr Thr Gln Lys Ser Leu
            420                 425                 430

Ser Leu Ser Pro Gly Lys Gly Gly Gly Gly Asp Tyr Ala Asp Tyr
        435                 440                 445

Asp Gly Gly Tyr Tyr Tyr Asp Met Asp
    450                 455

<210> SEQ ID NO 12
<211> LENGTH: 178
<212> TYPE: PRT
<213> ORGANISM: Artificial sequence
<220> FEATURE:
<223> OTHER INFORMATION: Synthetic sequence

<400> SEQUENCE: 12

Lys Lys Val Val Leu Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Ala Gly Ser Phe Leu Thr Lys Gly Pro
        35                  40                  45

Ser Lys Leu Asn Asp Arg Ala Asp Ser Arg Arg Ser Leu Trp Asp Gln
    50                  55                  60

Gly Asn Phe Pro Leu Ile Ile Lys Asn Leu Lys Ile Glu Asp Ser Asp
65                  70                  75                  80

Thr Tyr Ile Cys Glu Val Glu Asp Gln Lys Glu Glu Val Gln Leu Leu
                85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
        115                 120                 125

Gln Cys Arg Ser Pro Arg Gly Lys Asn Ile Gln Gly Gly Lys Thr Leu
    130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175

Leu Ala

<210> SEQ ID NO 13
<211> LENGTH: 185
<212> TYPE: PRT
<213> ORGANISM: Artificial sequence
<220> FEATURE:
<223> OTHER INFORMATION: Synthetic sequence

<400> SEQUENCE: 13

```
Lys Lys Val Val Leu Gly Lys Gly Asp Thr Val Glu Leu Thr Cys
1               5                   10                  15

Asn Ala Ser Gln Lys Lys Asn Thr Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Ser Asp Arg Ala Asp Ser Arg Lys Ser Leu Trp Asp Gln
50                  55                  60

Gly Cys Phe Ser Met Ile Ile Lys Asn Leu Lys Ile Glu Asp Ser Asp
65                  70                  75                  80

Thr Tyr Ile Cys Glu Val Glu Asn Lys Lys Glu Glu Val Glu Leu Leu
                85                  90                  95

Val Phe Gly Leu Thr Ala Asn Ser Asp Thr His Leu Leu Glu Gly Gln
            100                 105                 110

Ser Leu Thr Leu Thr Leu Glu Ser Pro Pro Gly Ser Ser Pro Ser Val
        115                 120                 125

Lys Cys Arg Ser Pro Gly Gly Lys Asn Ile Gln Gly Gly Arg Thr Ile
130                 135                 140

Ser Val Pro Gln Leu Glu Arg Gln Asp Ser Gly Thr Trp Thr Cys Thr
145                 150                 155                 160

Val Ser Gln Asp Gln Lys Thr Val Glu Phe Lys Ile Asp Ile Val Val
                165                 170                 175

Leu Ala Phe Gln Lys Ala Ser Ser Thr
            180                 185

<210> SEQ ID NO 14
<211> LENGTH: 228
<212> TYPE: PRT
<213> ORGANISM: Rhesus macaque

<400> SEQUENCE: 14

Gly Leu Pro Cys Arg Ser Thr Cys Pro Pro Cys Pro Ala Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

Gln Glu Glu Pro Asp Val Lys Phe Asn Trp Tyr Val Asp Gly Val Glu
50                  55                  60

Val His Asn Ala Gln Thr Lys Pro Arg Glu Glu Gln Phe Asn Ser Thr
65                  70                  75                  80

Tyr Arg Val Val Ser Val Leu Thr Val Thr His Gln Asp Trp Leu Asn
                85                  90                  95

Gly Lys Glu Tyr Thr Cys Lys Val Ser Asn Lys Ala Leu Pro Ala Pro
            100                 105                 110

Arg Gln Lys Thr Val Ser Lys Thr Lys Gly Gln Pro Arg Glu Pro Gln
        115                 120                 125

Val Tyr Thr Leu Pro Pro Arg Glu Glu Leu Thr Lys Asn Gln Val
130                 135                 140

Ser Leu Thr Cys Leu Val Lys Gly Phe Tyr Pro Ser Asp Ile Val Val
145                 150                 155                 160

Glu Trp Ala Ser Asn Gly Gln Pro Glu Asn Thr Tyr Lys Thr Thr Pro
                165                 170                 175

Pro Val Leu Asp Ser Asp Gly Ser Tyr Phe Leu Tyr Ser Lys Leu Thr
```

```
                    180                 185                 190
Val Asp Lys Ser Arg Trp Gln Gln Gly Asn Thr Phe Ser Cys Ser Val
                195                 200                 205

Met His Glu Ala Leu His Asn His Tyr Thr Gln Lys Ser Leu Ser Val
    210                 215                 220

Ser Pro Gly Lys
225

<210> SEQ ID NO 15
<211> LENGTH: 25
<212> TYPE: PRT
<213> ORGANISM: Rhesus macaque

<400> SEQUENCE: 15

Met Asn Arg Gly Ile Pro Phe Arg His Leu Leu Leu Val Leu Gln Leu
1               5                   10                  15

Ala Leu Leu Pro Ala Val Thr Gln Gly
            20                  25

<210> SEQ ID NO 16
<211> LENGTH: 457
<212> TYPE: PRT
<213> ORGANISM: Artificial sequence
<220> FEATURE:
<223> OTHER INFORMATION: Synthetic sequence

<400> SEQUENCE: 16

Met Pro Met Gly Ser Leu Gln Pro Leu Ala Thr Leu Tyr Leu Leu Gly
1               5                   10                  15

Met Leu Val Ala Ser Val Leu Ala Lys Lys Val Val Leu Gly Lys Lys
            20                  25                  30

Gly Asp Thr Val Glu Leu Thr Cys Thr Ala Ser Gln Lys Lys Ser Ile
        35                  40                  45

Gln Phe His Trp Lys Asn Ser Asn Gln Ile Lys Ile Leu Gly Asn Gln
    50                  55                  60

Gly Ser Phe Leu Thr Lys Gly Pro Ser Lys Leu Asn Asp Arg Ala Asp
65                  70                  75                  80

Ser Arg Arg Ser Leu Trp Asp Gln Gly Asn Phe Pro Leu Ile Ile Lys
                85                  90                  95

Asn Leu Lys Ile Glu Asp Ser Asp Thr Tyr Ile Cys Glu Val Glu Asp
            100                 105                 110

Gln Lys Glu Glu Val Gln Leu Leu Val Phe Gly Leu Thr Ala Asn Ser
        115                 120                 125

Asp Thr His Leu Leu Gln Gly Gln Ser Leu Thr Leu Thr Leu Glu Ser
    130                 135                 140

Pro Pro Gly Ser Ser Pro Ser Val Gln Cys Arg Ser Pro Arg Gly Lys
145                 150                 155                 160

Asn Ile Gln Gly Gly Lys Thr Leu Ser Val Ser Gln Leu Glu Leu Gln
                165                 170                 175

Asp Ser Gly Thr Trp Thr Cys Thr Val Leu Gln Asn Gln Lys Lys Val
            180                 185                 190

Glu Phe Lys Ile Asp Ile Val Val Leu Ala Ala Ala Asp Pro Glu Pro
        195                 200                 205

Lys Ser Cys Asp Lys Thr His Thr Cys Pro Pro Cys Pro Ala Pro Glu
    210                 215                 220

Leu Leu Gly Gly Pro Ser Val Phe Leu Phe Pro Pro Lys Pro Lys Asp
225                 230                 235                 240
```

```
Thr Leu Met Ile Ser Arg Thr Pro Glu Val Thr Cys Val Val Val Asp
            245                 250                 255

Val Ser His Glu Asp Pro Glu Val Lys Phe Asn Trp Tyr Val Asp Gly
        260                 265                 270

Val Glu Val His Asn Ala Lys Thr Lys Pro Arg Glu Glu Gln Tyr Asn
    275                 280                 285

Ser Thr Tyr Arg Val Val Ser Val Leu Thr Val Leu His Gln Asp Trp
290                 295                 300

Leu Asn Gly Lys Glu Tyr Lys Cys Lys Val Ser Asn Lys Ala Leu Pro
305                 310                 315                 320

Ala Pro Ile Glu Lys Thr Ile Ser Lys Ala Lys Gly Gln Pro Arg Glu
                325                 330                 335

Pro Gln Val Tyr Thr Leu Pro Pro Ser Arg Asp Glu Leu Thr Lys Asn
            340                 345                 350

Gln Val Ser Leu Thr Cys Leu Val Lys Gly Phe Tyr Pro Ser Asp Ile
        355                 360                 365

Ala Val Glu Trp Glu Ser Asn Gly Gln Pro Glu Asn Asn Tyr Lys Thr
    370                 375                 380

Thr Pro Pro Val Leu Asp Ser Asp Gly Ser Phe Phe Leu Tyr Ser Lys
385                 390                 395                 400

Leu Thr Val Asp Lys Ser Arg Trp Gln Gln Gly Asn Val Phe Ser Cys
                405                 410                 415

Ser Val Met His Glu Ala Leu His Asn His Tyr Thr Gln Lys Ser Leu
            420                 425                 430

Ser Leu Ser Pro Gly Lys Gly Gly Gly Gly Asp Tyr Tyr Asp Tyr
        435                 440                 445

Asp Gly Gly Tyr Tyr Tyr Asp Met Asp
    450                 455

<210> SEQ ID NO 17
<211> LENGTH: 457
<212> TYPE: PRT
<213> ORGANISM: Artificial sequence
<220> FEATURE:
<223> OTHER INFORMATION: Synthetic sequence

<400> SEQUENCE: 17

Met Pro Met Gly Ser Leu Gln Pro Leu Ala Thr Leu Tyr Leu Leu Gly
1               5                   10                  15

Met Leu Val Ala Ser Val Leu Ala Lys Lys Val Val Leu Gly Lys Lys
            20                  25                  30

Gly Asp Thr Val Glu Leu Thr Cys Thr Ala Ser Gln Lys Lys Ser Ile
        35                  40                  45

Gln Phe His Trp Lys Asn Ser Asn Gln Ile Lys Ile Leu Gly Asn Ala
    50                  55                  60

Gly Ser Phe Leu Thr Lys Gly Pro Ser Lys Leu Asn Asp Arg Ala Asp
65                  70                  75                  80

Ser Arg Arg Ser Leu Trp Asp Gln Gly Asn Phe Pro Leu Ile Ile Lys
                85                  90                  95

Asn Leu Lys Ile Glu Asp Ser Asp Thr Tyr Ile Cys Glu Val Glu Asp
            100                 105                 110

Gln Lys Glu Glu Val Gln Leu Leu Val Phe Gly Leu Thr Ala Asn Ser
        115                 120                 125

Asp Thr His Leu Leu Gln Gly Gln Ser Leu Thr Leu Thr Leu Glu Ser
    130                 135                 140
```

```
Pro Pro Gly Ser Ser Pro Ser Val Gln Cys Arg Ser Pro Arg Gly Lys
145                 150                 155                 160

Asn Ile Gln Gly Gly Lys Thr Leu Ser Val Ser Gln Leu Glu Leu Gln
                165                 170                 175

Asp Ser Gly Thr Trp Thr Cys Thr Val Leu Gln Asn Gln Lys Lys Val
            180                 185                 190

Glu Phe Lys Ile Asp Ile Val Val Leu Ala Ala Ala Asp Pro Glu Pro
        195                 200                 205

Lys Ser Cys Asp Lys Thr His Thr Cys Pro Pro Cys Pro Ala Pro Glu
    210                 215                 220

Leu Leu Gly Gly Pro Ser Val Phe Leu Phe Pro Pro Lys Pro Lys Asp
225                 230                 235                 240

Thr Leu Met Ile Ser Arg Thr Pro Glu Val Thr Cys Val Val Val Asp
                245                 250                 255

Val Ser His Glu Asp Pro Glu Val Lys Phe Asn Trp Tyr Val Asp Gly
            260                 265                 270

Val Glu Val His Asn Ala Lys Thr Lys Pro Arg Glu Glu Gln Tyr Asn
        275                 280                 285

Ser Thr Tyr Arg Val Val Ser Val Leu Thr Val Leu His Gln Asp Trp
    290                 295                 300

Leu Asn Gly Lys Glu Tyr Lys Cys Lys Val Ser Asn Lys Ala Leu Pro
305                 310                 315                 320

Ala Pro Ile Glu Lys Thr Ile Ser Lys Ala Lys Gly Gln Pro Arg Glu
                325                 330                 335

Pro Gln Val Tyr Thr Leu Pro Pro Ser Arg Asp Glu Leu Thr Lys Asn
            340                 345                 350

Gln Val Ser Leu Thr Cys Leu Val Lys Gly Phe Tyr Pro Ser Asp Ile
        355                 360                 365

Ala Val Glu Trp Glu Ser Asn Gly Gln Pro Glu Asn Asn Tyr Lys Thr
    370                 375                 380

Thr Pro Pro Val Leu Asp Ser Asp Gly Ser Phe Phe Leu Tyr Ser Lys
385                 390                 395                 400

Leu Thr Val Asp Lys Ser Arg Trp Gln Gln Gly Asn Val Phe Ser Cys
                405                 410                 415

Ser Val Met His Glu Ala Leu His Asn His Tyr Thr Gln Lys Ser Leu
            420                 425                 430

Ser Leu Ser Pro Gly Lys Gly Gly Gly Gly Asp Tyr Ala Asp Tyr
        435                 440                 445

Asp Gly Gly Tyr Tyr Tyr Asp Met Asp
    450                 455

<210> SEQ ID NO 18
<211> LENGTH: 457
<212> TYPE: PRT
<213> ORGANISM: Artificial sequence
<220> FEATURE:
<223> OTHER INFORMATION: Synthetic sequence

<400> SEQUENCE: 18

Met Pro Met Gly Ser Leu Gln Pro Leu Ala Thr Leu Tyr Leu Leu Gly
1               5                   10                  15

Met Leu Val Ala Ser Val Leu Ala Lys Lys Val Val Leu Gly Lys Lys
            20                  25                  30

Gly Asp Thr Val Glu Leu Thr Cys Thr Ala Ser Gln Lys Lys Ser Ile
        35                  40                  45
```

-continued

```
Gln Phe His Trp Lys Asn Ser Asn Gln Ile Lys Ile Leu Gly Asn Ala
 50                  55                  60
Gly Ser Phe Leu Thr Lys Gly Pro Ser Lys Leu Asn Asp Arg Ala Asp
 65                  70                  75                  80
Ser Arg Arg Ser Leu Trp Asp Gln Gly Asn Phe Pro Leu Ile Ile Lys
                 85                  90                  95
Asn Leu Lys Ile Glu Asp Ser Asp Thr Tyr Ile Cys Glu Val Glu Asp
                100                 105                 110
Gln Lys Glu Glu Val Gln Leu Leu Val Phe Gly Leu Thr Ala Asn Ser
                115                 120                 125
Asp Thr His Leu Leu Gln Gly Gln Ser Leu Thr Leu Thr Leu Glu Ser
        130                 135                 140
Pro Pro Gly Ser Ser Pro Ser Val Gln Cys Arg Ser Pro Arg Gly Lys
145                 150                 155                 160
Asn Ile Gln Gly Gly Lys Thr Leu Ser Val Ser Gln Leu Glu Leu Gln
                165                 170                 175
Asp Ser Gly Thr Trp Thr Cys Thr Val Leu Gln Asn Gln Lys Lys Val
                180                 185                 190
Glu Phe Lys Ile Asp Ile Val Val Leu Ala Ala Ala Asp Pro Glu Pro
        195                 200                 205
Lys Ser Cys Asp Lys Thr His Thr Cys Pro Pro Cys Pro Ala Pro Glu
210                 215                 220
Leu Leu Gly Gly Pro Ser Val Phe Leu Phe Pro Pro Lys Pro Lys Asp
225                 230                 235                 240
Thr Leu Met Ile Ser Arg Thr Pro Glu Val Thr Cys Val Val Val Asp
                245                 250                 255
Val Ser His Glu Asp Pro Glu Val Lys Phe Asn Trp Tyr Val Asp Gly
                260                 265                 270
Val Glu Val His Asn Ala Lys Thr Lys Pro Arg Glu Glu Gln Tyr Asn
        275                 280                 285
Ser Thr Tyr Arg Val Val Ser Val Leu Thr Val Leu His Gln Asp Trp
290                 295                 300
Leu Asn Gly Lys Glu Tyr Lys Cys Lys Val Ser Asn Lys Ala Leu Pro
305                 310                 315                 320
Ala Pro Ile Glu Lys Thr Ile Ser Lys Ala Lys Gly Gln Pro Arg Glu
                325                 330                 335
Pro Gln Val Tyr Thr Leu Pro Pro Ser Arg Asp Glu Leu Thr Lys Asn
                340                 345                 350
Gln Val Ser Leu Thr Cys Leu Val Lys Gly Phe Tyr Pro Ser Asp Ile
        355                 360                 365
Ala Val Glu Trp Glu Ser Asn Gly Gln Pro Glu Asn Asn Tyr Lys Thr
370                 375                 380
Thr Pro Pro Val Leu Asp Ser Asp Gly Ser Phe Phe Leu Tyr Ser Lys
385                 390                 395                 400
Leu Thr Val Asp Lys Ser Arg Trp Gln Gln Gly Asn Val Phe Ser Cys
                405                 410                 415
Ser Val Met His Glu Ala Leu His Asn His Tyr Thr Gln Lys Ser Leu
                420                 425                 430
Ser Leu Ser Pro Gly Lys Gly Gly Gly Gly Asp Tyr Tyr Asp Tyr
        435                 440                 445
Asp Gly Gly Tyr Tyr Tyr Asp Met Asp
    450                 455
```

<210> SEQ ID NO 19
<211> LENGTH: 457
<212> TYPE: PRT
<213> ORGANISM: Artificial sequence
<220> FEATURE:
<223> OTHER INFORMATION: Synthetic sequence

<400> SEQUENCE: 19

```
Met Asn Arg Gly Ile Pro Phe Arg His Leu Leu Leu Val Leu Gln Leu
1               5                   10                  15
Ala Leu Leu Pro Ala Val Thr Gln Gly Lys Lys Val Val Leu Gly Lys
                20                  25                  30
Lys Gly Asp Thr Val Glu Leu Thr Cys Asn Ala Ser Gln Lys Lys Asn
            35                  40                  45
Thr Gln Phe His Trp Lys Asn Ser Asn Gln Ile Lys Ile Leu Gly Asn
        50                  55                  60
Gln Gly Ser Phe Leu Thr Lys Gly Pro Ser Lys Leu Ser Asp Arg Ala
65                  70                  75                  80
Asp Ser Arg Lys Ser Leu Trp Asp Gln Gly Cys Phe Ser Met Ile Ile
                85                  90                  95
Lys Asn Leu Lys Ile Glu Asp Ser Asp Thr Tyr Ile Cys Glu Val Glu
            100                 105                 110
Asn Lys Lys Glu Glu Val Glu Leu Leu Val Phe Gly Leu Thr Ala Asn
        115                 120                 125
Ser Asp Thr His Leu Leu Glu Gly Gln Ser Leu Thr Leu Thr Leu Glu
130                 135                 140
Ser Pro Pro Gly Ser Ser Pro Ser Val Lys Cys Arg Ser Pro Gly Gly
145                 150                 155                 160
Lys Asn Ile Gln Gly Gly Arg Thr Ile Ser Val Pro Gln Leu Glu Arg
                165                 170                 175
Gln Asp Ser Gly Thr Trp Thr Cys Thr Val Ser Gln Asp Gln Lys Thr
            180                 185                 190
Val Glu Phe Lys Ile Asp Ile Val Leu Ala Phe Gln Lys Ala Ser
        195                 200                 205
Ser Thr Gly Leu Pro Cys Arg Ser Thr Cys Pro Cys Pro Ala Glu
    210                 215                 220
Leu Leu Gly Gly Pro Ser Val Phe Leu Phe Pro Pro Lys Pro Lys Asp
225                 230                 235                 240
Thr Leu Met Ile Ser Arg Thr Pro Glu Val Thr Cys Val Val Val Asp
                245                 250                 255
Val Ser Gln Glu Glu Pro Asp Val Lys Phe Asn Trp Tyr Val Asp Gly
            260                 265                 270
Val Glu Val His Asn Ala Gln Thr Lys Pro Arg Glu Glu Gln Phe Asn
        275                 280                 285
Ser Thr Tyr Arg Val Val Ser Val Leu Thr Val Thr His Gln Asp Trp
290                 295                 300
Leu Asn Gly Lys Glu Tyr Thr Cys Lys Val Ser Asn Lys Ala Leu Pro
305                 310                 315                 320
Ala Pro Arg Gln Lys Thr Val Ser Lys Thr Lys Gly Gln Pro Arg Glu
                325                 330                 335
Pro Gln Val Tyr Thr Leu Pro Pro Arg Glu Glu Leu Thr Lys Asn
            340                 345                 350
Gln Val Ser Leu Thr Cys Leu Val Lys Gly Phe Tyr Pro Ser Asp Ile
        355                 360                 365
```

Val Val Glu Trp Ala Ser Asn Gly Gln Pro Glu Asn Thr Tyr Lys Thr
    370             375             380

Thr Pro Pro Val Leu Asp Ser Asp Gly Ser Tyr Phe Leu Tyr Ser Lys
385             390             395             400

Leu Thr Val Asp Lys Ser Arg Trp Gln Gln Gly Asn Thr Phe Ser Cys
            405             410             415

Ser Val Met His Glu Ala Leu His Asn His Tyr Thr Gln Lys Ser Leu
            420             425             430

Ser Val Ser Pro Gly Lys Gly Gly Gly Gly Asp Tyr Tyr Asp Tyr
            435             440             445

Asp Gly Gly Tyr Tyr Tyr Asp Met Asp
    450             455

<210> SEQ ID NO 20
<211> LENGTH: 438
<212> TYPE: PRT
<213> ORGANISM: Artificial sequence
<220> FEATURE:
<223> OTHER INFORMATION: Synthetic sequence

<400> SEQUENCE: 20

Met Pro Met Gly Ser Leu Gln Pro Leu Ala Thr Leu Tyr Leu Leu Gly
1               5                   10                  15

Met Leu Val Ala Ser Val Leu Ala Lys Lys Val Val Leu Gly Lys Lys
            20                  25                  30

Gly Asp Thr Val Glu Leu Thr Cys Thr Ala Ser Gln Lys Lys Ser Ile
        35                  40                  45

Gln Phe His Trp Lys Asn Ser Asn Gln Ile Lys Ile Leu Gly Asn Gln
    50                  55                  60

Gly Ser Phe Leu Thr Lys Gly Pro Ser Lys Leu Asn Asp Arg Ala Asp
65                  70                  75                  80

Ser Arg Arg Ser Leu Trp Asp Gln Gly Asn Phe Pro Leu Ile Ile Lys
                85                  90                  95

Asn Leu Lys Ile Glu Asp Ser Asp Thr Tyr Ile Cys Glu Val Glu Asp
            100                 105                 110

Gln Lys Glu Glu Val Gln Leu Leu Val Phe Gly Leu Thr Ala Asn Ser
        115                 120                 125

Asp Thr His Leu Leu Gln Gly Gln Ser Leu Thr Leu Thr Leu Glu Ser
    130                 135                 140

Pro Pro Gly Ser Ser Pro Ser Val Gln Cys Arg Ser Pro Arg Gly Lys
145                 150                 155                 160

Asn Ile Gln Gly Gly Lys Thr Leu Ser Val Ser Gln Leu Glu Leu Gln
                165                 170                 175

Asp Ser Gly Thr Trp Thr Cys Thr Val Leu Gln Asn Gln Lys Lys Val
            180                 185                 190

Glu Phe Lys Ile Asp Ile Val Val Leu Ala Ala Ala Asp Pro Glu Pro
        195                 200                 205

Lys Ser Cys Asp Lys Thr His Thr Cys Pro Pro Cys Pro Ala Pro Glu
    210                 215                 220

Leu Leu Gly Gly Pro Ser Val Phe Leu Phe Pro Pro Lys Pro Lys Asp
225                 230                 235                 240

Thr Leu Met Ile Ser Arg Thr Pro Glu Val Thr Cys Val Val Val Asp
                245                 250                 255

Val Ser His Glu Asp Pro Glu Val Lys Phe Asn Trp Tyr Val Asp Gly
            260                 265                 270

```
Val Glu Val His Asn Ala Lys Thr Lys Pro Arg Glu Gln Tyr Asn
            275                 280                 285

Ser Thr Tyr Arg Val Val Ser Val Leu Thr Val Leu His Gln Asp Trp
    290                 295                 300

Leu Asn Gly Lys Glu Tyr Lys Cys Lys Val Ser Asn Lys Ala Leu Pro
305                 310                 315                 320

Ala Pro Ile Glu Lys Thr Ile Ser Lys Ala Lys Gly Gln Pro Arg Glu
                325                 330                 335

Pro Gln Val Tyr Thr Leu Pro Pro Ser Arg Asp Glu Leu Thr Lys Asn
            340                 345                 350

Gln Val Ser Leu Thr Cys Leu Val Lys Gly Phe Tyr Pro Ser Asp Ile
            355                 360                 365

Ala Val Glu Trp Glu Ser Asn Gly Gln Pro Glu Asn Asn Tyr Lys Thr
370                 375                 380

Thr Pro Pro Val Leu Asp Ser Asp Gly Ser Phe Phe Leu Tyr Ser Lys
385                 390                 395                 400

Leu Thr Val Asp Lys Ser Arg Trp Gln Gln Gly Asn Val Phe Ser Cys
                405                 410                 415

Ser Val Met His Glu Ala Leu His Asn His Tyr Thr Gln Lys Ser Leu
            420                 425                 430

Ser Leu Ser Pro Gly Lys
            435

<210> SEQ ID NO 21
<211> LENGTH: 13
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(3)
<223> OTHER INFORMATION: Each Xaa is independently any amino acid or
      absent.
<220> FEATURE:
<221> NAME/KEY: MISC_FEATURE
<222> LOCATION: (5)..(7)
<223> OTHER INFORMATION: Each Xaa is independently any amino acid or
      absent.
<220> FEATURE:
<221> NAME/KEY: MISC_FEATURE
<222> LOCATION: (8)..(9)
<223> OTHER INFORMATION: Xaa is any amino acid residue.
<220> FEATURE:
<221> NAME/KEY: MISC_FEATURE
<222> LOCATION: (11)..(13)
<223> OTHER INFORMATION: Each Xaa is independently any amino acid or
      absent.

<400> SEQUENCE: 21

Xaa Xaa Xaa Tyr Xaa Xaa Xaa Xaa Xaa Tyr Xaa Xaa Xaa
1               5                   10

<210> SEQ ID NO 22
<211> LENGTH: 12
<212> TYPE: PRT
<213> ORGANISM: Artificial sequence
<220> FEATURE:
<223> OTHER INFORMATION: Synthetic sequence

<400> SEQUENCE: 22

Asp Tyr Tyr Asp Tyr Asp Gly Gly Tyr Tyr Tyr Asp
1               5                   10
```

```
-continued

<210> SEQ ID NO 23
<211> LENGTH: 18
<212> TYPE: PRT
<213> ORGANISM: Homo sapiens

<400> SEQUENCE: 23

Met Asp Tyr Gln Val Ser Ser Pro Tyr Asp Ile Asn Tyr Tyr Thr Ser
1               5                   10                  15

Glu Pro
```

METHODS AND COMPOSITIONS FOR PROTECTION AGAINST LENTIVIRAL INFECTIONS

CROSS-REFERENCE TO RELATED APPLICATIONS

The subject patent application claims the benefit of priority to U.S. Provisional Patent Application No. 62/153,731, filed Apr. 28, 2015 (now pending). The full disclosure of the priority application is incorporated herein by reference in its entirety and for all purposes.

STATEMENT OF GOVERNMENT SUPPORT

This invention was made with government support under AI100263 and AI091476 awarded by the National Institutes of Health. The government has certain rights in this invention.

BACKGROUND OF THE INVENTION

The replicative cycle of lentiviruses such as HIV and SIV begins with the attachment of the virus to susceptible host cells, which is followed by fusion of viral and cellular membranes. These events are mediated by the exterior viral envelope glycoproteins and require the expression of the cellular receptor CD4 and a coreceptor, principally the chemokine receptor CCR5 or CXCR4. The HIV-1 envelope glycoprotein (Env) is a trimeric complex of heterodimers composed of a surface glycoprotein, gp120, and a transmembrane component, gp41. Virus association with CD4 triggers conformational changes in gp120 that promote high-affinity association with the coreceptor and expose helical region 1 (HR1) of gp41. The association of gp120 with CD4 and a coreceptor induces additional conformational changes in which gp41 helical regions 1 and 2 associate, placing viral and cellular membranes in close apposition and thereby promoting lipid mixing and viral fusion.

There have been some progresses in developing effective therapeutics (e.g., vaccines) that can afford protection against HIV infection, e.g., antibody-like immunoadhesins or broadly neutralizing antibodies (bNAbs). However, a large fraction of HIV-1 isolates remain partially or wholly resistant to even the best bNAbs. The immunoadhesin based therapeutics, e.g., CD4-Ig, were shown to neutralize most HIV isolates and irreversibly inactivate Env. However, the affinity of these therapeutics for Env are lower than those of bNAbs, and their potency is further compromised by its parallel ability to promote infection. Further, development of mimetics of the primary HIV-1 coreceptor CCR5 also did not lead to satisfactory HIV therapeutics.

There is a strong and urgent need in the art for more potent therapeutic compositions that can provide more effective and broad protection against infections of primate lentiviruses such as HIV. The present invention addresses this and other unmet needs in the art.

SUMMARY OF THE INVENTION

In one aspect, the invention provides therapeutic compositions that contain (a) a first polynucleotide sequence expressing a tyrosylprotein sulfotransferase (TPST), and (b) a second polynucleotide sequence expressing a binding molecule that, upon tyrosine-sulfation by the TPST, is capable of binding to a gp120 protein of a primate lentivirus or neutralizing infection by the primate lentivirus. In the therapeutic compositions, the molar ratio of the first polynucleotide sequence to the second polynucleotide sequence, or molar ratio of the TPST expressed from the first polynucleotide sequence to the binding molecule expressed from the second polynucleotide sequence, is greater than 1:10. In some embodiments, the first polynucleotide sequence and the second polynucleotide sequence are both DNA sequences. In some embodiments, the first polynucleotide sequence and the second polynucleotide sequence are both RNA sequences. In various embodiments, the first polynucleotide sequence and the second polynucleotide sequence can each be a linear sequence or a circular sequence. In some preferred embodiments, the noted molar ratio is at least about 1:8, 1:6, 1:4, or 1:2.

In some therapeutic compositions, the first polynucleotide sequence and the second polynucleotide sequence are each present in an expression vector. In some other compositions, the first polynucleotide sequence and the second polynucleotide sequence are both present in the same expression vector. For example, the expression vector(s) can be adeno-associated virus (AAV) vectors, adenovirus vectors, retrovirus vectors, lentivirus vectors, or herpesvirus vectors. In some embodiments, the TPST is tyrosylprotein sulfotransferase 2 (TPST2) or enzymatically active fragment thereof. In some embodiments, the binding molecule binds to a coreceptor binding site on the gp120 protein. For example, the binding molecule can contain a sulfopeptide capable of binding to the CCR5-binding site on HIV gp120. Some therapeutic composition of the invention can further contain a binding moiety that is capable of binding to the CD4-binding site on a gp120 protein of a primate lentivirus. In some embodiments, the binding moiety capable of binding to the CD4-binding site on a gp120 protein has an amino acid sequence that is substantially identical to that of domain 1 of the human CD4 protein (CD4 D1) or domains 1 and 2 of the human CD4 protein (CD4 D1D2).

In some therapeutic compositions, the binding molecule can further contain an Fc region of an immunoglobulin. Some of these therapeutic composition contain the sulfopeptide and the Fc binding region that are fused to a CD4 derived polypeptide capable of binding to the CD4-binding site on HIV gp120. In some of these embodiments, the binding molecule contains a fusion polypeptide with an amino acid sequence that is substantially identical to a sequence selected from the group consisting of SEQ ID Nos:9-11 and 16-19. In some of these therapeutic compositions, the binding molecule contains the fusion polypeptide eCD4-Ig which has the amino acid sequence shown in SEQ ID NO:11.

In a related aspect, the invention provides expression systems that contain a polynucleotide sequence expressing a first polypeptide and a second polypeptide at a molar ratio that is greater than 1:10. In these expression systems, the first polypeptide is a tyrosine-protein sulfotransferase (TPST) or an enzymatic fragment thereof, and the second polypeptide is a binding molecule that, upon tyrosine-sulfation by the TPST, is capable of binding to a coreceptor binding site on a gp120 protein of a primate lentivirus or neutralizing infection by the primate lentivirus. In some embodiments, the polynucleotide sequence is a DNA sequence or an RNA sequence encoding the first polypeptide and the second polypeptide. In some embodiments, the polynucleotide sequence is a linear sequence or a circular sequence encoding the first polypeptide and the second polypeptide. In some other embodiments, the polynucleotide sequence is an adeno-associated virus (AAV) vector, an adenovirus vector, a retrovirus vector, a lentivirus vector, or a herpesvirus vector. In some embodiments, the first polypeptide and the second polypeptide are expressed under the control of one promoter sequence. In some other embodiments, the first polypeptide and the second polypeptide are expressed under the control of two separate promoter sequences. In various embodiments, the expression system can further contain one or more expression regulatory elements to control the molar ratio. For example, the regulatory elements can include enhancer elements, introns, internal ribosome entry sites (IRESs), and woodchuck response elements (WPREs).

In some expression systems, the TPST to be expressed is tyrosylprotein sulfotransferase 2 (TPST2) or enzymatically active fragment thereof. In some expression systems, the binding molecule to be expressed contains a sulfopeptide capable of binding to the CCR5-binding site on HIV gp120. In some embodiments, the binding molecule to be expressed further contains an Fc region of an immunoglobulin. In some embodiments, the binding molecule to be expressed contains a sulfopeptide that is fused to a CD4 derived polypeptide capable of binding to the CD4-binding site on HIV gp120. In some expression systems of the invention, the binding molecule to be expressed contains eCD4-Ig (SEQ ID NO:11).

In another aspect, the invention provides methods for preventing or treating a lentiviral viral infection in a subject. The methods entail administering to the subject at risk of developing or suffering from the lentiviral infection a therapeutically or prophylactically effective amount of the therapeutic composition or expression system described herein. Some of the methods are directed to preventing or treating HIV-1 infections in human subjects. In some embodiments, the TPST expressed by the therapeutic composition or expression system is TPST2, and the binding molecule expressed contains eCD4-Ig (SEQ ID NO:11), eCD4-Ig$^{mim2}$ (SEQ ID NO:16), eCD4-Ig$^{Q40A}$ (SEQ ID NO:17), or eCD4-Ig$^{Q40A,mim2}$ (SEQ ID NO:18). Some methods of the invention further entails measuring (1) expression levels of the TPST and the binding molecule in the subject, or (2) sulfation level of the expressed binding molecule in the subject. In some embodiments, the TPST and the binding molecule are expressed at a molar ratio of at least about 1:4. In some methods, the therapeutic composition or expression system is administered to the subject via an intramuscular inoculation.

A further understanding of the nature and advantages of the present invention may be realized by reference to the remaining portions of the specification and claims.

DESCRIPTION OF THE DRAWINGS

FIGS. 1*a*-1*h* show functional characterization of eCD4-Ig. a, CD4-Ig is comprised of CD4 domains 1 and 2 fused to the human IgG1 Fc domain. In eCD4-Ig, the sulfopeptide CCR5mim1 (SEQ ID NO:1) is fused to the carboxyl-terminus of CD4-Ig. The sequence of the CCR5 amino terminus (SEQ ID NO:23) is provided for comparison. CCR5mim1 alanine 4 is substituted with tyrosine in CCR5mim2, described below. b, HIV-1 pseudotyped with the Envs of the indicated HIV-1 or SIV isolates was incubated with GHOST-CCR5 cells and varying concentrations of CD4-Ig or eCD4-Ig. Infection was measured as GFP-expression by flow cytometry. c, 293T cells transfected to express 89.6 or ADA Envs were incubated with the indicated concentrations of CD4-Ig, eCD4-Ig, or IgG and analyzed by flow cytometry. d, HIV-1 expressing luciferase and pseudotyped with the Envs of the indicated isolates was incubated with Cf2Th-CCR5 cells in the presence of varying concentrations of CD4-Ig or eCD4-Ig. Experiment was controlled with HIV-1 pseudotyped with the VSV-G protein. Infection normalized to the maximum value observed for each pseudovirus. e, HIV-1 pseudotyped with the 89.6 Env was incubated with TZM-bl cells and varying concentration of CD4-Ig, eCD4-Ig, or a CD4-Ig/eCD4-Ig heterodimer. Similar experiments using additional Envs are presented in FIGS. 5*c* and 5*d*. f, Infection curves of humanized NSG mice with 2-4 mg/ml of serum eCD4-Ig at time of HIV-$1_{NL4-3}$ challenges (n=5), or mock treated (n=6) are shown. Three uninfected eCD4-Ig treated mice and the sole uninfected mock treated mouse were rechallenged 5 weeks post-first challenge. Significant protection (p=0.002; Mantel-Cox test) was observed in the eCD4-Ig treated group. Viral load measurements are shown in FIG. 5*h*.

FIGS. 2*a*-2*c* show comparison of eCD4-Ig variants and HIV-1 neutralizing antibodies. a, HIV-1 pseudotyped with the Envs of the indicated isolates were incubated with TZM-bl cells and varying concentrations of the indicated entry inhibitors, and the resulting $IC_{50}$ values are plotted. $IC_{90}$ values and standard errors are presented in FIGS. 8*a* and 8*b*). b, Experiments similar to those in (a) except that HIV-1 pseudotyped with the SIVmac239 Env was incubated with varying concentrations of CD4-Ig, eCD4-Ig variants, or CD4bs antibodies. FIG. 8*c* shows a similar study using the HIV-2 ST Env. c, ADCC activity was assessed using CEM.NKR-CCR5 target cells infected four days earlier with HIV-1 NL4-3, SIVmac239, or $SHIV_{KB9}$. Cells were then incubated with KHYG-1 NK effector cells for 8 hours in the presence of the indicated inhibitors. ADCC activity was measured as loss of luciferase activity from the target cells.

FIGS. 3*a*-3*b* show summary of HIV-1, HIV-2 and SIV neutralization studies. The $IC_{50}$ values from studies of FIGS. 1*b*, 2*a*, 2*b*, and FIGS. 6*a*-8*c* are plotted. The number of isolates resistant to 50 μg/ml of the indicated inhibitors are indicated at top of figure. Geometric means are calculated for neutralized isolates and indicated with horizontal lines. Note that these data include 38 HIV-1 isolates selected for resistance to NIH45-46 or 3BNC117, so that isolates resistant to these antibodies are over-represented. Nonetheless, the geometric mean values of neutralized viruses are consistent with previous reports (Diskin et al., Science 334, 1289-1293, 2011; Huang et al., Nature 491, 406-412, 2012; Walker et al., Nature 477, 466-470, 2011; and Scheid et al., Science 333, 1633-1637, 2011). Data for VRC01 and 3BNC117 were reported in Huang et al. (supra) and Scheid et al. (supra). $IC_{80}$ values are presented in FIG. 9.

FIGS. 4*a*-4*h* show that AAV-rh-eCD4-Ig protects rhesus macaques from SHIV-AD8. a, Infection analysis comparing four male Indian-origin rhesus macaques inoculated intramuscularly with $2\times10^{13}$ AAV particles delivering rh-eCD4-Ig and four age- and gender-matched controls. At 8, 11, 16, 20, 26, and 34 weeks post-inoculation, macaques were challenged with the indicated p27 titers of SHIV-AD8. Significant protection (p=0.006; Mantel-Cox test) was observed in the AAV-rh-eCD4-Ig treated group. b, Viral loads of inoculated and control macaques are shown, with the time and titer of challenge indicated above the graph. c, Concentrations of rh-eCD4-Ig in the sera of inoculated macaques were measured by ELISA through week 40 post-inoculation. d, The neutralizing potency of macaque sera obtained 4 weeks post-AAV-inoculation was compared to pre-inoculation sera (pre-sera), and pre-sera mixed with laboratory produced rh-eCD4-Ig, as in FIG. 2*b*. e, Anti-transgene antibody responses in AAV-rh-eCD4-Ig inoculated macaques were compared to those in macaques inoculated with AAV expressing the indicated bNAbs bearing constant regions of rhesus IgG2. Sera from four weeks post-inoculation were analyzed. Plates were coated with equivalent amounts of rh-eCD4-Ig or rhesus forms of bNAbs and incubated with sera and anti-rhesus lambda chain (left panel) or -kappa chain (right panel) antibody conjugated to horseradish peroxidase. Note that 3BNC117 and NIH45-46 bear a kappa light chain, whereas PGT121 and 10-1074 bear a lambda light chain, so that only host antibody responses were detected. Values indicate absorbance at 450 nM. P-values (Student's 2-tailed t test) are indicated above the figures. f, The sensitivity of the assay in (e) was increased to measure longitudinally the anti-rh-eCD4-Ig activity in the sera of inoculated macaques. Both anti-kappa and anti-lamda secondary antibodies were used. Values are scaled for comparison to values in (e). g, h, The same assay as in (f) except that responses to rh-CD4-Ig, lacking CCR5mim2 (g) or to CCR5mim2 fused to a human IgG1 Fc domain (h) were measured.

FIGS. 5a-5h provide additional data for the studies shown in FIGS. 1a and 1b. Experiments similar to those of FIG. 1b except that CD4-Ig, fusion1, fusion2, and fusion3 (eCD4-Ig) are compared using HIV-1 pseudotyped with the envelope glycoproteins of the 89.6 (a) or ADA (b) isolates. c, d, Experiments similar to those in FIG. 1e except that CD4-Ig, eCD4-Ig, or heterodimers thereof are compared. e, CD4-Ig, eCD4-Ig, and the CD4-Ig/eCD4-Ig heterodimer assayed in FIGS. 1e, 5c and 5d were analyzed by SDS-PAGE and stained with Coomassie blue under reducing (left) and non-reducing (right) conditions. f, g, Infectious 89.6 (f) or SG3 (g) HIV-1 was incubated with human PBMC in the presence of the indicated concentrations of CD4-Ig or eCD4-Ig, or without either inhibitor. Culture supernatants were collected on the indicated day and viral p24 levels were measured by ELISA. h, Viral loads in RNA copies/mL are shown for each humanized mouse of FIG. 1f. Mice treated with eCD4-Ig are indicated with blue lines and mice treated with PBS are indicated with red lines. The 800 copies/mL limit of detection of this assay is indicated by a dashed line.

FIGS. 6a-6b show $IC_{50}$ values of eCD4-Ig variants against neutralization-resistant isolates. a, The $IC_{50}$ values (µg/mL) of CD4-Ig, eCD4-Ig, eCD4-Ig$^{mim2}$ (mim2), eCD4-Ig$^{Q40A}$ (Q40A), and eCD4-Ig$^{Q40A,mim2}$ (Q40A,mim2) against 24 HIV-1 and SIV isolates selected for their neutralization resistance are shown. The clade and tier of each isolate is listed. HIV-1 pseudotyped with the indicted envelope glycoprotein was incubated in triplicate with TZM-bl cells and varying concentrations of CD4-Ig or eCD4-Ig variant. Luciferase activity was determined two days post-infection. 'Fold' indicates the ratio of the $IC_{50}$ value of CD4-Ig to the geometric mean of the $IC_{50}$ values of the assayed eCD4-Ig variants. The geometric mean of eCD4-Ig variants and the CD4bs antibodies 3BCN117, NIH45-46, and VRC01 calculated from values reported in Huang et al. (supra) and Scheid et al. (supra) are shown in the two rightmost columns. b, Neutralization studies similar to those in (a) except that the $IC_{50}$ values of CD4-Ig, eCD4-Ig$^{mim2}$ (mim2), eCD4-Ig$^{Q40A,mim2}$ (Q40A,mim2) and NIH45-46 were determined for a panel of 40 viral isolates selected for their resistance to the CD4bs bNAbs 3BNC117 and NIH45-46. $IC_{50}$ values of the CD4bs antibodies VRC01 and 3BNC117 listed in the two rightmost columns were reported in Huang et al. (supra) and Scheid et al. (supra).

FIGS. 7a-7b show $IC_{80}$ (µg/mL) values of eCD4-Ig variants against neutralization-resistant isolates.

FIGS. 8a-8c provide additional data for the studies shown in FIGS. 2a-2c. a, $IC_{90}$ values for the same experiments shown in FIG. 2a, presented in the same format. b, Numeric $IC_{50}$ and $IC_{90}$ values of the experiment shown in (a) and FIG. 2a are shown. Standard errors are indicated below their $IC_{50}$ and $IC_{90}$ values. c, Experiments similar to those in FIG. 2b except that HIV-1 pseudotyped with the Env of the HIV-2 isolate ST were incubated with the indicated concentrations of CD4-Ig, eCD4-Ig variants, or the CD4bs antibodies IgG-b12, VRC01, or NIH45-46.

FIG. 9 provides additional data for the studies shown in FIGS. 3a-3b ($IC_{80}$ values). The $IC_{80}$ values from studies of FIGS. 1b, 2a, 2b, and FIGS. 6a-8c are plotted. The number of isolates resistant to 50 µg/ml of the indicated inhibitors are indicated on top. Geometric means are calculated for neutralized isolates and indicated with horizontal lines.

FIGS. 10a-10g provide additional data for the studies shown FIGS. 4a-4h. a, An experiment similar to that in FIG. 2b, except that rhesus and human CD4-Ig and eCD4-Ig are compared for their ability to neutralize HIV-1 pseudotyped with the SF162 envelope glycoprotein. All variants have wild-type rhesus or human CD4 domains. Note that variants bearing rhesus CD4 are markedly less potent at neutralizing HIV-1. b, Experiment similar to FIG. 2b and to (a) except that human eCD4-Ig$^{mim2}$ and its rhesus analog bearing or not the I39N mutation are compared using SHIV-AD8. Note that the I39N mutation largely restores the neutralization activity of rhesus eCD4-Ig$^{mim2}$. c, A representation of the AAV vectors used in the non-human primate studies of FIGS. 4a-4h. Rh-eCD4-Ig (rh-eCD4-IgG2$^{I39N,mim2}$) and rhesus tyrosine protein sulfotransferase 2 (TPST2; green) were introduced into a single-stranded AAV vector downstream of a CMV promoter. A woodchuck response element (WPRE), used to promote expression, and the SV40 polyadenylation signal (SV40 pA) were also included. AAV inverted terminal repeats (ITR) are indicated in grey arrows. d, An experiment similar to that in FIG. 4d except that sera from week 6 were analyzed. e, f, g, Experiments similar to those in FIGS. 4f-4h except that the reactivity of rhesus sera was examined for a construct bearing wild-type rhesus CD4 domains 1 and 2 fused to the human IgG1 Fc domain (e), one bearing rhesus CD4 domains 1 and 2 with the I39N mutation, again fused to the human IgG1 Fc domain (f), or the antibody NIH45-46 fused to the rhesus IgG2 constant regions, used here to present the rhesus IgG2 Fc domain (g).

FIGS. 11a-11d show characterization of rh-eCD4-Igmim2 in rhesus macaques. (A) Sera titers of rh-eCD4-Igmim2 from animals 255-12, 258-12, and 260-12 at the indicated weeks post AAV inoculations were measured by ELISA with immobilized SIV gp120. (B) Anti-transgene response measured by ELISA with immobilized rh-eCD4-Igmim2 using sera samples from the indicated weeks post scAAV inoculation. Dotted line indicates limit of detection as determined by an anti-rhesus CD4 antibody. All titers were below this limit equivalent to 0.0014 µg/ml of an anti-rhesus CD4 antibody. (C) A standard curve used to determine limit of detection of the anti-rhesus CD4-Ig antibody in panel b. Limit of detection is again represented with a dotted line. (D) HIV-1 pseudotyped with 89.6 or SF162 envelope glycoproteins was pre-incubated with sera samples obtained 2 weeks before ('pre') or 10 weeks ('wk 10') after scAAV inoculation, or with preinoculation sera spiked in vitro with purified rh-CD4-Ig or rh-eCD4-Igmim2 to a concentration of 10 µg/mL, based on the ELISA measurements of panel A.

FIGS. 12(A)-12(D) are a schematic illustration of various structural designs of a vector for co-expressing eCD4-Ig and TPST2.

DETAILED DESCRIPTION

I. Overview

Figure 2A:
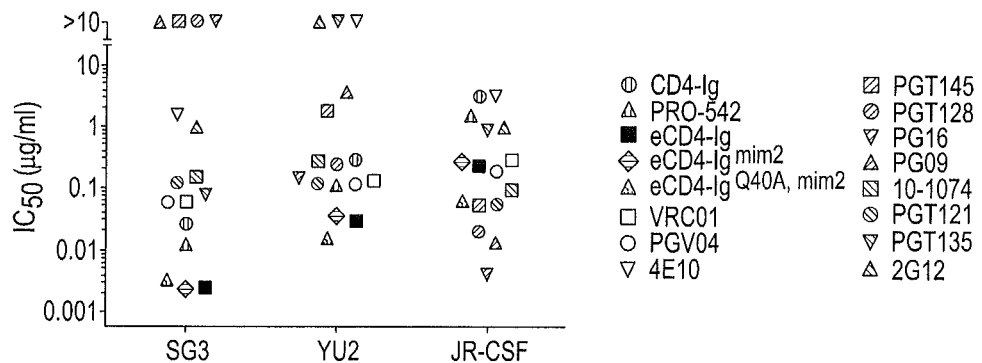

Entry into host cells by lentiviruses such as HIV-1 and SIV is mediated by its envelope glycoprotein (Env) and requires cellular expression of CD4 and a coreceptor, principally CCR5 or CXCR4. High-affinity binding of the viral envelope glycoprotein to the coreceptor CCR5 requires sulfation of the amino-terminal tyrosines of CCR5. The present invention is predicated in part on the discovery by the present inventors that endogenous tyrosylprotein sulfotransferase activity in primate muscle tissue is insufficient for the production of sulfopeptides that can bind the coreceptor-binding site of lentiviral gp120 proteins, and that an optimal ratio of in vivo overexpression of exogenously introduced tyrosylprotein sulfotransferase (TPST) and a coreceptor-binding moiety is required to provide a broad and potent HIV entry inhibition. Specifically, it is known that eCD4-Ig, a fusion of CD4-Ig with a small CCR5-mimetic sulfopeptide, binds avidly and cooperatively to the HIV-1 envelope glycoprotein (Env). However, it represents a significant challenge to maintain an optimal sulfation of the CCR5-mimetic peptide in vivo and a long term HIV-inhibiting activity of the fusion molecule in a subject. Importantly, the inventors identified that in vivo activities of eCD4-Ig to inhibit HIV entry requires an optimal level of co-expression of a tyrosylprotein sulfotransferase (TPST2) which modifies the CCR5 mimetic. As exemplified herein (e.g., Example 3 below), when the eCD4-Ig fusion and TPST2 were separately expressed from adeno-associated virus (AAV) vectors, optimal in vivo HIV-inhibiting activities of eCD4-Ig can be achieved when vectors expressing TPST2 and vectors expressing the eCD4-Ig fusion are administered at a molar ratio of at least 1:8 or higher (e.g., 1:4). It was found that coadministration of an eCD4-Ig expressing vector and a TPST2 expressing vector at the optimal ratio protected all inoculated macaques from multiple infectious doses that are likely higher than those present in most human transmission events. Furthermore, similar therapeutic activities were observed when both eCD4-Ig and TPST2 were expressed from the same expressing vector at the optimal ratio. These studies indicate that the therapeutic compositions of the invention could provide effective, long-term, and near universal protection against infections by primate lentiviruses such as human HIV-1.

In accordance with these discoveries, the invention provides therapeutic compositions and methods for preventing and treating lentiviral infections. Unless otherwise specified herein, the therapeutic compositions of the invention, the encoding polynucleotides, expression vectors and host cells, as well as the related therapeutic methods, can all be generated or performed in accordance with the procedures exemplified herein or routinely practiced methods well known in the art. See, e.g., Methods in Enzymology, Volume 289: Solid-Phase Peptide Synthesis, J. N. Abelson, M. I. Simon, G. B. Fields (Editors), Academic Press; 1st edition (1997) (ISBN-13: 978-0121821906); U.S. Pat. Nos. 4,965, 343, and 5,849,954; Sambrook et al., Molecular Cloning: A Laboratory Manual, Cold Spring Harbor Press, N.Y., (3$^{rd}$ ed., 2000); Brent et al., Current Protocols in Molecular Biology, John Wiley & Sons, Inc. (ringbou ed., 2003); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl Eds., Academic Press Inc., San Diego, USA (1987); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998). The following sections provide additional guidance for practicing the compositions and methods of the present invention.

II. Definitions

Unless defined otherwise, all technical and scientific terms used herein have the same meaning as commonly understood by those of ordinary skill in the art to which this invention pertains. The following references provide one of skill with a general definition of many of the terms used in this invention: *Academic Press Dictionary of Science and Technology*, Morris (Ed.), Academic Press (1$^{st}$ ed., 1992); *Oxford Dictionary of Biochemistry and Molecular Biology*, Smith et al. (Eds.), Oxford University Press (revised ed., 2000); *Encyclopaedic Dictionary of Chemistry*, Kumar (Ed.), Anmol Publications Pvt. Ltd. (2002); *Dictionary of Microbiology and Molecular Biology*, Singleton et al. (Eds.), John Wiley & Sons (3$^{rd}$ ed., 2002); *Dictionary of Chemistry*, Hunt (Ed.), Routledge (1$^{st}$ ed., 1999); *Dictionary of Pharmaceutical Medicine*, Nahler (Ed.), Springer-Verlag Telos (1994); *Dictionary of Organic Chemistry*, Kumar and Anandand (Eds.), Anmol Publications Pvt. Ltd. (2002); and *A Dictionary of Biology* (*Oxford Paperback Reference*), Martin and Hine (Eds.), Oxford University Press (4$^{th}$ ed., 2000). Further clarifications of some of these terms as they apply specifically to this invention are provided herein.

As used herein, the singular forms "a," "an," and "the," refer to both the singular as well as plural, unless the context clearly indicates otherwise. For example, "an Env-derived trimer" can refer to both single or plural Env-derived trimer molecules, and can be considered equivalent to the phrase "at least one Env-derived trimer."

As used herein, the terms "antigen" or "immunogen" are used interchangeably to refer to a substance, typically a protein, which is capable of inducing an immune response in a subject. The term also refers to proteins that are immunologically active in the sense that once administered to a subject (either directly or by administering to the subject a nucleotide sequence or vector that encodes the protein) is able to evoke an immune response of the humoral and/or cellular type directed against that protein.

Conservative amino acid substitutions providing functionally similar amino acids are well known in the art. The following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); Arginine (R), Lysine (K); 5) Isoleucine (I), Leucine (L), Methionine (M), Valine (V); and 6) Phenylalanine (F), Tyrosine (Y), Tryptophan (W). Not all residue positions within a protein will tolerate an otherwise "conservative" substitution. For instance, if an amino acid residue is essential for a function of the protein, even an otherwise conservative substitution may disrupt that activity, for example the specific binding of an antibody to a target epitope may be disrupted by a conservative mutation in the target epitope.

In the practice of the invention, conservative amino acid substitutions, e.g., substituting one acidic or basic amino acid for another, can often be made without affecting the biological activity of a peptide or protein described herein (e.g., CCR5-mimetic peptide, TPST, Fc-binding region). Minor variations in sequence of this nature may be made in any of the peptides disclosed herein, provided that these changes do not substantially reduce (e.g., by 15% or more) the ability of the peptide or fusion polypeptide to neutralize the entry of a lentivirus into its host cells.

Entry of primate lentiviruses such as HIV-1 into host cells requires its envelope glycoprotein binding cooperatively to the primary cellular receptor CD4 and a coreceptor. At least fourteen chemokine receptors or structurally related molecules have been identified that can function as coreceptors for entry of HIV-1 in vitro. See, e.g., van Rij et al., Community Genetics 5:88-101, 2002; De Roda Husman et al., Trends Microbiol. 6:244-249, 1998; and Berger et al., Ann. Rev. Immunol. 17:657-700, 1999. The coreceptors most often utilized by the viruses are CXCR4 or CCR5. Many HIV-1 variants utilize CCR5 as the coreceptor (e.g., R5 isolates), during viral transmission and throughout most of the asymptomatic phase of infection. In many cases, with the decline in immune function, variants emerge that utilize coreceptors in addition to CCR5, in particular CXCR4. Some of these variants (e.g., R5X4 isolates) utilize both CXCR4 or CCR5 as the coreceptor.

Epitope refers to an antigenic determinant. These are particular chemical groups or peptide sequences on a molecule that are antigenic, such that they elicit a specific immune response, for example, an epitope is the region of an antigen to which B and/or T cells respond. Epitopes can be formed both from contiguous amino acids or noncontiguous amino acids juxtaposed by tertiary folding of a protein.

Effective amount of a vaccine or other agent that is sufficient to generate a desired response, such as reduce or eliminate a sign or symptom of a condition or disease, such as AIDS. For instance, this can be the amount necessary to inhibit viral replication or to measurably alter outward symptoms of the viral infection, such as increase of T cell counts in the case of an HIV-1 infection. In general, this amount will be sufficient to measurably inhibit virus (for example, HIV-1) replication or infectivity. When administered to a subject, a dosage will generally be used that will achieve target tissue concentrations (for example, in lymphocytes) that has been shown to achieve in vitro inhibition of viral replication. In some examples, an "effective amount" is one that treats (including prophylaxis) one or more symptoms and/or underlying causes of any of a disorder or disease, for example to treat HIV-1. In one example, an effective amount is a therapeutically effective amount. In one example, an effective amount is an amount that prevents one or more signs or symptoms of a particular disease or condition from developing, such as one or more signs or symptoms associated with AIDS.

As used herein, a fusion protein is a recombinant protein containing amino acid sequence from at least two unrelated proteins that have been joined together, via a peptide bond, to make a single protein. The unrelated amino acid sequences can be joined directly to each other or they can be joined using a linker sequence. As used herein, proteins are unrelated, if their amino acid sequences are not normally found joined together via a peptide bond in their natural environment(s) (e.g., inside a cell). For example, the amino acid sequences of a CCR5 mimetic peptide, and the amino acid sequences of a CD4 polypeptide are not normally found joined together via a peptide bond.

As used herein, "gene delivery" refers to the introduction of an exogenous polynucleotide into a cell for gene transfer, and may encompass targeting, binding, uptake, transport, localization, replicon integration and expression. "Gene transfer" refers to the introduction of an exogenous polynucleotide into a cell which may encompass targeting, binding, uptake, transport, localization and replicon integration, but is distinct from and does not imply subsequent expression of the gene.

As used herein, "gene expression" or "expression" refers to the process of gene transcription, translation, and post-translational modification.

HIV-1 envelope protein (Env) is initially synthesized as a longer precursor protein of 845-870 amino acids in size, designated gp160. gp160 forms a homotrimer and undergoes glycosylation within the Golgi apparatus. In vivo, gp160 glycoprotein is endo-proteolytically processed to the mature envelope glycoproteins gp120 and gp41, which are noncovalently associated with each other in a complex on the surface of the virus. The gp120 surface protein contains the high affinity binding site for human CD4, the primary receptor for HIV, as well as domains that interact with fusion coreceptors, such as the chemokine receptors CCR5 and CXCR4. The gp41 protein spans the viral membrane and contains at its amino-terminus a sequence of amino acids important for the fusion of viral and cellular membranes. The native, fusion-competent form of the HIV-1 envelope glycoprotein complex is a trimeric structure composed of three gp120 and three gp41 subunits. The receptor-binding (CD4 and co-receptor) sites are located in the gp120 moieties, whereas the fusion peptides are located in the gp41 components. Exemplary sequence of wildtype gp160 polypeptides are shown in GenBank, e.g., under accession numbers AAB05604 and AAD12142.

gp120 is a subunit and the outer layer of the envelope glycoprotein protein (Env) of the Human Immunodeficiency Virus (HIV). gp120 contains most of the external, surface-exposed, domains of the HIV envelope glycoprotein complex, and it is gp120 which binds both to cellular CD4 receptors and to cellular chemokine receptors (such as CCR5). The mature gp120 wildtype polypeptides have about 500 amino acids in the primary sequence. gp120 is heavily N-glycosylated giving rise to an apparent molecular weight of 120 kD. The polypeptide is comprised of five conserved regions (C1-05) and five regions of high variability (V1-V5). In its tertiary structure, the gp120 glycoprotein is comprised of three major structural domains (the outer domain, the inner domain, and the bridging sheet) plus the variable loops. See, e.g., Wyatt et al., Nature 393, 705-711, 1998; and Kwong et al., Nature 393, 649-59, 1998. The inner domain is believed to interact with the gp41 envelope glycoprotein, while the outer domain is exposed on the assembled envelope glycoprotein trimer.

Lentivirus is a genus of viruses of the Retroviridae family, characterized by a long incubation period. Lentiviruses can deliver a significant amount of viral RNA into the DNA of the host cell and have the unique ability among retroviruses of being able to infect non-dividing cells, so they are one of the most efficient methods of a gene delivery vector. HIV, SIV, FIV, EIAV, and Visna are all examples of lentiviruses. Five serogroups of lentiviruses are recognized, reflecting the vertebrate hosts with which they are associated (primates, sheep and goats, horses, cats, and cattle). Primate lentiviruses include HIV-1 and HIV-2 which infect human and SIVs which include a large group of related but genetically distinct viruses that are found naturally in many African primate species. Primate lentiviruses are distinguished by the use of CD4 protein as a receptor and the absence of dUTPase.

Sequence identity or similarity between two or more nucleic acid sequences, or two or more amino acid sequences, is expressed in terms of the identity or similarity between the sequences. Sequence identity can be measured in terms of percentage identity; the higher the percentage, the more identical the sequences are. Homologs or orthologs of nucleic acid or amino acid sequences usually possess a relatively high degree of sequence identity/similarity when aligned using standard methods. A "substantially identical" nucleic acid or amino acid sequence refers to a polynucleotide or amino acid sequence which comprises a sequence that has at least 75%, 80% or 90% sequence identity to a reference sequence as measured by one of the well-known programs described herein (e.g., BLAST) using standard parameters. The sequence identity is preferably at least 95%, more preferably at least 98%, and most preferably at least 99%. In some embodiments, the subject sequence is of about the same length as compared to the reference sequence, i.e., consisting of about the same number of contiguous amino acid residues (for polypeptide sequences) or nucleotide residues (for polynucleotide sequences).

Sequence identity can be readily determined with various methods known in the art. For example, the BLAST program can be readily employed to align two polynucleotide sequences or two polypeptide sequences and to quickly determine the degree of identity between the two sequences. See, e.g., Henikoff & Henikoff, Proc. Natl. Acad. Sci. USA 89:10915, 1989; Altschul et al., Nucleic Acids Res. 25:3389-402, 1997; and Ye et al., Nucleic Acids Res. 34(Web Server issue): W6-9, 2006. Also suitable for the invention are other methods of alignment of sequences for comparison are well known in the art. Various programs and alignment algorithms are described in: Smith & Waterman, Adv. Appl. Math. 2:482, 1981; Needleman & Wunsch, J. Mol. Biol. 48:443, 1970; Pearson & Lipman, Proc. Natl. Acad. Sci. USA 85:2444, 1988; Higgins & Sharp, Gene, 73:237-44, 1988; Higgins & Sharp, CABIOS 5:151-3, 1989; Corpet et al., Nuc. Acids Res. 16:10881-90, 1988; Huang et al. Computer Appls. in the Biosciences 8, 155-65, 1992; and Pearson et al., Meth. Mol. Bio. 24:307-31, 1994. Altschul et al. (J. Mol. Biol. 215:403-10, 1990) also provided a detailed consideration of sequence alignment methods and homology calculations.

The term "subject" refers to any animal classified as a mammal, e.g., human and non-human mammals. Examples of non-human animals include dogs, cats, cattle, horses, sheep, pigs, goats, rabbits, and etc. Unless otherwise noted, the terms "patient" or "subject" are used herein interchangeably. In some preferred embodiments, the subject amenable for therapeutic applications of the invention is a primate, e.g., human and non-human primates.

As used herein, administration of a polynucleotide or vector into a host cell or a subject refers to introduction into the cell or the subject via any routinely practiced methods. This includes "transduction," "transfection," "transformation" or "transducing" as well known in the art. These terms all refer to standard processes for the introduction of an exogenous polynucleotide, e.g., a transgene in rAAV vector, into a host cell leading to expression of the polynucleotide, e.g., the transgene in the cell, and includes the use of recombinant virus to introduce the exogenous polynucleotide to the host cell. Transduction, transfection or transformation of a polynucleotide in a cell may be determined by methods well known to the art including, but not limited to, protein expression (including steady state levels), e.g., by ELISA, flow cytometry and Western blot, measurement of DNA and RNA by heterologousization assays, e.g., Northern blots, Southern blots and gel shift mobility assays. Methods used for the introduction of the exogenous polynucleotide include well-known techniques such as viral infection or transfection, lipofection, transformation and electroporation, as well as other non-viral gene delivery techniques. The introduced polynucleotide may be stably or transiently maintained in the host cell.

Transcriptional regulatory sequences of use in the present invention generally include at least one transcriptional promoter and may also include one or more enhancers and/or terminators of transcription. Operably linked" refers to an arrangement of two or more components, wherein the components so described are in a relationship permitting them to function in a coordinated manner. By way of illustration, a transcriptional regulatory sequence or a promoter is operably linked to a coding sequence if the TRS or promoter promotes transcription of the coding sequence. An operably linked TRS is generally joined in c/s with the coding sequence, but it is not necessarily directly adjacent to it.

The term "treating" or "alleviating" includes the administration of compounds or agents to a subject to prevent or delay the onset of the symptoms, complications, or biochemical indicia of a disease (e.g., an HIV infection), alleviating the symptoms or arresting or inhibiting further development of the disease, condition, or disorder. Subjects in need of treatment include those already suffering from the disease or disorder as well as those being at risk of developing the disorder. Treatment may be prophylactic (to prevent or delay the onset of the disease, or to prevent the manifestation of clinical or subclinical symptoms thereof) or therapeutic suppression or alleviation of symptoms after the manifestation of the disease.

Tyrosylprotein sulfotransferase (TPST) is the enzyme that catalyzes the sulfation reaction of protein tyrosines, a post-translational modification of proteins. It utilizes 3'-Phosphoadenosine-5'-phosphosulfate (PAPS) as the sulfonate donor and binds proteins with target tyrosine residues to eventually form the tyrosine 0-sulfate ester group and the desulfonated 3'-phosphoadenosine-5'-phosphate (PAP). TPST and tyrosine sulfation is involved in a large number of biological and physiological processes, including viral cell entrance, inflammatory processes and other cell-cell and protein-protein interactions. For example, an important substrate for TPST is CC-chemokine Receptor 5 (CCR5), which plays an important role as the co-receptor protein for the viral entrance of HIV into cells. TPST is about 50-54 kD in size, and has two confirmed isoforms in mammals, TPST1 and TPST2, that are 370 and 377 residues in length, respectively. The two isoforms share an approximately 63% of amino acid identity, and have some differences in their substrate specificities.

A "vector" is a nucleic acid with or without a carrier that can be introduced into a cell. Vectors capable of directing the expression of genes encoding for one or more polypeptides are referred to as "expression vectors". Examples of vectors suitable for the invention include, e.g., viral vectors, plasmid vectors, liposomes and other gene delivery vehicles.

As used herein, "AAV" is adeno-associated virus, and may be used to refer to the naturally occurring wild-type virus itself or derivatives thereof. The term covers all subtypes, serotypes and pseudotypes, and both naturally occurring and recombinant forms, except where required otherwise. As used herein, the term "serotype" refers to an AAV which is identified by and distinguished from other AAVs based on capsid protein reactivity with defined antisera, e.g., serotypes including AAV-1 to AAV-8. For example, serotype AAV-2 is used to refer to an AAV which contains capsid proteins encoded from the cap gene of AAV-2 and a genome containing 5' and 3' ITR sequences from the same AAV-2 serotype. Pseudotyped AAV refers to an AAV that contains capsid proteins from one serotype and a viral genome including 5'-3' ITRs of a second serotype. Pseudotyped rAAV would be expected to have cell surface binding properties of the capsid serotype and genetic properties consistent with the TPS serotype. The abbreviation "rAAV" refers to recombinant adeno-associated viral particle or a recombinant AAV vector (or "rAAV vector"). An "AAV virus" or "AAV viral particle" refers to a viral particle composed of at least one AAV capsid protein (preferably by all of the capsid proteins of a wild-type AAV) and an encapsidated polynucleotide. If the particle comprises a heterologous polynucleotide (i.e., a polynucleotide other than a wild-type AAV genome such as a transgene to be delivered to a mammalian cell), it is typically referred to as "rAAV".

III. Binding Molecules Recognizing Lentiviral Envelope Protein

The invention provides therapeutic compositions that optimally co-express a tyrosylprotein sulfotransferase (TPST) and a binding molecule (also termed "gp120-binding molecule" herein) that specifically binds to a lentiviral gp120 envelope protein. Upon expression, the TPST is capable of tyrosine sulfating the binding molecule. The optimal coexpression, or coexpression under optimal conditions, allows the TPST and the binding molecule to be expressed at an optimal ratio or cellular levels that enable the binding molecule to be optimally sulfated and fully functional. When measured by molar ratio, optimally coexpression requires that the TPST and the binding molecule to be at a ratio that is greater than 1:10. In various embodiments, the TPST and the binding molecule are co-expressed at a molar ratio that is at least about 1:8, 1:7.5, 1:7, 1:6.5, 1:6, 1:5.5, 1:5, 1:4.5, 1:4, 1:3.5, 1:3, 1:2.5, 1:2, 1:1.5, 1:1, or higher. In some exemplary compositions, the two molecules are expressed at a molar ratio of at least about 1:8, 1:6, 1:4, or 1:2. In some other embodiments, the above-described optimal ratio refers to a ratio between the copies of two polynucleotide sequences (e.g., vectors or mRNAs) respectively encoding the TPST and the binding molecule.

In the practice of the invention, the binding molecule can be a single intact entity on which the sulfation site (e.g., tyrosine residues) and the gp120-binding site are both present. Alternatively, the binding molecule can comprise two or more components or moieties that separately harbor the sites for tyrosine-sulfation and for gp120-binding. In some of these embodiments, the different components, e.g., peptides or polynucleotide chains, can be conjugated covalently or noncovalently upon their expressions. In some other embodiments, the different components are not physically conjugated or are loosely associated after being expressed from the encoding polynucleotide sequences (e.g., expression vectors) described herein. For example, the binding molecule can contain multiple distinct polypeptide chains (e.g., immunoglobulin heavy chains and a light chains) of which one chain contains the sulfation sites but requires one or more of the other polypeptide chains in order to bind to the gp120 glycoprotein.

In some embodiments, the binding molecule recognizes the coreceptor binding site on the gp120 glycoprotein. In these embodiments, the binding molecule can be any compound that specifically binds to the coreceptor-binding site on the viral envelope protein. Using HIV-1 as an example, the binding molecule recognizes the coreceptor CCR5- or CXCR4-binding site on the viral gp120. Examples of such binding molecules include broadly neutralizing antibodies (e.g., the well-characterized antibodies E51, 412d, PG9, and PG16), or fragments or peptides derived from these broadly neutralizing antibodies. The binding molecules suitable for the invention include the peptides or fusion polypeptides specifically exemplified herein (e.g., SEQ ID NOs:1, 2, 9-11, and 16-19) and variants with substantially identical sequences. They also include many of the gp120-binding molecules well known in the art. See, e.g., Quinlan et al., J. Virol. 88: 3353-3358, 2014; Kwong et al., J. Virol. 85:7563-7571, 2011; Dorfman et al., J. Biol. Chem. 281:28529-28535, 2006; Farzan et al., J. Biol. Chem. 28:28, 2002; Choe et al., Cell 114:161-170, 2003; Pejchal et al., Proc. Natl. Acad. Sci. U.S.A 107:11483-11488, 2000; Walker et al., Science 326:285-289, 2009; and Rizzuto et al., Science 280:1949-1953, 1998.

The ectodomains of CCR5 and CXCR4 consist of an amino-terminus and three extracellular loops held in position by seven transmembrane helices. There is an acidic, tyrosine-rich sequence within the amino termini of the coreceptors, and tyrosine sulfation of the amino termini facilitates entry of the viruses (e.g., HIV-1) into host cells. In addition, a number of antibodies which bind the coreceptor-binding site of gp120 contain sulfated tyrosines in their CDRH3 regions. Sulfated peptides based on the amino terminus of CCR5, or on the CDRH3 loops of sulfated antibodies, can specifically bind the HIV-1 envelope glycoprotein and inhibit HIV-1 entry. Antibody-derived sulfopeptides retain an arrangement of sulfotyrosines similar to that of the amino terminus of CCR5 and bind a broad range of R5, X4, and dual-tropic envelope glycoproteins. Thus, the binding molecules used in the invention contain the corresponding tyrosine residues that can be sulfated by a tyrosylprotein sulfotransferase. In some embodiments, the binding molecule specifically binds to the CCR5-binding site on the viral gp120 envelope protein. For example, it can be a tyrosine-containing peptide derived from the amino terminus of CCR5. The binding molecule can also be a peptide or mimetic derived from the tyrosine-containing CDRH3 loops of broadly neutralizing antibodies for HIV-1.

In some preferred embodiments, the binding molecule used in the invention contains a sulfopeptide or CCR5 mimetic (also termed "CCR5-mimetic peptide" herein) that binds to the coreceptor-binding site on a lentiviral gp120 protein. These peptides or mimetic peptides bind to the lentiviral gp120 protein by mimicking the coreceptor CCR5. Unless otherwise noted, the CCR5-mimetic peptides or mimetics of the invention include any molecules or peptide sequences that can compete with the natural coreceptor CCR5 for binding to the viral gp120 protein. Examples of such peptides or mimetics are well known in the art. See, e.g., WO2011156747. In some embodiments, the CCR5-mimetic peptide has or harbors an amino acid sequence of XXXYXXXZZYXXX (SEQ ID NO:21). In this sequence, each X residue is independently any amino acid or absent, each Y is a tyrosine capable of being sulfated by a TPST enzyme, and each Z is any amino acid. In addition, two or more of the amino acid residues X or Z in the sequence are independently glutamate or aspartate. In some of these embodiments, three or more of the amino acid residues X or Z in the sequence are independently glutamate or aspartate. In some embodiments, the CCR5-mimetic peptides comprises an amino acid sequence substantially identical to DYYDYDGGYYYD (SEQ ID NO:22). Some specific CCR5-mimetic peptides that can be used in the invention include GDYADYDGGYYYDMD (SEQ ID NO:1) and any of the related peptides described herein or known in the art, e.g., GDYYDYDGGYYYDMD (SEQ ID NO:2).

In some preferred embodiments, the invention can employ peptide mimetic CCR5mim1 or a related sequence in the construction of the binding molecule. CCR5mim1 (SEQ ID NO:1) is a 15-amino acid sulfopeptide that binds to HIV gp120 and is derived from the HIV-1 neutralizing antibody E51. It binds Env with higher affinity than other CCR5-mimetic peptides. See, e.g., Kwong et al., J. Virol. 85:7563-7571, 2011; and Quinlan et al., J. Virol. 88: 3353-3358, 2014. Due to the conservation of the sulfotyrosine-binding pockets of Env, CCR5mim1 can bind to both CCR5- and CXCR4-dependent Envs from all HIV-1 clades. In some other embodiments, the binding molecule of the invention contains a peptide mimetic that is derived from CCR5mim1, CCR5mim2. This variant of CCR5mim1 differs from CCR5mim1 by single alanine to tyrosine substitution22. As described herein, this variant peptide functions similarly to or better than CCR5mim1 in neutralizing various HIV-1 isolates. Suitable for the invention also include other variants that are derived from these peptides, as well as peptides or mimetics that have a substantially identical sequence to these exemplified peptides or variants.

It is known that binding of CCR5-mimetic peptides to HIV-1 gp120 is substantially improved in the presence of CD4 or a CD4-derived polypeptide. In some embodiments of the invention, the binding molecule additionally contains a domain, sequence element or binding moiety that is capable of binding to the binding site on a primate lentiviral gp120 protein for its primary host cell receptor, CD4. As a result, the binding molecule binds to both the coreceptor-binding site and the CD4-binding site on the viral gp120 glycoprotein. Such dual target binding molecules can better neutralize viral infectivity by the cooperative binding to sites on viral gp120 for both the primary receptor CD4 and the coreceptor. For example, some of the dual target binding molecules of the invention contain a CCR5-mimetic peptide for binding to the coreceptor-binding site, and also a CD4 (or CD4-derived) polypeptide (or "domain", "fragment") (e.g., CD4 domain 1 and/or 2) for binding to the CD4-binding site on the viral envelope protein. Some CD4 polypeptides or domains have been tested in clinical trials for neutralizing HIV infections. See, e.g., McDougal et al., Curr. Opin. Immunol., 3:552, 1991; and Pincus, Antiviral Res., 33: 1, 1996. These inhibitors have been tested at high doses, up to 20-25 mg/kg (Jacobson et al., Antimicrob. Agents Chemother., 48:423, 2004). These studies demonstrated that soluble forms of CD4 can be introduced into humans without adverse consequences.

Various forms of CD4 derived polypeptides can be used to construct the dual target binding molecules of the invention. For example, the binding moiety can be a CD4 polypeptide domain that is recognized by the CD4-binding site of the viral gp120 protein, including human CD4 D1 (SEQ ID NO:3) or CD4 D1D2 (SEQ ID NO:4) exemplified herein. In addition, derivatives and fragments of the exemplified CD4 polypeptides, as well as orthologs or variant polypeptides with substantially identical amino acid sequences, can all be used in the invention. Examples of such variants or derivatives include SEQ ID Nos:12 and 13.

One issue associated with using short soluble CD4 molecules as in vivo therapeutic is that sCD4 has a short serum half-life. To address this issue, the sCD4 molecule can be fused to a larger molecule or carrier. For example, as exemplified herein, the first two domains of CD4 can be fused to the immunoglobulin (IgG) Fc-domain. This fusion confers on CD4 the ability to interact with the neonatal Fc receptor, to rescue antibodies from lysosomal degradation of protein absorbed into cells (He et al., Nature, 455:542 (2008)). The Fc domain also confers antibody effector functions onto CD4-Ig, including the ability to mediate antibody-dependent cell-mediated cytotoxicity, to access mucosal compartments, and to transport across the placenta.

Thus, in some embodiments of the invention, the binding molecule contains an Fc binding region of an immunoglobulin in addition to the moiety recognizing the coreceptor-binding site and the moiety recognizing the CD4-binding site. Exemplary Ig sequences suitable for the invention is shown in SEQ ID NO:5 and SEQ ID NO:14, which respectively contain the hinge region and the Fc domain of a human IgG1 immunoglobulin and a rhesus macaque IgG2 immunoglobulin. As exemplified herein for eCD4-Ig fusion, a number of formats can be adopted in the practice of these embodiments. For example, the binding molecule can be constructed by inserting the CCR5 based peptide (e.g., CCR5mim2) at either N-terminus of the moiety recognizing the CD4-binding site (e.g., CD4 D1D2 domains), between the moiety recognizing CD4-binding site and the Ig sequence, or at the carboxyl terminus of the moiety recognizing the CD4-binding site. Representative binding molecules based on each of these formats are shown in SEQ ID NOs:9-11, respectively. To ensure proper function of each of the components, appropriate linker sequences can be used. For example, a short linker such as SEQ ID NO:7) can be used to couple the moiety recognizing the CD4-binding site and the Ig sequence. Similarly, conjugation between the Ig sequence and the moiety recognizing the coreceptor-binding site can be effected with a linker shown in SEQ ID NO:8. To facilitate post-translational translocation of the binding molecule, a leader sequence can be placed at its N-terminus. Examples of such leader sequences suitable for the invention include the human CD5 leader sequence (SEQ ID NO:6) and rhesus macaque CD4 leader sequence (SEQ ID NO:15).

Representative binding molecules containing a CCR5-mimetic peptide, a CD4 polypeptide and an Fc-binding region are shown in SEQ ID NOs:9-11 and 16-19. As detailed in the Examples herein, these fusion molecules can all neutralize CCR5- and CXCR4-dependent isolates more efficiently than did CD4-Ig. Some embodiments of the invention employ eCD4-Ig (SEQ ID NO:11) or one of the closely related variants (SEQ ID NOs:16-19). eCD4-Ig is a binding molecule wherein CCR5mim1 (SEQ ID NO:1) is inserted at carboxyl terminus of the CD4-Ig molecule (SEQ ID NO:20) via a tetraglycine linker (SEQ ID NO:8). It binds Env cooperatively and with higher avidity than either CD4-Ig or CCR5mim1 alone. As demonstrated herein, eCD4-Ig (SEQ ID NO:11) and its variants (SEQ ID NOs:16-19) are all small enough to be expressed via scAAV, and the encoded CCR5-mimetic peptide component interacts with a small, highly conserved region of gp120. This molecule also promotes the irreversible inactivation of the envelope glycoprotein, observed as shed gp120 in the supernatant.

IV. Tyrosylprotein Sulfotransferases for Tyrosine Sulfating Gp120-binding Molecules The therapeutic compositions of the invention allow co-expression of a tyrosylprotein sulfotransferase (TPST) and a lentiviral gp120-binding molecule at an optimal molar ratio or expression levels. As detailed herein, any TPST capable of tyrosine sulfating the binding molecule, or an enzymatic fragment thereof, may be employed in the practice of the invention. Protein-tyrosine sulfation is a post-translational modification that is well known in the art. Tyrosine-sulfated proteins and/or tyrosylprotein sulfotransferase activity have been described in many species. See, e.g., Huttner et al., Mod. Cell Biol. 6, 97-140, 1988; and Moore, J. Biol. Chem. 278, 24243-24246, 2003.

Protein-tyrosine sulfation is typically mediated by two Golgi tyrosyl-protein sulfotransferases, TPST1 and TPST2. These two enzymes are broadly expressed in human and murine tissues and cell lines and are co-expressed in most, if not all, cell types. TPST1 and/or TPST2 orthologs are also broadly expressed in many other animal species, including vertebrate species (rat, dog, cow, pig, chicken, zebrafish, fugu, channel catfish, and African clawed frog) and invertebrate species. They are type II transmembrane proteins of similar size, e.g., 370 and 376 residues respectively for mouse TPST1 and TPST2. TPST1 and TPST2 each contains a short N-terminal cytoplasmic domain, a single ≈17-residuetransmembrane domain, a membrane proximal ≈40-residue stem region, and a luminal catalytic domain containing four conserved Cys residues and two N-glycosylation sites.

Two structural motifs found in cytosolic and membrane-bound sulfotransferases are conserved in TPST1 and -2. In the known sulfotransferase crystal structures, these motifs are involved in binding of the 5'- and 3'-phosphate groups of the reaction product 3',5'-ADP and are designated the 5'-PSB and 3'-PB motifs, respectively. The amino acid sequence of human and mouse TPST1 are ≈96% identical and human and mouse TPST2 have a similar degree of identity. TPST1 is ≈65-67% identical to TPST2 in both mice and humans. Multiple sequence alignments of TPSTs from various species show that the membrane-proximal portion of the luminal domain is poorly conserved. This ≈40-amino acid segment likely represents a "stem" region that may be dispensable for catalysis, analogous to that found in many glycosyltransferases. The human TPST1 and TPST2 genes are on 7q11.21 and 22q12.1, respectively, whereas the mouse Tpst1 (Mouse Genome Informatics accession number MGI:1298231) and Tpst2 (MGI:1309516) genes are both on chromosome 5, ~18.5 Mb apart. There is no evidence for the existence of additional mouse or human TPST genes in genomic or expressed sequence tag (EST) data bases.

Any of the tyrosyl-protein sulfotransferases known in the art or their enzymatically active fragments may be utilized in the practice of the present invention. For example, TPST1 from human and many other animal species have all been characterized. See, e.g., Ouyang et al., Proc. Natl. Acad. Sci. U.S.A 95, 2896-2901, 1998; Niehrs et al., EMBO J. 9, 35-42, 1990; and William et al., Arch. Biochem. Biophys. 338, 90-96, 1997. TPST2, which shares a high degree of homology to TPST1, has also been identified from human and a number of other species. In some preferred embodiments of the invention, a TPST2 protein or its enzymatically active fragment is used. Many TPST2 orthologs, including human and murine TSPT2, have been structural and functionally characterized. See, e.g., Beisswanger et al., Proc. Natl. Acad. Sci. U.S.A. 95, 11134-11139, 1998; Ouyang et al., J. Biol. Chem. 273, 24770-24774, 1998; Danan et al., J. Am. Soc. Mass. Spectrom. 19:1459-66, 2008; Rosendahl et al., Pancreatol. 10: 165-172, 2010; and Teramoto et al., Nat. Commun. 4: 1572, 2013. As exemplified herein for human TPST2, sequences encoding any of these tyrosylprotein sulfotransferases or enzymatic fragments thereof can be readily obtained via standard molecular closing procedures or from commercial sources (e.g., OriGene, DNASU, and Sino Biological Inc.).

V. Optimal Coexpression of TPST and Gp120-binding Molecule in a Subject

As detailed herein, the invention provides therapeutic compositions that can be administered to a mammal subject in need of long term in vivo protection against or treatment for viral infection. The compositions typically contain expression systems, e.g., polynucleotide sequences, expression vectors or viral particles that encode or express the TPST and the binding molecule. As demonstrated herein, viral neutralizing activities of in vivo produced gp120-binding molecules require the coexpression of a TPST at an optimal ratio. The therapeutic compositions of the invention allow optimal in vivo coexpression in a subject (e.g., human or non-human primate) of a tyrosine protein sulfotranserase and a gp120-binding molecule described herein, which affords potent long term protection against infection of a primate lentivirus (e.g., HIV-1). As detailed in the Examples herein (e.g., Example 3), when vectors expressing TPST2 and eCD4-Ig were coadministered to primate quadricep muscles at a ratio of 1:10, HIV-neutralizing activity of the eCD4-Ig produced in the primate muscle cells is substantially less than functional eCD4-Ig produced in vitro in cell cultures. Surprisingly, it was discovered that full HIV-neutralizing activity of the in vivo produced eCD4-Ig requires the coadministration of viral particles expressing the two proteins at a ratio greater than 1:10, e.g., at around 1:4. At such optimal expression levels, viral neutralizing activity of the binding molecule is about 2-3 fold higher than that of the binding molecule when levels of the two molecules were at a ratio of 1:10. Thus, in the practice of the invention, optimal expression conditions require that the TPST enzyme and the gp120-binding molecule be co-expressed at a molar ratio of greater than 1:10, or at least about 1:8, 1:7, 1:6, 1:5, 1:4, 1:3, 1:2, 1:1 or higher.

Optimal co-expression of the TPST enzyme and the gp120-binding molecule required for practicing the invention can be carried out via various formats. As detailed herein, the optimal ratio of the two proteins expressed in the subject can be achieved by controlling the amounts of coadministered expression vectors or viral particles that separately express the two proteins, by the structural design of the expression vectors, or by the use of appropriate regulatory elements in the expression vectors. In addition, optimal coexpression of the enzyme and the binding molecule in vivo can further ascertained by measuring cellular levels of the two proteins, by quantifying tyrosine-sulfation level of the binding molecule, or by examining virus-neutralizing activity of the expressed gp120 binding molecule. Any of these further tests service to ensure that the expressed binding molecule is sufficiently tyrosine sulfated or functional to be therapeutically effective. These tests can all be readily carried out via the standard assays or protocols exemplified herein or well known in the art.

As exemplifications, using different promoters allows one to determine which regulatory elements in the vectors provides the optimal eCD4-Ig to TPST2 ratio for generating sulfated and functional eCD4-Ig protein. This can be performed by, e.g., quantifying expression of both the eCD4-Ig and TPST2 genes using standard techniques of molecular biology (e.g., qPCR). Alternatively, the expressed proteins can be tested for sulfation by routinely practiced methods, e.g., ELISA with antibodies specific for sulfotyrosine. In other embodiments, the expressed proteins can be examined for viral neutralizing activities with any of the assays exemplified herein or well known in the art, e.g., the TZM-bl neutralization assay.

In some preferred embodiments, polynucleotide sequences encoding the enzyme and the binding molecule are operably-linked to expression control sequences (e.g., promoter sequences) in a virus based expression vector or expression system described herein. Some examples of viral vectors suitable for the invention include retrovirus-based vectors, e.g. lentiviruses, adenoviruses and adeno-associated viruses. In some embodiments, as exemplified herein, the compositions can contain a first recombinant AAV vector (rAAV) or viral particle harboring the vector expressing a TPST2 enzyme, and a second AAV vector or viral particle harboring the vector expressing an eCD4-Ig fusion protein. In some of these embodiments, optimal ratio of the enzyme and the binding molecule (e.g., a 1:4 ratio of expressed molecules or the encoding polynucleotide sequences) can be controlled by expressing the two molecules from otherwise similar expression vectors (e.g., AAV vectors) and co-administering to the subject a composition containing the two expression vectors or viral particles harboring the vectors with the desired ratio. In some embodiments, variance in the structures of the vectors including expression controlling elements (e.g., promoter or enhance sequences) can also be adopted to ensure optimal in vivo expression or cellular levels of the two proteins. As exemplification, therapeutic compositions containing two types of viral particles that respectively express TPST2 and eCD4-Ig from two similarly constructed AAV vectors is described in detail in the Examples herein.

In some other embodiments, the two proteins can be co-expressed from the same polynucleotide sequence, expression vector or viral particle harboring the vector. Using coexpression of TPST2 and eCD4-Ig as an example, the expression vector or expression system contains coding sequences for both of the proteins. Optimal ratio of the two proteins expressed from the same vector or system can be realized via different vector structures. A schematic illustration of the structures of some of these vectors is shown in FIGS. 12(A)-12(D). In some embodiments, a dual promoter can be employed in the expression vector. For example, eCD4-Ig can be placed under the control of a first promoter, and TPST2 is expressed from a second promoter. In some embodiments, the two proteins can be expressed under the control of the same promoter. In these expression systems, relative expression levels of the two proteins can be controlled via the use of appropriate transcription and/or translation regulatory elements, e.g., internal ribosome entry site (IRES) or other regulatory elements described herein. To allow a higher level of eCD4-Ig expression relative to the level of TPST2, the eCD4-Ig expression cassette or coding sequence can be placed at the 5' of the TPST2 expression cassette or coding sequence. In some other embodiments, a bi-directional expression vector can be used to optimally co-express the two proteins.

Various promoter sequences well known in the art can be used in the invention. These include, e.g., CMV promoter, elongation factor-1 short (EFS) promoter, chicken β-actin (CBA) promoter, EF-1α promoter, human desmin (DES) promoter, Mini TK promoter, and human thyroxine binding globulin (TBG) promoter. Additionally, the expression vector can harbor a number of regulatory elements to achieve optimal expression levels of the two proteins. For example, a 5'-enhancer element and/or a 5'-WPRE element can be introduced to elevate expression of one of the two proteins (e.g., eCD4-Ig expression). WPRE is a post-transcriptional response element that has 100% homology with base pairs 1093 to 1684 of the Woodchuck hepatitis B virus (WHV8) genome. When used in the 3' UTR of a mammalian expression cassette, it can significantly increase mRNA stability and protein yield. Other enhancer elements that can be used in the vectors include, e.g., SV40 intron, ubiquitin enhancer and CMB enhancer. Additional regulatory elements that can be used include, e.g., aptazyme, miRNA and miRNA binding elements. To ensure proper posttranscriptional processing, at least one polyadenylation signal sequence, such as SV40 PolyA, bGH PolyA or a synthetic PolyA tail, can be used in the expression vector of the invention.

VI. Methods and Expression Systems for Neutralizing Viral Infection In Vivo

By allowing coexpression of a TPST and a gp120-binding molecule at optimal levels, the invention provides methods that are effective for long term in vivo protection against and/or treatment of lentiviral infections in primate subjects such as human. To practice the methods, the subject is typically administered a pharmaceutical composition that contains an effective amount of the therapeutic composition or expression system of the invention. In some related embodiments, the invention provides therapeutic compositions that contain expression systems for optimally coexpressing the two proteins in the subject. The expression systems can be polynucleotide sequences or expression vectors, as well as liposomes or other lipid-containing complexes, and other macromolecular complexes capable of mediating delivery of a polynucleotide sequence to a host cell or subject. Various expression vectors or systems can be employed in the invention for coexpressing the TPST enzyme and the gp120-binding molecule upon administered into a subject. In some embodiments, the expression vectors or expression systems can be based on viral vectors. In some other embodiments, the expression systems are comprised of polynucleotide sequences harboring coding sequences for the two proteins, including deoxyribonucleic acid and ribonucleic acid sequences. In some embodiments, the expression vectors or systems are administered to subjects in the form of a recombinant virus. For example, the recombinant virus can be a recombinant adeno-associated virus (AAV), e.g., a self-complementary adeno-associated virus (scAAV) vector. Such viral delivery methods provide for safe, unobtrusive and sustained expression (>2 year) of high levels of protein therapeutics.

As described above, when using the therapeutic compositions of the invention for preventing or treating lentiviral infections in a subject (esp. primate subjects), expression levels of the gp120-binding molecule and the TPST, as well as tyrosine sulfation level in the binding molecule can be examined during the treatment process. This is to ensure that the binding molecule is tyrosine sulfated in a sufficient amount to prevent or treat infection by the lentivirus. In some embodiments, the administered compositions should lead to expression and tyrosine sulfation of the binding molecule in the subject in an amount that is sufficient to reduce the number of copies of lentiviral RNA detectable in the plasma of the subject by at least 2-, 3-, 4-, 5-, 6, 7, 8, 9, 10, 15, 20-fold or more. In some preferred embodiments, treatment of the therapeutic compositions of the invention should result in expression of tyrosine sulfated gp120-binding molecule in the subject in an amount that is sufficient to reduce lentiviral RNA to undetectable levels in the blood of the treated subject. The undetectable levels can be defined as fewer than 50 copies of lentiviral RNA per ml of plasma in a real-time reverse transcriptase polymerase chain reaction (real-time RT PCR) assay.

As exemplified herein for AAV-TPST2 or AAV-eCD4-Ig vectors, the expression vectors contain the coding sequences and other components or functionalities that further modulate gene delivery and/or gene expression, or that otherwise provide beneficial properties. Such other components include, for example, components that influence binding or targeting to cells (including components that mediate cell-type or tissue-specific binding); components that influence uptake of the vector by the cell; components that influence localization of the transferred gene within the cell after uptake (such as agents mediating nuclear localization); and components that influence expression of the gene. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. Selectable markers can be positive, negative or bifunctional. Positive selectable markers allow selection for cells carrying the marker, whereas negative selectable markers allow cells carrying the marker to be selectively eliminated. A variety of such marker genes have been described, including bifunctional (i.e., positive/negative) markers (see, e.g., WO 92/08796; and WO 94/28143). Such marker genes can provide an added measure of control that can be advantageous in gene therapy contexts. A large variety of such vectors are known in the art and are generally available.

Expression vectors or systems suitable for the invention include, but are not limited to, isolated polynucleotide sequences, e.g., plasmid-based vectors which may be extra-chromosomally maintained, and viral vectors, e.g., recombinant adenovirus, retrovirus, lentivirus, herpesvirus, poxvirus, papilloma virus, or adeno-associated virus, including viral and non-viral vectors which are present in liposomes, e.g., neutral or cationic liposomes, such as DOSPA/DOPE, DOGS/DOPE or DMRIE/DOPE liposomes, and/or associated with other molecules such as DNA-anti-DNA antibody-cationic lipid (DOTMA/DOPE) complexes. Exemplary gene viral vectors are described below. Vectors may be administered via any route including, but not limited to, intramuscular, buccal, rectal, intravenous or intracoronary administration, and transfer to cells may be enhanced using electroporation and/or iontophoresis.

Some embodiments can employ adeno-associated virus vectors or adenoviral vectors for optimally co-expressing in a subject the TPST enzyme and the gp120-binding molecule. Adenoviral vectors can be made replication-incompetent by deleting the early (E1 A and E1 B) genes responsible for viral gene expression from the genome. They can be stably maintained into the host cells in an extrachromosomal form. These vectors have the ability to transfect both replicating and nonreplicating cells. Adeno-associated virus vectors refer to recombinant adeno-associated viruses (rAAV) that are derived from nonpathogenic parvoviruses. They evoke essentially no cellular immune response, and produce transgene expression lasting months in most systems. Like adenovirus, adeno-associated virus vectors also have the capability to infect replicating and nonreplicating cells and are believed to be nonpathogenic to humans.

Some embodiments of the invention can utilize retroviral vectors. Retroviral vectors exhibit several distinctive features including their ability to stably and precisely integrate into the host genome providing long-term transgene expression. In some of these embodiments, vectors based on lentiviruses can be used. Lentiviruses are derived from a family of retroviruses that include human immunodeficiency virus and feline immunodeficiency virus. However, unlike other retroviruses that only infect dividing cells, lentiviruses can infect both dividing and nondividing cells. In some other embodiments of the invention, other viral vectors such as vectors derived from herpesvirus may be used. These include, e.g., HSV-1-based vectors produced by inserting the exogenous genes into a backbone virus genome and also HSV amplicon virions produced by inserting the exogenous gene into an amplicon plasmid that is subsequently replicated and then packaged into virion particles. HSV-1 can also infect a wide variety of cells, both dividing and non-dividing.

In still some other embodiments, plasmid DNA vectors can be used in the practice of the invention. Plasmid DNA is often referred to as "naked DNA" to indicate the absence of a more elaborate packaging system. Direct injection of plasmid DNA to myocardial cells in vivo has been accomplished. Plasmid-based vectors are relatively nonimmunogenic and nonpathogenic, with the potential to exist as an episome or stably integrate in the cellular genome, resulting in long-term gene expression in postmitotic cells in vivo. Furthermore, plasmid DNA is rapidly degraded in the blood stream; therefore, the chance of transgene expression in distant organ systems is negligible. Plasmid DNA may be delivered to cells as part of a macromolecular complex, e.g., a liposome or DNA-protein complex, and delivery may be enhanced using techniques including electroporation.

VII. Pharmaceutical Compositions and Therapeutic Applications

The invention provides pharmaceutical compositions and related methods of using the therapeutic compositions or expression systems for inhibiting, preventing or treating lentiviral infections (e.g., HIV-1 infections). Also provided in the invention is a use of the polynucleotides and expression vectors or systems described herein for the manufacture of a medicament to prevent or treat primate lentiviral infections. The pharmaceutical composition can be either a therapeutic formulation or a prophylactic formulation. Typically, the pharmaceutical compositions can contain one or more active ingredients and optionally some inactive ingredients. In some embodiments, the active ingredient is comprised exclusively of or comprised essentially of one or two expression vectors or one expression system described herein. In some other embodiments, the active ingredient can include other antiviral agents in addition to the expression system of the invention. The composition can additionally include one or more pharmaceutically acceptable vehicles and, optionally, other therapeutic ingredients (for example, antibiotics or antiviral drugs). Various pharmaceutically acceptable additives can also be used in the compositions.

In some embodiments, the expression system in the pharmaceutical compositions can contain an expression vector or one type of viral particles that optimally co-expresses a TPST and a gp120-binding molecule described herein. In some other embodiments, the therapeutic composition or expression system can contain at an optimal ratio two different vectors or two types of viral particles that respectively expresses the TPST enzyme and the binding molecule. In general, the amount of vector(s) or viral particles administered to achieve a particular outcome will vary depending on various factors including, but not limited to, the gene and promoter chosen, the condition, patient specific parameters, e.g., height, weight and age, and whether prevention or treatment is to be achieved. The vectors or viral particles of the invention may conveniently be provided in the form of formulations suitable for administration, e.g., into the blood stream (e.g., in an intracoronary artery). A suitable administration format may best be determined by a medical practitioner for each patient individually, according to standard procedures.

The pharmaceutical compositions of the invention can be prepared in accordance with standard procedures well known in the art. See, e.g., Remingtons Pharmaceutical Sciences, 19.sup.th Ed., Mack Publishing Company, Easton, Pa., 1995; Sustained and Controlled Release Drug Delivery Systems, J. R. Robinson, ed., Marcel Dekker, Inc., New York, 1978); U.S. Pat. Nos. 4,652,441 and 4,917,893; 4,677,191 and 4,728,721; and 4,675,189. These pharmaceutical compositions of the invention can be readily employed in a variety therapeutic or prophylactic applications for preventing or treating lentiviral infections. For subjects at risk of developing a lentiviral infection, a vaccine composition of the invention can be administered to provide prophylactic protection against viral infection. Depending on the specific subject and conditions, the pharmaceutical compositions of the invention can be administered to subjects by a variety of administration modes known to the person of ordinary skill in the art, for example, intramuscular, subcutaneous, intravenous, intra-arterial, intra-articular, intraperitoneal, or parenteral routes. In general, the pharmaceutical composition is administered to a subject in need of such treatment for a time and under conditions sufficient to prevent, inhibit, and/or ameliorate a selected disease or condition or one or more symptom(s) thereof. For therapeutic applications, the compositions should contain a therapeutically effective amount of the expression system described herein. For prophylactic applications, the compositions should contain a prophylactically effective amount of the expression system described herein. The appropriate amount of the expression system (expression vectors or viral particles) can be determined based on the specific disease or condition to be treated or prevented, severity, age of the subject, and other personal attributes of the specific subject (e.g., the general state of the subject's health and the robustness of the subject's immune system). Determination of effective dosages is additionally guided with animal model studies followed up by human clinical trials and is guided by administration protocols that significantly reduce the occurrence or severity of targeted disease symptoms or conditions in the subject.

For prophylactic applications, the immunogenic composition is provided in advance of any symptom, for example in advance of infection. The prophylactic administration of the immunogenic compositions serves to prevent or ameliorate any subsequent infection. Thus, in some embodiments, a subject to be treated is one who has, or is at risk for developing, a lentiviral infection, for example because of exposure or the possibility of exposure to the virus. Following administration of a therapeutically effective amount of the disclosed therapeutic compositions, the subject can be monitored for the viral infection (e.g., HIV-1 infection), symptoms associated with the viral infection, or both.

For therapeutic applications, the therapeutic composition is provided at or after the onset of a symptom of disease or infection, for example after development of a symptom of HIV-1 infection, or after diagnosis of HIV-1 infection. The therapeutic composition can thus be provided prior to the anticipated exposure to virus so as to attenuate the anticipated severity, duration or extent of an infection and/or associated disease symptoms, after exposure or suspected exposure to the virus, or after the actual initiation of an infection.

In some embodiments, the vectors or viral particles of the invention can be provided in a dosage form containing an amount of a vector effective in one or multiple doses. For viral vectors, the effective dose may be in the range of at least about $10^7$ viral particles, e.g., about $10^9$ viral particles, $10^{11}$ viral particles or $10^{14}$ viral particles. As noted, the exact dose to be administered is determined by the attending clinician, but is may be in 1 mL phosphate buffered saline. For delivery of plasmid DNA alone, or plasmid DNA in a complex with other macromolecules, the amount of DNA to be administered will be an amount which results in a beneficial effect to the recipient. For example, from 0.0001 to 1 mg or more, e.g., up to 1 g, in individual or divided doses, e.g., from 0.001 to 0.5 mg, or 0.01 to 0.1 mg, of DNA can be administered. For delivery of the fusion polypeptide, the amount administered is an amount which results in a beneficial effect to the recipient. For example, from 0.0001 to 100 g or more, e.g., up to 1 g, in individual or divided doses, e.g., from 0.001 to 0.5 g, or 0.01 to 0.1 g, of fusion polypeptide can be administered.

The pharmaceutical composition of the invention can be combined with other agents known in the art for treating or preventing lentiviral infections. These include, e.g., antibodies or other antiviral agents such as nucleoside reverse transcriptase inhibitors, such as abacavir, AZT, didanosine, emtricitabine, lamivudine, stavudine, tenofovir, zalcitabine, zidovudine, and the like, non-nucleoside reverse transcriptase inhibitors, such as delavirdine, efavirenz, nevirapine, protease inhibitors such as amprenavir, atazanavir, indinavir, lopinavir, nelfinavir, osamprenavir, ritonavir, saquinavir, tipranavir, and the like, and fusion protein inhibitors such as enfuvirtide and the like. Administration of the pharmaceutical compostion and the known anti-HIV agents can be either concurrently or sequentially.

The expression systems or pharmaceutical compositions of the invention can be provided as components of a kit. Optionally, such a kit includes additional components including packaging, instructions and various other reagents, such as buffers, substrates, antibodies or ligands, such as control antibodies or ligands, and detection reagents. An optional instruction sheet can be additionally provided in the kits.

EXAMPLES

The following examples are offered to illustrate, but not to limit the present invention.

Example 1 eCD4-Ig Fusions and its Binding to HIV Env

We reasoned that a fusion of CD4-Ig and CCR5mim1 would bind Env cooperatively and with higher avidity than either molecule alone. Accordingly, three fusion proteins were generated. CCR5mim1 was inserted at either the CD4-Ig amino-terminus (fusion 1; SEQ ID NO:9), between the CD4 and Fe domain (fusion 2; SEQ ID NO:10), or at the CD4-Ig carboxyl terminus (fusion 3, renamed eCD4-Ig; SEQ ID NO:11). All three CD4-Ig variants neutralized CCR5- and CXCR4-dependent isolates more efficiently than did CD4-Ig, with eCD4-Ig consistently the most potent (FIGS. 5a and 5b). eCD4-Ig neutralized a wider panel of HIV-1 isolates and SIVmac316 with 10- to 100-fold lower $IC_{50}$s than CD4-Ig (FIG. 1b). Improved neutralization of SIVmac316 is consistent with conservation of the Env's sulfotyrosine-binding pockets, and a first indication of the exceptional breadth of eCD4-Ig.

Figures 6A, 6B:
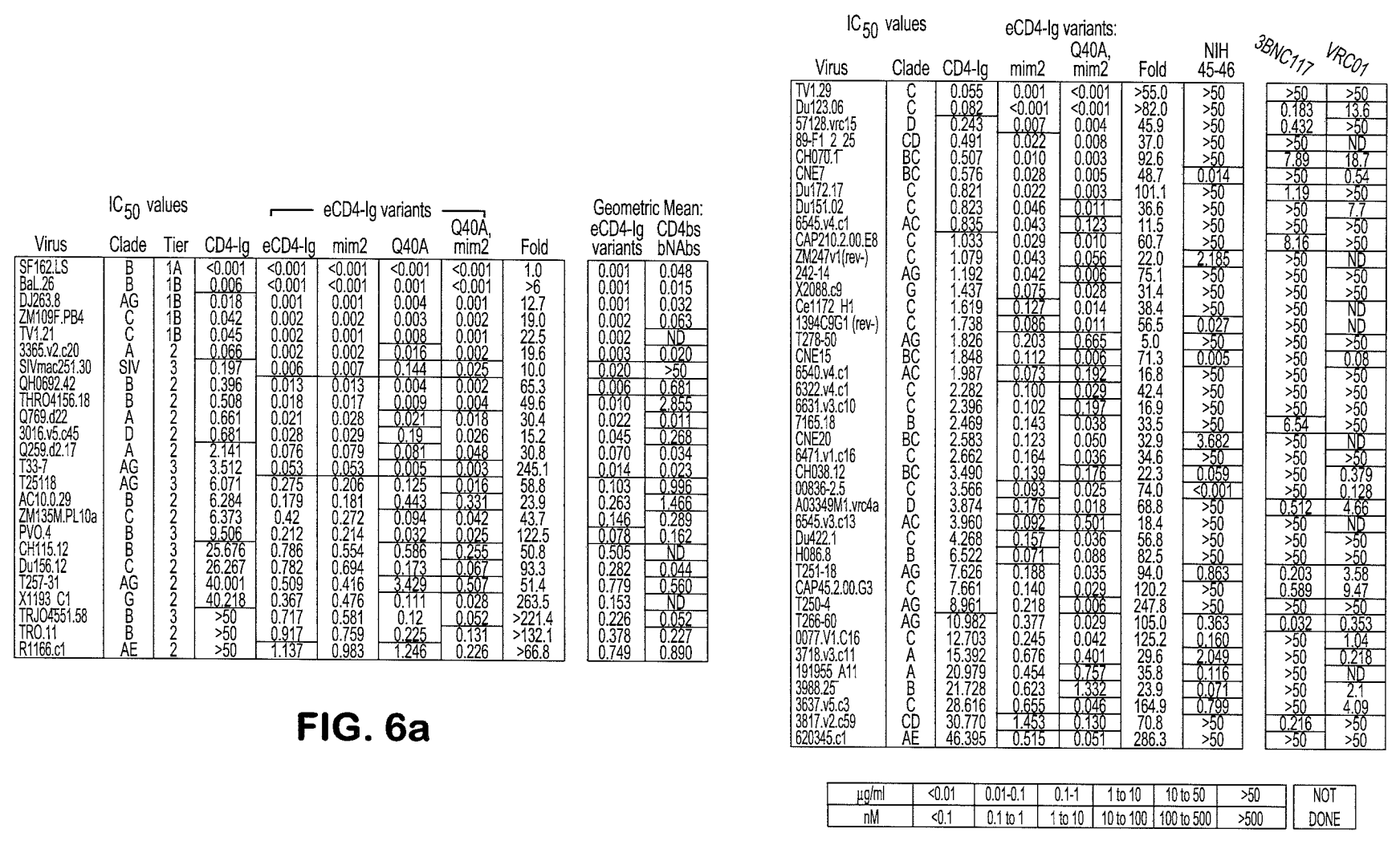

To better understand the markedly greater potency of eCD4-Ig relative to CD4-Ig, we compared their abilities to bind cell-surface expressed Env trimers (FIG. 1c). At low concentrations, eCD4-Ig bound these trimers more efficiently than did CD4-Ig. Surprisingly, eCD4-Ig saturated trimer-expressing cells with approximately one-third less bound protein than CD4-Ig, suggesting that eCD4-Ig's sulfopeptides made some CD4-binding sites inaccessible. eCD4-Ig also less efficiently promoted HIV-1 infection of CCR5-positive, CD4-negative cells than CD4-Ig (FIG. 1d), presumably because its sulfopeptides blocked virion access to cell-surface CCR5. CD4-Ig/eCD4-Ig heterodimers neutralized less potently than eCD4-Ig (FIG. 1e; FIGS. 5c-5e), indicating that both eCD4-Ig sulfopeptides engage the Env trimer, consistent with a model of eCD4-Ig bound to Env (FIGS. 6a-6b). Thus the markedly greater potency of eCD4-Ig relative to CD4-Ig is due in part to the higher avidity with which it binds Env and to its decreased ability to promote infection.

Example 2

In Vitro HIV-inhibiting Activities of eCD4-Ig

We next assessed eCD4-Ig under more physiological conditions. We observed that eCD4-Ig, but not CD4-Ig, halted replication of infectious viruses in human PBMC at concentrations as low as 125 ng/mL (FIGS. 5f and 5g). We administered sufficient eCD4-Ig to humanized NOD/SCID/γc (NSG) mice to maintain serum concentrations of 2-4 µg/m at the time of challenge. Five eCD4-Ig treated mice and six control mice were challenged intravenously with $5 \times 10^4$ infectious units of HIV-$1_{NL4-3}$. Five of six control mice, but no eCD4-Ig inoculated mice, were infected (FIG. 1h; FIG. 5h). Five weeks later, three eCD4-Ig-treated mice and the uninfected control mouse were rechallenged. Again, no eCD4-Ig-treated mouse was infected, whereas the control mouse became infected.

Figures 7A, 7B:
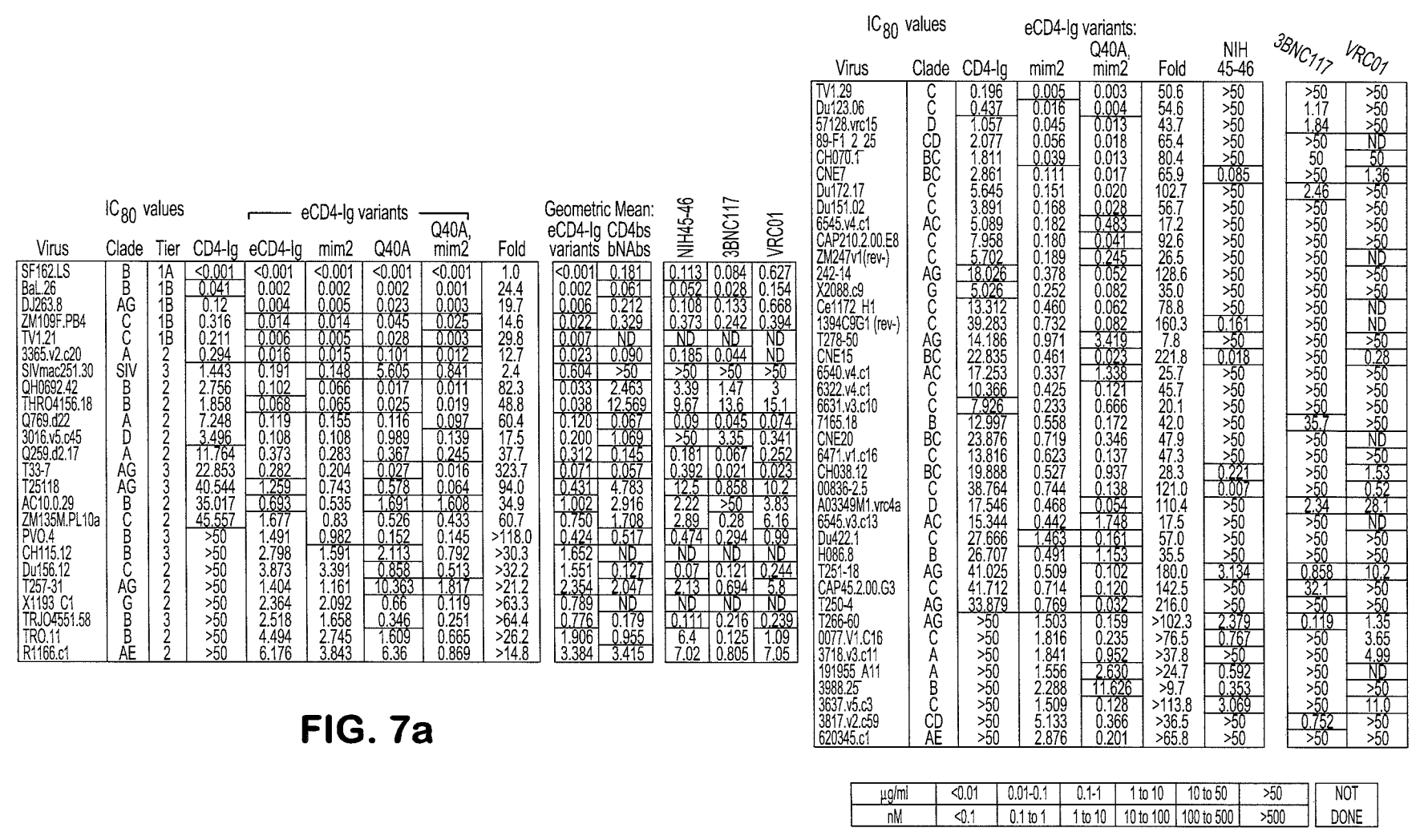

We then characterized the ability of eCD4-Ig to neutralize a diverse panel of neutralization resistant tier 2 and 3 viruses (FIGS. 6a and 7a). In parallel, we assayed three additional eCD4-Ig variants. In the first, eCD4-Ig$^{mim2}$, CCR5mim1 was replaced by CCR5mim2, which differs from CCR5mim1 by single alanine to tyrosine substitution. We also introduced a previously characterized glutamine 40 to alanine mutation into CD4 domain 1 of eCD4-Ig (eCD4-Ig$^{Q40A}$) (Moebius et al., J. Exp. Med. 176, 507-517, 1992). Both mutations were combined in a final variant (eCD4-Ig$^{Q40A,mim2}$). eCD4-Ig and these variants substantially outperformed CD4-Ig for every virus in the panel, typically improving neutralization potency by 20 to >200-fold. Underscoring its breadth, eCD4-Ig neutralized SIVmac251 33 times more efficiently than CD4-Ig. In general, the more neutralization resistant a virus, the better eCD4-Ig and its variants performed relative to CD4-Ig. In most cases, replacement of CCR5mim1 with CCR5mim2 modestly improved neutralization. Similarly, the Q40A mutation also improved neutralization of most HIV-1 isolates, but not of SIVmac251.

Figure 2B:
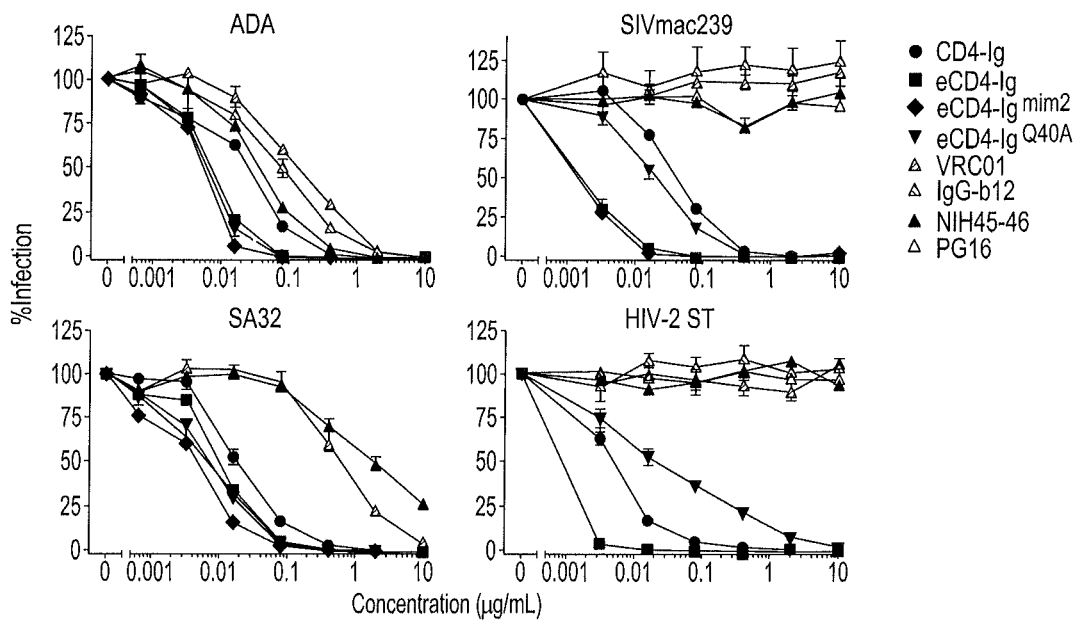
Figure 2C:
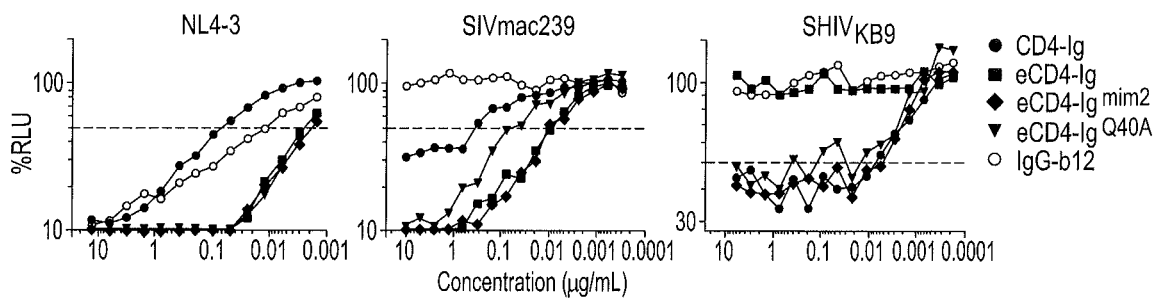

We compared eCD4-Ig, eCD4-Ig$^{mim2}$ and eCD4-Ig$^{Q40A,mim2}$ with a panel of 12 antibodies and inhibitors using three additional HIV-1 isolates (FIG. 2a; FIGS. 8a and 8b). eCD4-Ig and its variants neutralized the SG3 and YU2 isolates more efficiently than any of these inhibitors. Five bNAbs neutralized JR-CSF more efficiently than any eCD4-Ig variant, but four of these could not neutralize SG3. All eCD4-Ig variants neutralized these isolates with IC$_{50}$s less than 0.3 µg/ml, more efficiently than CD4-Ig, the tetrameric CD4-Ig variant PRO-542, or the antibodies 2G12, 4E10, and VRC01. eCD4-Ig and its variants, but not three CD4-binding site bNAbs, neutralized the neutralization-resistant SIVmac239 as well as HIV-2 ST (FIG. 2b; FIG. 8c). As observed with SIVmac251, the Q40A variant was less efficient at neutralizing SIVmac239 and HIV-2. The potency of these eCD4-Ig variants was also reflected in their abilities to mediate antibody-dependent cell-mediated cytotoxicity (ADCC). eCD4-Ig, eCD4-Ig$^{mim2}$, and eCD4-Ig$^{Q40A,mim2}$ each facilitated 30-40 times more killing of infected cells by CD16+ natural killer cells than did CD4-Ig or the antibody IgGb12 (FIG. 2c). Thus the carboxyl-terminal modification of eCD4-Ig did not interfere with the ADCC effector function of its Fc domain.

Figure 3A:
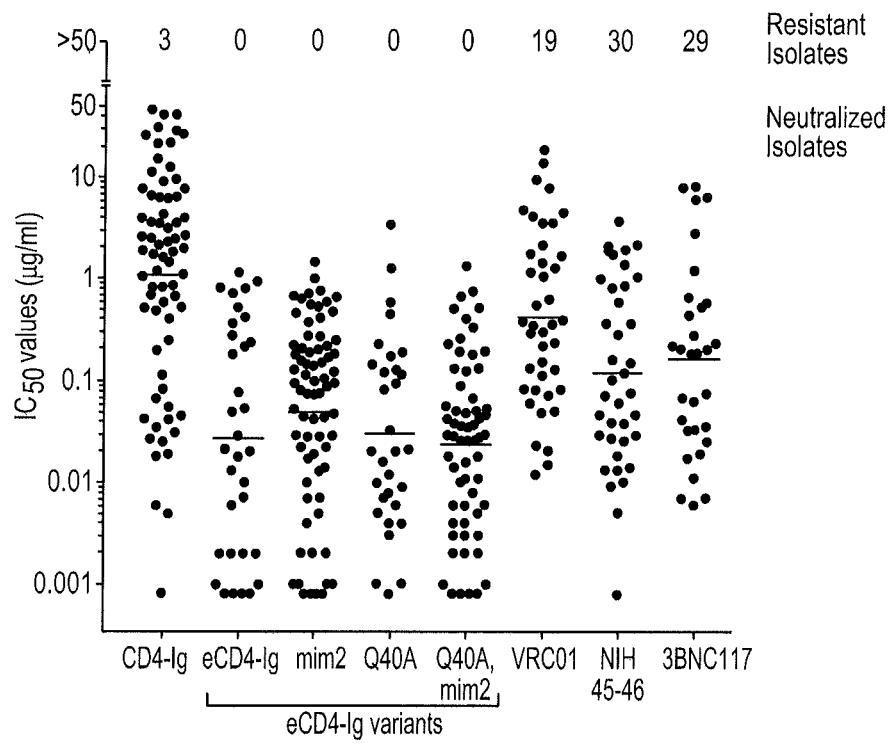
Figure 3B:
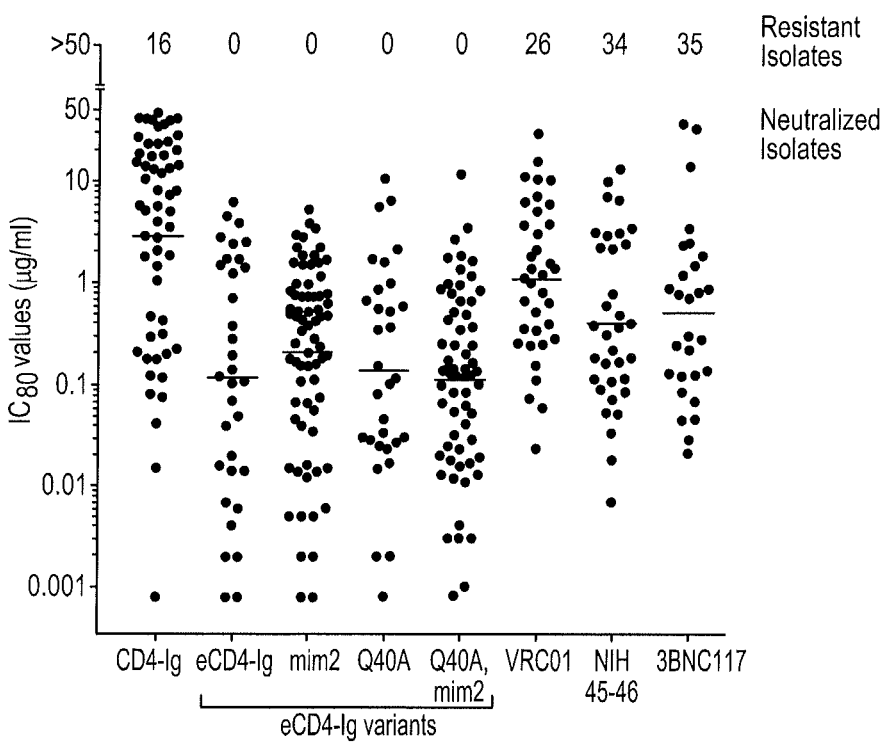
Figure 9:
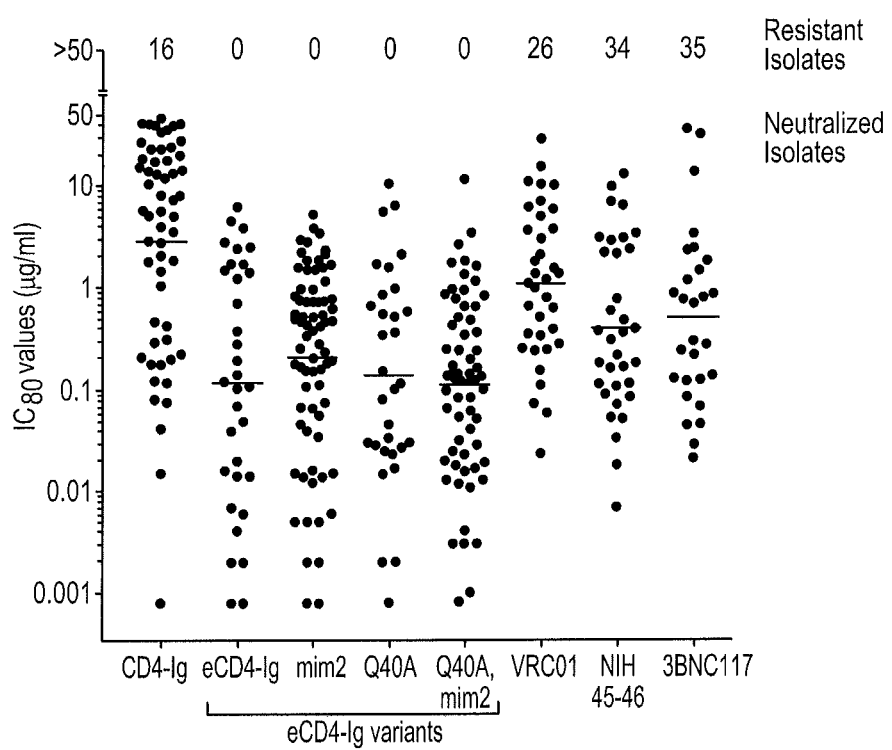

We further evaluated eCD4-Ig, eCD4-Ig$^{mim2}$, eCD4-Ig$^{Q40A,mim2}$ and the bNAb NIH45-46 using nearly every isolate reported to be resistant to either of the CD4bs antibodies NIH45-46 or 3BNC117 (FIGS. 6b and 7b). Both eCD4-Ig variants efficiently neutralized all 38 resistant isolates assayed with IC$_{50}$s ranging from <0.001 µg/ml to 1.453 µg/ml. In contrast, 26 isolates in this panel were confirmed to be resistant to NIH45-46. 29 isolates and 18 isolates have been previously reported resistant to 3BCN117 and VRC01, respectively. FIGS. 3a-3b and FIG. 9 summarize the neutralization studies compiled from the experiments in FIGS. 1a-2c, FIGS. 6a-8c, and from previous studies of VRC01 and 3BNC117 against the same isolates (Huang et al., Nature 491, 406-412, 2012). They show that the geometric mean IC$_{50}$ and IC$_{80}$ values of eCD4-Ig and its variants are less than 0.05 µg/ml (500 pM) and 0.2 µg/ml (2 nM), respectively, roughly 3-4 times lower than those of VRC01, NIH45-46, or 3BNC117. Importantly, our lead eCD4-Ig variant, eCD4-Ig$^{mim2}$, neutralized 100% of the isolates assayed at concentrations (IC$_{50}$<1.5 µg/ml; IC$_{80}$<5.2 µg/ml) likely sustainable in humans.

Example 3

In Vivo Protection by Coadministering TPST2 and eCD4-Ig Vectors

The in vivo properties of eCD4-Ig variants were investigated in rhesus macaques using a rhesus macaque form of eCD4-Ig$^{mim2}$ (rh-eCD4-Ig$^{mim2}$). To minimize potential adverse reactions in vivo, the Fc domain of the rh-eCD4-Ig$^{mim2}$ was generated from rhesus macaque IgG2, which binds Fc receptors and complement components less efficiently than IgG1. A gene expressing this rh-eCD4-Ig$^{mim2}$ was inserted into a self-complementary AAV (scAAV) vector, and $2 \times 10^{13}$ AAV1 particles delivering this vector were administered into the quadriceps of three 2-year old, Indian-origin, male rhesus macaques. To promote efficient sulfation of the CCR5mim2 component, a separate scAAV vector expressing rhesus tyrosine-protein sulfotransferase 2 (TPST2) was also administered in the same injections at a 1:10 ratio with the scAAV-rh-eCD4-Ig$^{mim2}$ AAV1 particles (i.e., $0.2 \times 10^{13}$ TPST2-expressing viral particles). Note that, although this TPST2 vector improves eCD4-Ig sulfation in in vitro studies (not shown), it is not yet clear whether it does so in vivo. Blood was collected from AAV-inoculated macaques at −4, −2, 0, 2, 4, 8 and 10 weeks after administration and sera were analyzed for rh-eCD4-Ig$^{mim2}$ concentrations and anti-rh-eCD4-Ig$^{mim2}$ antibody responses. rh-eCD4-Ig$^{mim2}$ titers stabilized to 6-12 µg/ml by week 10

(FIG. 11a), indicating the transgene expressed efficiently, but at somewhat lower levels than has been reported with antibody-like immunoadhesins delivered with a similar vector (Johnson et al., Nat. Med. 15, 901-906, 2009). No adverse reactions were observed for any macaque throughout the experiment.

Studies in rhesus macaques using adeno-associated virus (AAV) vectors to express neutralizing antibodies or CD4-Ig have shown that anti-transgene antibody responses can emerge, and that these responses can interfere with the activity of AAV-delivered inhibitors (Johnson et al., supra). For example, the majority of 12 macaques expressing the anti-SIV antibodies 5L7 or 4L6 produced antibodies recognizing these AAV-expressed antibodies detectable four to six weeks after administration of the AAV vector (S.F., R.C., in preparation). Similarly, it was reported that two of three macaques expressing a single-chain immunoadhesin form of 5L7 also generated anti-immunoadhesin responses, although no such response was observed with the 4L6 immunoadhesin (Johnson et al., supra). The same study observed that one of three macaques expressing approximately 5 µg/ml of a rhesus form of CD4-Ig (N4-Ig) developed an anti-N4-Ig response in the same time frame. However, in our studies, anti-rh-eCD4-Ig$^{mim2}$ antibody responses could not be detected through week 10 in any of the three macaques expressing this transgene (FIGS. 11b-11c). These data suggest that rh-eCD4-Ig$^{mim2}$ is not more immunogenic than N4-Ig, 5L7, or 4L6 in rhesus macaques.

To determine if AAV-expressed rh-eCD4-Ig$^{mim2}$ retained its HIV-1 neutralization activity, we compared sera from the three inoculated macaques with pre-inoculation sera mixed with purified rh-eCD4-Ig$^{mim2}$ at the same concentrations. Serum from all three inoculated macaques did neutralize two HIV-1 isolates (89.6 or SF162). However, when viral particles containing the TPST2 vector and the eCD4-Ig$^{mim2}$ vector were injected at a 1:10 ratio, the observed HIV-1 neutralization activities of the in vivo AAV-expressed rh-eCD4-Ig$^{mim2}$ are only about 40-50% of the activity observed with sera mixed with the same concentrations of rh-eCD4-Ig$^{mim2}$ which was produced in cell culture.

We also tested whether using single-stranded AAV (ssAAV) vectors could improve rh-eCD4-Ig$^{mim2}$ transgene expression in macaques. The ssAAV vectors contain components shown to increase transgene expression such as a wood chuck element (WPRE) and a full CMV promoter. The rhesus-eCD4-Ig$^{mim2}$ used in this study contains one amino acid substitution, I39N. In this study, we also increased the amount of TPST2 AAV inoculation to 20%. When using the ssAAV vectors containing a full CMV promoter and WPRE, we observed greater expression of rh-eCD4-Ig$^{I39N,mim2}$ in macaques with titers peaking at greater than 100 µg/mL in three of the four macaques we tested. Surprisingly, we also observed that, at the 20% level of TPST2 AAV inoculation (i.e., at 1:4 molar ratio of TPST2 vector and rh-eCD4-Ig vector), the expressed rh-eCD4-Ig$^{I39N,mim2}$ retained 100% of its activity at weeks 4 and 6 post AAV inoculation.

Figure 4A:
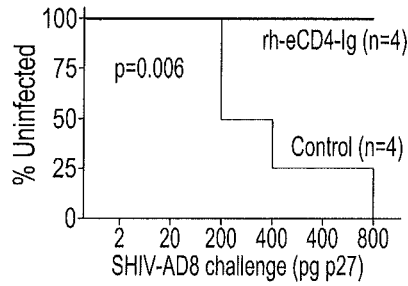
Figure 4B:
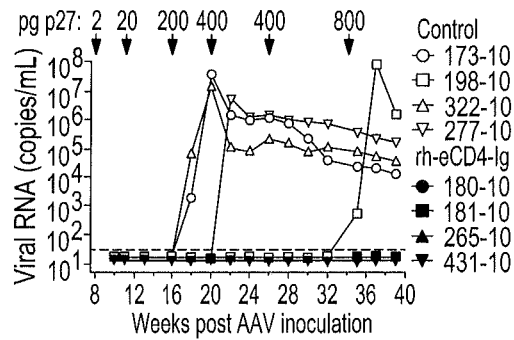

We then examined in vivo protective effect of co-expressed eCD4-Ig vector and TPST2 in macaques against viral infection. Single-stranded AAV vector expressing rhesus tyrosine-protein sulfotransferase 2 (AAV-rh-TPST2; FIG. 10c) was co-administered with AAV-rh-eCD4-Ig at a 1:4 ratio. No adverse reactions were observed in any of the AAV-rh-eCD4-Ig inoculated macaques. These macaques and four age- and gender-matched controls were challenged intravenously with increasing doses of SHIV-AD8 (FIGS. 4a and 4b). 16 weeks post-AAV inoculation, two control macaques became infected following challenge with 200 pg p27. A subsequent 400 pg challenge infected a third control animal, and, after resisting an additional 400 pg challenge, the final control was infected with 800 pg, 34 weeks from the date of AAV inoculation. None of these challenges infected AAV-rh-eCD4-Ig inoculated macaques, indicating that eCD4-Ig protected them from four doses capable of infecting control animals.

Figure 4C:
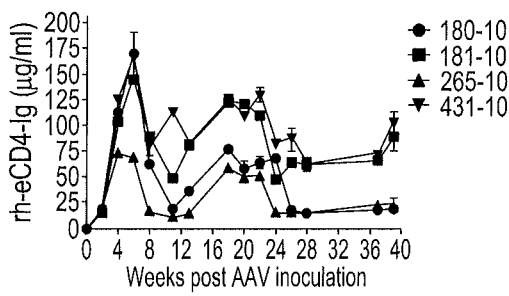
Figure 4D:
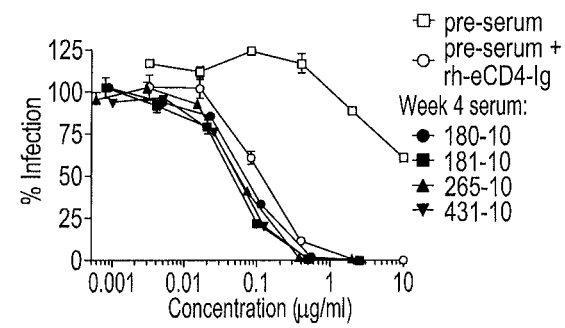
Figure 4E:
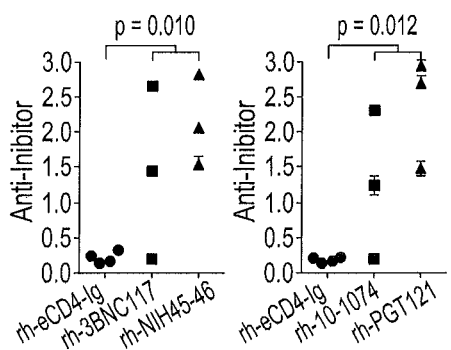
Figure 4F:
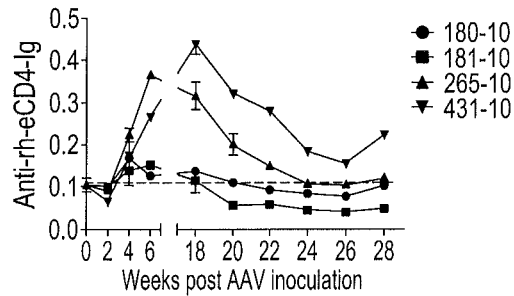
Figure 4G:
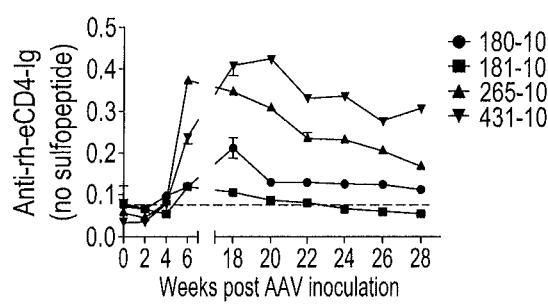
Figure 4H:
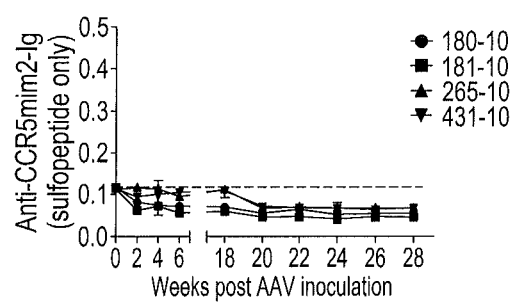

Measured rh-eCD4-Ig titers in the serum stabilized to between 17 and 77 µg/ml over the last ten weeks of the 40-week study period (FIG. 4c). Two macaques expressed less than 20 µg/m at the time of the final 800 pg challenge, suggesting that this concentration could prevent many otherwise infectious exposures in humans. Sera from inoculated macaques neutralized HIV-1 as efficiently as laboratory-prepared rh-eCD4-Ig mixed with pre-inoculation sera (FIG. 4d; FIG. 10d), indicating that the eCD4-Ig was efficiently sulfated and fully active in vivo, We also compared macaque humoral responses to expressed rh-eCD4-Ig and to four AAV-expressed bNAbs inoculated for a separate study. 3BNC117, NIH45-45, 10-1074, and PGT121, each bearing rhesus IgG2 and light-chain constant domains, elicited markedly higher endogenous antibody responses than did rh-eCD4-Ig, consistent with their high levels of somatic hypermutation (FIG. 4e). To investigate the target of the anti-rh-eCD4-Ig responses, we increased the sensitivity of our assay and compared longitudinally the reactivity of inoculated rhesus sera to a series of antigens. rh-eCD4-Ig (FIG. 4f) and rh-CD4-Ig (without the CCR5mim2 sulfopeptide; FIG. 4g) were recognized by rhesus sera with nearly the same reactivity, whereas CCR5mim2 fused to a human IgG1 Fc domain was not (FIG. 4h), indicating that the sulfopeptide was not immunogenic. Rhesus CD4 domains 1 and 2 fused to a human IgG1 Fc was much less reactive than the same CD4 domains fused to the rhesus IgG2 Fc, without or with the I39N mutation (FIGS. 10e and 10f), whereas an unrelated construct bearing the rhesus IgG2 Fc domain showed no reactivity (FIG. 10g), suggesting that a neo-epitope formed by the rhesus CD4 and Fc domains was recognized by most anti-rh-eCD4-Ig antibodies. Thus eCD4-Ig is less immunogenic than bNAbs, and can be expressed for at least 40 weeks at concentrations that are well tolerated and protective against several robust SHIV-AD8 challenges.

Example 4

Expressing TPST2 and eCD4-Ig from the Same Vector

Figure 13:
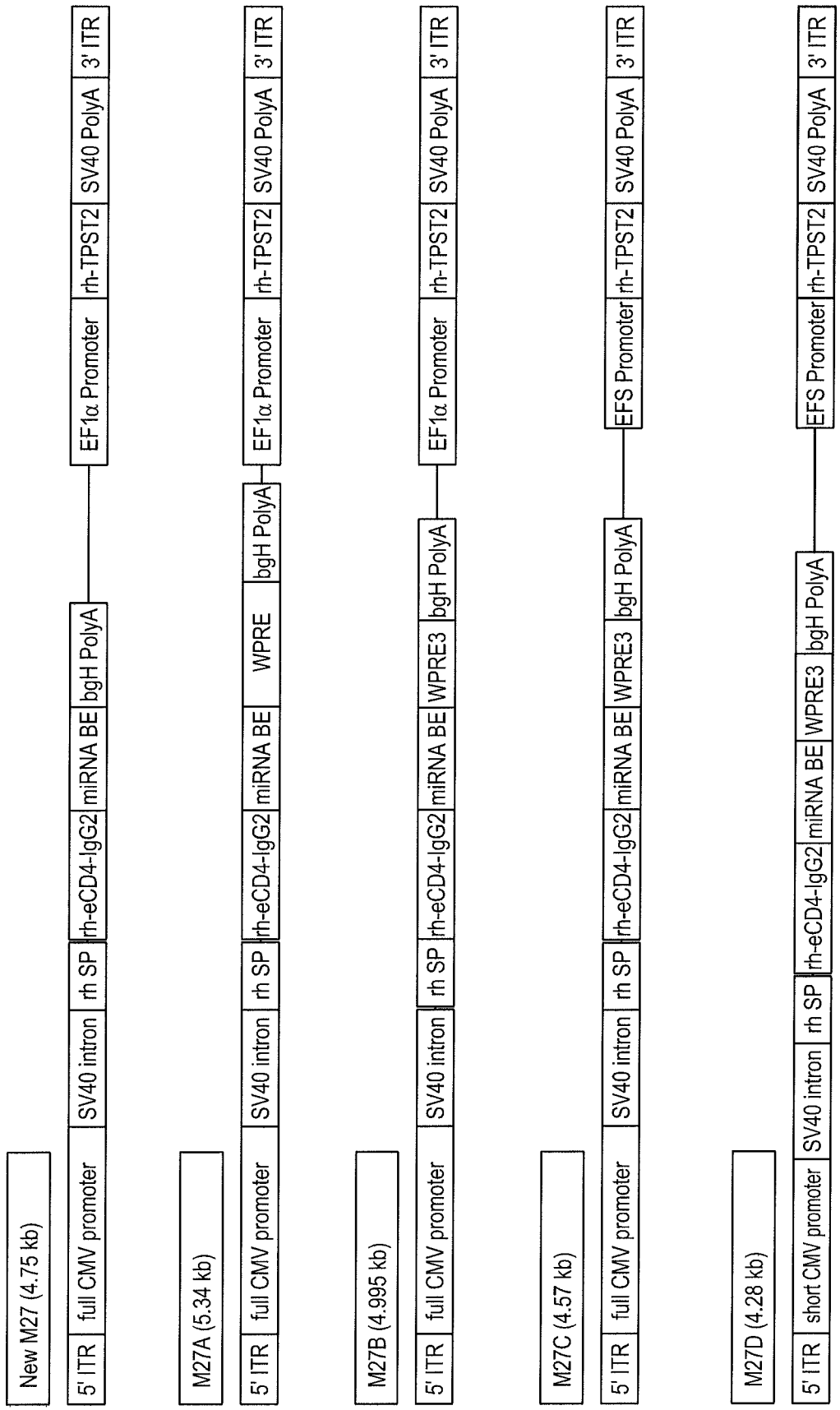
FIG. 13 shows schematic structures of dual promoter vectors expressing both eCD4-Ig and TPST2 genes.
Figure 14:
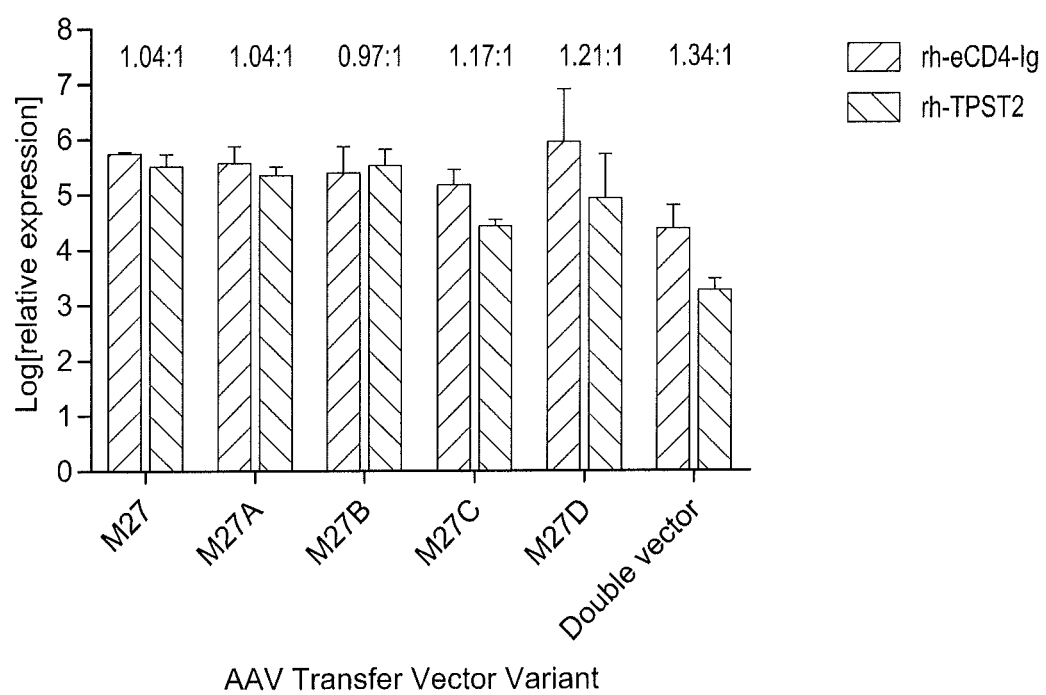
FIG. 14 shows results from qRT-PCR study of rh-eCD4-Ig and rh-TPST2 expression from M27 transfer vectors.

We have created and analyzed 5 different transfer vectors (M27 or M27A-D) that use two promoters to produce the rh-eCD4-Ig and rh-TPST2 genes. As shown in FIG. 13, a full or short CMV promoter was used for rh-eCD4-Ig and an EF1-alpha or EFS (shortened EF1-alpha) promoter was used for rh-TPST2. Values next to the labels indicate the number of DNA base pairs between the 5' and 3' ITRs. We performed qRT-PCR assays to determine expression of rh-eCD4-Ig and rh-TPST2 relative to RPLP0 expression. Data represent the average of two independent experiments are shown in FIG. 14. Values above the bar graph indicates the ratio of rh-eCD4-Ig expression to rh-TPST2 expression. "Double vector" describes co-transfection of the V68 rh-eCD4-Ig plasmid and V68 rh-TPST2 plasmid at a 4:1 ratio, respectively. This data indicates that we are expressing rh-eCD4-Ig at a ratio to rh-TPST2 that is comparable to that of a co-transfection of the two transfer vectors.

Figure 15:
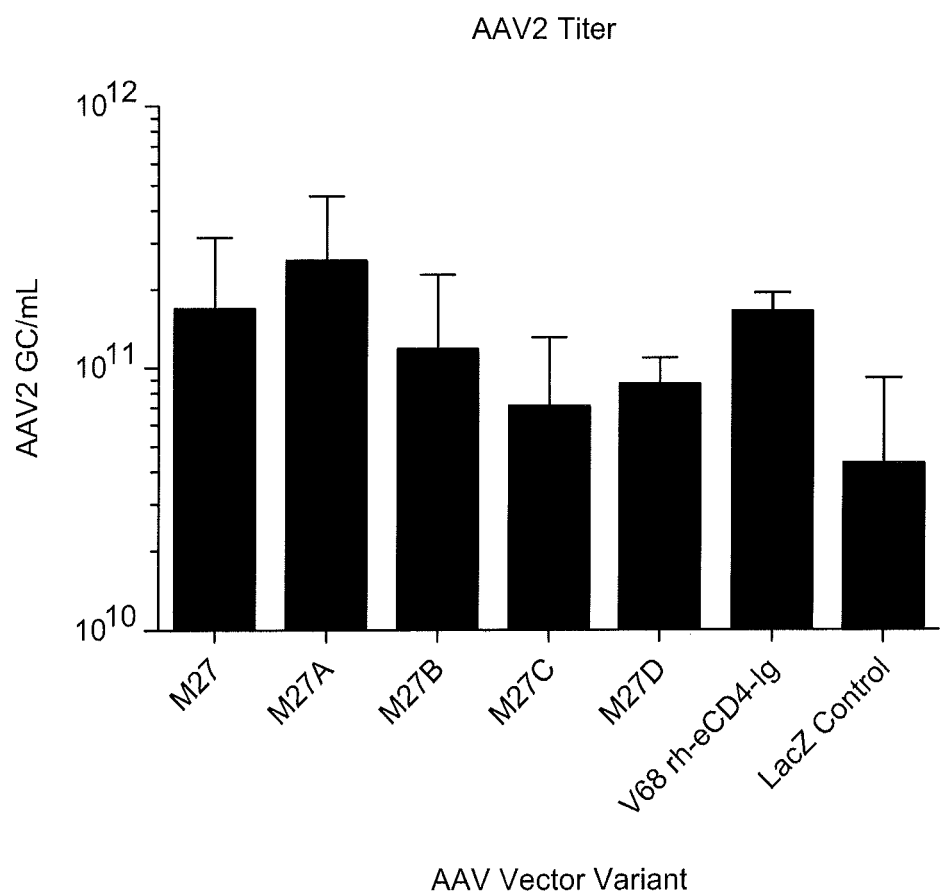
FIG. 15 shows AAV2 vector titers from encapsidation quantification analysis of the M27 vectors.

We then co-transfected our M27, V68 rh-eCD4-Ig, or LacZ transfer vectors with adenovirus helper plasmid and AAV2 rep/cap plasmid to produce AAV2 viral vectors. We used the QuickTiter AAV Quantification Kit by Cell Biolabs, Inc to titer the vector produced in the cells. Results from this study are shown in FIG. 15. The data shown in the figure represent the average of three independent experiments. In general, viral vector production was similar to that of our V68 rh-eCD4-Ig and LacZ vector controls indicating that although the transfer vectors are larger in gene cassette size, we do not see a greater decrease in viral vector production.

Figure 16:
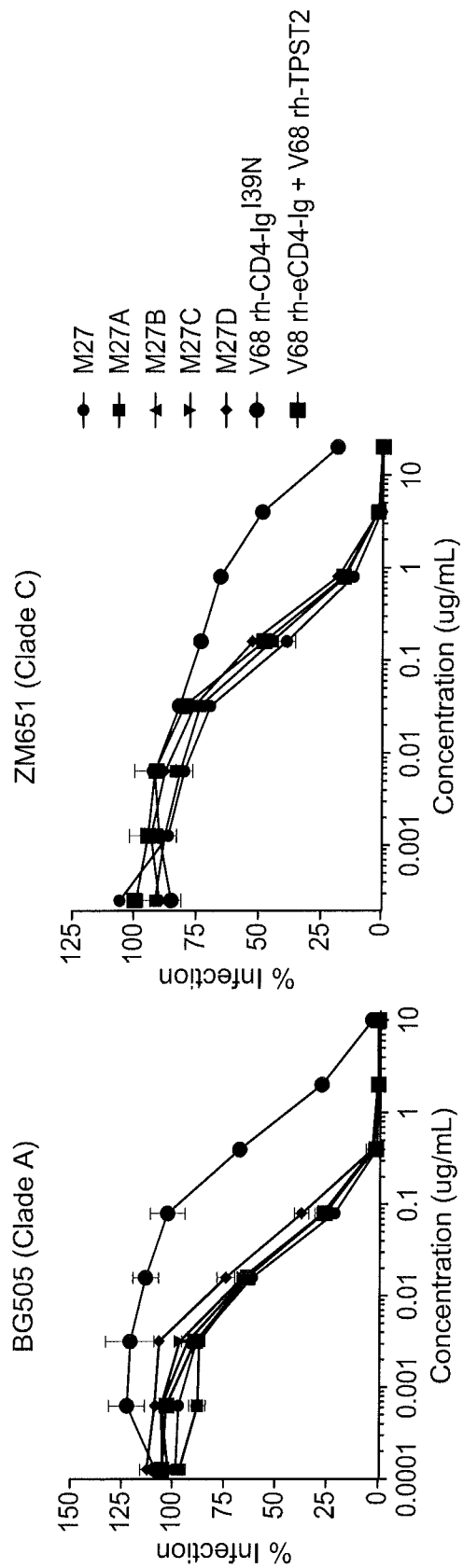
FIG. 16 shows results from neutralization assays on two HIV-1 isolates.

We further performed TZM.b1 neutralization assays on HIV-1 pseudovirus. As shown in FIG. 16, the results indicate that proteins produced from all M27 transfer vectors neutralize HIV-1 with the same potency as rh-eCD4-Ig protein produced from co-transfection of the V68 rh-eCD4-Ig and V68 rh-TPST2 vectors (at a 4:1 ratio). This functional assay indicates that the rh-eCD4-Ig produced in the M27 vectors is just as sulfated as protein produced from co-transfection.

Example 5

Some Exemplified Materials and Methods

Plasmids and cells. Plasmid expressing CD4-Ig was previously described in, e.g., Dorfman et al., J. Biol. Chem. 281, 28529-28535, 2006. Fusion constructs were created by adding sequences encoding CCR5mim1 and tetra-glycine linker to N-terminus (fusion1) or between domain 2 and human Fc (fusion2) of CD4-Ig by inverse PCR. eCD4-Ig (fusion3) and eCD4-Ig$^{mim2}$ were created by adding sequence encoding a tetra-glycine linker and CCR5mim1 or CCR5mim2, respectively, to the C-terminus of CD4-Ig by inverse PCR. The glutamine 40 to alanine mutation was introduced in eCD4-Ig and eCD4-Ig$^{mim2}$ by Quickchange PCR. The eCD4-Ig/CD4-Ig heterodimer was generated as previously described (Ridgway et al., Prot. Eng. 9, 617-621, 1996) and analyzed by SDS-PAGE under reducing and non-reducing conditions. rh-eCD4-Ig, consisting of rhesus CD4 domains 1 and 2 bearing an I39N mutation, rhesus IgG1 Fc, and CCR5mim2, was synthesized and cloned into a previously described single-stranded AAV plasmid (Johnson et al., supra). AAV expression plasmids for HIV-1 antibodies were created by synthesizing the variable heavy and light chains of 3BNC117, NIH45-46, PGT121, and 10-1074 with the rhesus heavy and light constant regions, and cloning these genes into a previously described ssAAV plasmid that has been previously described (Johnson et al., supra). The following reagent was obtained through the NIH AIDS Reagent Program (Division of AIDS, NIAID, NIH): CMVR-VRC01-H, CMVR-VRC01-L, from Dr. John Mascola (Wu et al, Science 329, 856-861, 2010; and Barouch et al., J. Virol. 79, 8828-8834, 2005), pNL4-3.Luc.R-.E-from Dr. Nathaniel Landeau (He et al., J. Virol. 69, 6705-6711, 1995; and Connor et al., Virol. 206, 935-944, 1995), TZM-b1 cells from Dr. John C. Kappes, Dr. Xiaoyun Wu, and Tranzyme Inc. (Platt et al., J. Virol. 83, 8289-8292, 2009; Takeuchi et al., J. Virol. 82, 12585-12588, 2008; Wei et al., Antimicrobial Agents and Chemotherapy 46, 1896-1905, 2002; Derdeyn et al., J. Virol. 74, 8358-8367, 2000; and Platt et al., J. Virol. 72, 2855-2864, 1998), SF162 gp160 from Dr. Leonidas Stamatatos and Dr. Cecilia Cheng-Mayer (Harouse et al., J. Virol. 75, 1990-1995, 2001), and GHOST-CCR5 and -CXCR4-cells from V. KewalRamani and D. Littman. The variable heavy and light chains of IgG-b12, NIH45-46, 3BNC117, 10-1074, and PGT121 were cloned into the CMVR-VRC01-H and -L plasmids. Plasmids encoding TPST2 or the envelope glycoproteins pNL4-3Δenv, 89.6, ADA, SG3, SA32, YU2, JRFL, KB9, VSV-G, HIV-2 ST, SIVmac239, SIVmac316, and replicative 89.6 or SG3 viruses were previously described (Dorfman et al., supra; Choe et al., Cell 114, 161-170, 2003; Choe et al., J. Virol. 72, 6113-6118, 1998; Choe et al., Cell 85, 1135-1148, 1996; and Farzan et al., J. Virol. 72, 1160-1164, 1998). Human embryonic kidney HEK293T cells were obtained from ATCC. Cf2Th-CD4+.CCR5+ and CfTh-CCR5+ cells were a generous gift from Dr. Hyeryun Choe.

Purification of antibodies, CD4-Ig, and eCD4-Ig variants. Production of CD4-Ig, eCD4-Ig variants and antibodies was performed as previously described (Quinlan et al., supra). Briefly, HEK293T cells in 140 mm plates were transfected with 25 µg/plate at 50% confluency by the calcium phosphate transfection method. Plasmids encoding sulfated proteins were cotransfected with a plasmid encoding human tyrosine protein sulfotransferase 2 (TPST2). At 12 hrs post-transfection, 10% FBS-DMEM media was replaced with serum-free 293 Freestyle media (Invitrogen). Media was collected after 48 hrs, debris was cleared by centrifugation for 10 min at 1,500 g and filtered using 0.45 µm filter flasks (Millipore). Complete protease inhibitor cocktail (Roche) was added to the filtered supernatants. 500 µl bed volume of Protein A sepharose beads (GE Healthcare) were added and were agitated 4° C. overnight. The bead/media mixture was collected by gravity flow column (Biorad) and was washed with 30 mL phosphate buffered saline (PBS; Lonza)+0.5M NaCl (0.65M NaCl final) followed by 10 mL PBS. Protein was eluted with 3M MgCl$_2$ in PBS. Buffer was exchanged for PBS and protein was concentrated to 1 mg/ml by Ultrafiltration (Amicon Ultra) at 4,000 g.

Flow cytometry analysis of CD4-Ig and eCD4-Ig binding to cell-expressed envelope glycoprotein. HEK293T cells were transfected with plasmids expressing envelope glycoprotein lacking cytoplasmic residues 732 to 876 (HXBc2 numbering) together with plasmid encoding the tat protein. Transfection medium was replaced after an overnight incubation and cells were harvested 48 hours post transfection. Harvested cells were washed twice in flow cytometry buffer (PBS with 2% goat serum, 0.01% sodium azide). Cells were incubated with CD4-Ig or eCD4-Ig on ice for 1 hour and then washed twice with flow cytometry buffer. A secondary antibody recognizing human Fc (Jackson Immuno Research) was added to the cells for 30 minutes. Cells were washed twice with flow cytometry buffer, twice with PBS, and resuspended in 1% paraformaldehyde solution. Binding was analyzed with an Accuri C6 Flow Cytometer (BD Biosciences) and data analyzed with the C6 Software (BD Biosciences).

Viral entry enhancement assay. HIV-1 pseudovirus expressing firefly luciferase was pre-incubated with titrated amounts of CD4-Ig or eCD4-Ig variants in DMEM (10% FBS) for 1 hour at 37° C. CD4-negative Cf2Th-CCR5 cells were harvested and diluted in DMEM (10% FBS) to 100,000 cells/mL and added to the pseudovirus/inhibitor mixture. Cells were then incubated for 48 hours at 37° C. Viral entry was analyzed using Britelite Plus (Perkin Elmer) and luciferase activity of cell lysates was read using a Victor X3 plate reader (Perkin Elmer).

HIV-1 neutralization assays. GHOST-CCR5 or -CXCR4 cells were plated into 12-well plates at 50,000 cells per well. HIV-1 pseudovirus was diluted in RPMI and titrated amounts of CD4-Ig, fusion 1, fusion2, or eCD4-Ig were added. Virus and inhibitor were incubated at room temperature for 20 minutes and added to the cells for 2 hours at 37° C. Cells were then washed with serum free medium and then incubated in 1 mL of DMEM (10% FBS) for 48 hours at 37° C. Cells were harvested by trypsinization, fixed in 1% paraformaldehyde in PBS, and viral entry was determined by flow cytometry based on GFP expression.

For studies of infectious virus, unstimulated PBMCs were harvested and resuspended in RPMI medium (15% FBS, 20 U/mL IL-2). Cells were plated in a 12-well plate at $10^6$ cells per well. HIV-1 was diluted in RPMI and varying amounts of inhibitor were added. The virus and inhibitor was incubated at room temperature for 20 minutes and added to the cells for 3 hours at 37° C. Cells were then washed with serum-free medium and resuspended in fresh RPMI medium (15% FBS, 20 U/mL IL-2). At 3-day intervals post infection, supernatants were collected and fresh RPMI medium (15% FBS, 20 U/mL IL-2) was added to the cells. Supernatants were analyzed for viral infection by ELISA with Alliance HIV-1 p24 antigen ELISA kit (Perkin Elmer).

TZM-bl neutralization assays were performed as previously described (Li et al., J. Virol. 79, 10108-10125, 2005). Briefly, HIV-1 pseudoviruses were pre-incubated with titrated amounts of CD4-Ig or eCD4-Ig variants in DMEM (10% FBS) for 1 hour at 37° C. TZM-bl cells were harvested and diluted in DMEM (10% FBS) to 100,000 cells/mL and added to the pseudovirus/inhibitor mixture. Cells were then incubated for 48 hours at 37° C. Viral entry was analyzed using Britelite Plus (Perkin Elmer) and luciferase activity was read using a Victor X3 plate reader (Perkin Elmer). All neutralization and enhancement studies of FIGS. 1a-4h were performed at least twice in triplicate. All error bars represent S.E.M.

Antibody-dependent cell-mediated cytotoxicity assays. ADCC activity was performed as previously described (Alpert et al., PLoS Pathog 8, e1002890, 2012). Briefly, CEM.NKR CCR5 CD4+ T cells were infected 4 days with infectious HIV-1 NL4.3, SHIV-KB9, or SIVmac239. After 4 days, KHYG-1 effector cells were co-incubated with infected cells in the presence of titrated CD4-Ig, eCD4-Ig variants, or the b12 antibody for 8 hours. ADCC activity was measured by luciferase activity as above.

Production of HIV-$1_{NL4-3}$ stocks and SHIV-AD8-EO stocks for in vivo studies. A molecular clone of HIV-$1_{NL4-3}$ was obtained from the AIDS Research and Reference Reagent Program (ARRRP), Division of AIDS, NIAID, NIH from material deposited by Suzanne Gartner, Mikulas Popovic, Robert Gallo and Malcolm Martin. Virus stocks were produced in 293T cells by transient transfection using TurboFect (Thermo Scientific) and 12 µs of proviral plasmid. Supernatants were harvested at 40 hours, filtered through 0.45 µm filters, and dispensed into single use doses and frozen at −80° C. Viruses were quantified by p24 ELISA (Zeptometrix, Buffalo, N.Y.) and by GHOST cell titer[44] to determine infectious units per mL (IU/mL). Titering was performed per the GHOST cell line protocol obtained through ARRRP. The molecular clone of SHIV-AD8-EO was a generous gift from Dr. Malcom Martin (Shingai et al., Nature, 503:277-80, 2013). 293T cells were plated in 140 mm flasks and transfected with 80 µg DNA/plate by calcium phosphate technique. At 12 hour post transfection, flasks were replaced with fresh DMEM (10% FBS). Medium was harvested at 48 hours post transfection, frozen at −80 C, and tittered using an SIV p27 ELISA kit (ABL).

Hematopoietic stem cell isolation and NSG mouse transplantation. Human CD34+ hematopoietic stem cells (HSC) were isolated from fetal livers obtained from Advanced Bioscience Resources, INC (ABR, Alameda, Calif.). Tissue was disrupted and incubated with 1 mg/mL Collagenase/Dispase (Roche Applied Sciences) for 15 min at 37° C. Cells were isolated by passing the disrupted tissue through a 70 µm filter. Red blood cells were lysed in BD Pharm Lyse (BD Biosciences, San Jose, Calif.), with CD34+ cells being isolated using CD34 MACS microbeads (Miltenyi) according to manufacturer's instructions with an additional purification step using a second column. NOD.Cg-Prkdc scid Il2rγ tm1Wj/Szj (NOD/SCID/IL2rγ$^{null}$, NSG) mice were obtained from Jackson Laboratories (Bar Harbor, Me.). Neonatal mice received 150 cGy radiation, and 2-4 hours later $1 \times 10^6$ CD34+ HSCs in 1% heparin (Celgene, Summit, N.J.) via intrahepatic injection. Mice were monitored for engraftment levels of human CD45+ cells and development of T cells and B cells at 8, 10, and 12 weeks post engraftment.

Mouse infections, treatment, and analysis. Humanized mice with evidence of human CD4+ T cell development in blood were infected with $5 \times 10^4$ IU of HIV-1NL4.3 by intraperitoneal injection. Mice were administered with 65 µg of eCD4-Ig once weekly for the first 2 weeks, starting at 8 day prior to the HIV-1 challenge, and then twice weekly starting week 3 by retro-orbital injection while under anesthetization by 2.5% isofluoane. Mock treated mice received a retro-orbital injection of PBS one and eight days preceding HIV-1 challenge, and were anesthetized in parallel with eCD4-Ig mice throughout. Every week post-infection the mice were anesthetized by inhalation of 2.5% isoflourane and blood was collected retro-orbitally for analysis. At week 6, three eCD4-Ig treated mice and one mock treated mouse (who had not become infected) were challenged a second time with $5 \times 10^4$ IU HIV-INL4-3. Mouse blood was blocked for 20 minutes at room temperature in FBS (Denville) and stained with appropriate antibodies for 15 minutes at room temperature. Red blood cells were removed by incubation in BD FACS Fix/Lysing Solution (BD Biosciences), which was removed by dilution with PBS prior to analysis by flow cytometry. HIV-1 levels in peripheral blood were determined by extracting viral RNA from mouse plasma at each blood draw using a viral RNA isolation kit (Qiagen, Germantown, Md.) followed by Taqman One-Step RT-PCR (Life Technologies, Carlsbad, Calif.) using a primer and probe set targeting the HIV-1 LTR region, as previously described in Holt et al., Nat. Biotechnol. 28, 839-847, 2010; and Rouet et al., J. Clin. Microbiol. 43, 2709-2717, 2005. Reactions were performed and analyzed using a 7500 Fast Realtime PCR System (Life Technologies). To analyze engrafted T cells by flow cytometry, stained cells were acquired on a FACS Canto II (BD Biosciences) and analyzed using FlowJo software v7.6.5 (Tree Star Inc., Ashland, Oreg.). Blood samples were stained using human-specific antibodies at a 1:20 dilution for CD4-V450 (RPA-T4), CD8-APC (RPAT8), CD3-PE (UCHT1), and CD45-PerCP (TUI16) (BD Bioscience). Up to 10,000 events were recorded for viable cell populations and gated based on fluorescence minus one controls as described in Holt et al., Nat. Biotechnol. 28, 839-847, 2010.

AAV inoculation of rhesus macaques. Eight four-year old AAV1-negative male Indian-origin rhesus macaques were housed at the New England Primate Research Center in accordance with standards set forth by the American Association for Accreditation of Laboratory Animal Care. Their weights at the time of AAV inoculation ranged from 5.2 to 8.2 kg. Four macaques were inoculated with 1 mL saline containing $2.5 \times 10^{13}$ AAV1 particles containing 80% of a single-strand rh-eCD4-Ig transgene (IgG2 isotype) and 20% of a single-strand rhesus TPST2 transgene into both quadriceps muscle (two 0.5 mL per injections per quadriceps muscle). 1 mL of sera was obtained every one to two weeks post-AAV inoculation beginning at Week 4. Animals were challenged at Week 8 post-inoculation with 2 pg p27 of SHIV-AD8-EO. SHIV-negative animals were repeatedly challenged with escalating doses of SHIV-AD8-EO up to 800 pg p27. Plasma viral loads were quantified as described in Shingai et al. (supra).

For AAV studies of bNAbs, six two-year old AAV1-negative Indian-origin rhesus macaques (two males and four females) were housed at the New England Primate Research Center in accordance with standards set forth by the American Association for Accreditation of Laboratory Animal Care. Three macaques were inoculated with 1 mL saline containing 1×10[13] AAV1 particles delivering single-strand rh-3BNC117-IgG2 transgene into one quadriceps (two 0.5 mL injections) and 1 mL saline containing 1×10[13] AAV1 particles delivering single-strand rh-10-1074-IgG2 transgene into the second quadriceps (two 0.5 mL injections). The other three macaques were inoculated with 1 mL saline containing 1×10[13] AAV1 particles delivering single-strand rh-NIH45-46-IgG2 transgene into one quadriceps (two 0.5 mL injections) and 1 mL saline containing 1×10[13] AAV1 particles delivering single-strand rh-PGT121-IgG2 transgene into the second quadriceps (two 0.5 mL injections). 1 mL of sera was obtained every two weeks beginning at Week 2 and analyzed by ELISA.

eCD4-Ig, rh-eCD4-Ig and anti-transgene antibody concentrations in NSG mice and rhesus macaque sera. In vivo concentrations of eCD4-Ig, rh-eCD4-Ig were measured by ELISA as previously described (Johnson et al., supra). Briefly, to measure NSG mouse and macaque serum concentrations, ELISA plates (Costar) were coated with 5 µg/mL SIV gp120 overnight at 4° C. Plates were washed with PBS-T (PBS+0.05% Tween-20) twice and blocked with 5% milk in PBS for 1 hour at 37° C. Sera serially diluted in 5% milk in PBS were added to the plate and incubate for 1 hour at 37° C. Samples were washed five times with PBS-T and a horseradish peroxidase secondary antibody (Jackson Immuno Research) recognizing human IgG1. Plates were incubated for 1 hour at 37° C. and then washed ten times with PBS-T. TMB solution (Fisher) was added for 10 minutes at room temperature and then stopped with TMB Stop Solution (Southern Biotech). Absorbance was read at 450 nm by a Victor X3 plate reader (Perkin Elmer) and compared with a standard curve generated using a rh-eCD4-Ig mixed with pre-inoculation sera. Anti-rh-eCD4-Ig antibodies and anti-bNAb antibodies were measured in the same way except that ELISA plates were coated with 5 µg/mL of various constructs. Constructs so assayed included rh-eCD4-Ig, rh-CD4-Ig[I39N], rh-CD4-Ig domains 1 and 2 (with or without I39N) bearing a human IgG1 Fc and hinge domain, C-terminal CCR5mim2-Ig (human IgG1 Fc and hinge, no CD4 domains), NIH45-46 bearing the rhesus IgG2 Fc domain and hinge, or HIV-1 bNAbs. Serum samples were diluted 10- or 20-fold and blocked in 5% milk in PBS. Anti-transgene antibodies were measured using secondary antibodies detecting either the kappa or lambda light chain (Southern Biotech) that was opposite of the antibody being assayed when comparing the anti-bNAb response to that to rh-eCD4-Ig. Both anti-kappa and anti-lambda secondary antibodies were used when measuring anti-rh-eCD4-Ig responses alone. TMB solution was added for 10-15 minutes at room temperature and measured as described above.

LIST OF SEQUENCES

Some peptide and polynucleotide sequences exemplified herein for practicing the invention are listed below.

CCR5mim1 (SEQ ID NO: 1):
GDYADYDGGYYYDMD

CCR5mim2 (SEQ ID NO: 2):
GDYYDYDGGYYYDMD

Human CD4 domain 1 (D1) (SEQ ID NO: 3):
KKVVLGKKGDTVELTCTASQKKSIQFHWKNSNQIKILGNQGSFLTKGP

SKLNDRADSRRSLWDQGNFPLIIKNLKIEDSDTYICEVEDQKEEVQLL

VF

Human CD4 domains 1 and 2 (D1D2) (SEQ ID NO: 4):
KKVVLGKKGDTVELTCTASQKKSIQFHWKNSNQIKILGNQGSFLTKGP

SKLNDRADSRRSLWDQGNFPLIIKNLKIEDSDTYICEVEDQKEEVQLL

VFGLTANSDTHLLQGQSLTLTLESPPGSSPSVQCRSPRGKNIQGGKTL

SVSQLELQDSGTWTCTVLQNQKKVEFKIDIVVLA

Human CD4 D1D2 variant (Q40A mutant)
(SEQ ID NO: 12):
KKVVLGKKGDTVELTCTASQKKSIQFHWKNSNQIKILGNAGSFLTKGP

SKLNDRADSRRSLWDQGNFPLIIKNLKIEDSDTYICEVEDQKEEVQLL

VFGLTANSDTHLLQGQSLTLTLESPPGSSPSVQCRSPRGKNIQGGKTL

SVSQLELQDSGTWTCTVLQNQKKVEFKIDIVVLA

Rhesus macaque CD4 D1D2 variant (I39N mutant)
(SEQ ID NO: 13):
KKVVLGKKGDTVELTCNASQKKNTQFHWKNSNQIKILGNQGSFLTKGP

SKLSDRADSRKSLWDQGCFSMIIKNLKIEDSDTYICEVENKKEEVELL

VFGLTANSDTHLLEGQSLTLTLESPPGSSPSVKCRSPGGKNIQGGRTI

SVPQLERQDSGTWTCTVSQDQKTVEFKIDIVVLAFQKASST

Human IgG1 hinge and Fc (SEQ ID NO: 5):
EPKSCDKTHTCPPCPAPELLGGPSVFLFPPKPKDTLMISRTPEVTCVV

VDVSHEDPEVKFNWYVDGVEVHNAKTKPREEQYNSTYRVVSVLTVLHQ

DWLNGKEYKCKVSNKALPAPIEKTISKAKGQPREPQVYTLPPSRDELT

KNQVSLTCLVKGFYPSDIAVEWESNGQPENNYKTTPPVLDSDGSFFLY

SKLTVDKSRWQQGNVFSCSVMHEALHNHYTQKSLSLSPGK

Rhesus IgG2 hinge and Fc (SEQ ID NO: 14):
GLPCRSTCPPCPAELLGGPSVFLFPPKPKDTLMISRTPEVTCVVVDVS

QEEPDVKFNWYVDGVEVHNAQTKPREEQFNSTYRVVSVLTVTHQDWLN

GKEYTCKVSNKALPAPRQKTVSKTKGQPREPQVYTLPPPREELTKNQV

SLTCLVKGFYPSDIVVEWASNGQPENTYKTTPPVLDSDGSYFLYSKLT

VDKSRWQQGNTFSCSVMHEALHNHYTQKSLSVSPGK

Human CD5 leader sequence (SEQ ID NO: 6):
MPMGSLQPLATLYLLGMLVASVLA

Rhesus macaque CD4 leader sequence
(SEQ ID NO: 15):
MNRGIPFRHLLLVLQLALLPAVTQG

Linker between CD4 domains and Ig sequence
(SEQ ID NO: 7):
AADP

Linker between Ig sequence and CCR5 mimetic
(SEQ ID NO: 8):
GGGG

Fusion 1 (CCR5mim1 fused to N-terminus of CD4 D1D2) (SEQ ID NO: 9):

```
MPMGSLQPLATLYLLGMLVASVLAGDYADYDGGYYYDMDGGGGKKVVL
GKKGDTVELTCTASQKKSIQFHWKNSNQIKILGNQGSFLTKGPSKLND
RADSRRSLWDQGNFPLIIKNLKIEDSDINICEVEDQKEEVQLLVEGLT
ANSDTHLLQGQSLTLTLESPPGSSPSVQCRSPRGKNIQGGKTLSVSQL
ELQDSGTWTCTVLQNQKKVEFKIDIVVLAAADPEPKSCDKTHTCPPCP
APELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNK
ALPAPIEKTISKAKGQPREPQVYTLPPSRDELTKNQVSLTCLVKGFYP
SDIAVEWESNGQPENNYKTTPPVLDSDGSFFLYSKLTVDKSRWQQGNV
FSCSVMHEALHNHYTQKSLSLSPGK

Fusion 2 (CCR5mim1 fused between CD4 D1D2 and
Ig) (SEQ ID NO: 10):
MPMGSLQPLATLYLLGMLVASVLAKKVVLGKKGDTVELTCTASQKKSI
QFHWKNSNQIKILGNQGSFLTKGPSKLNDRADSRRSLWDQGNFPLIIK
NLKIEDSDTYICEVEDQKEEVQLLVFGLTANSDTHLLQGQSLTLTLES
PPGSSPSVQCRSPRGKNIQGGKTLSVSQLELQDSGTWTCTVLQNQKKV
EFKIDIVVLAAAGGGGDYADYDGGYYYDMDDPEPKSCDKTHTCPPCP
APELLGGPSVFLEPPKPKDTLMISRTPEVTCVVVDVSHEDPEVKFNWY
VDGVEVHNAKTKPREEQYNSTYRVVSVLTVLHQDWLNGKEYKCKVSNK
ALPAPIEKTISKAKGQPREPQVYTLPPSRDELTKNQVSLTCLVKGFYP
SDIAVEWESNGQPENNYKTIPPVLDSDGSFELYSKLTVDKSRWQQGNV
FSCSVMHEALHNHYTQKSLSLSPGK eCD4-Ig (CCR5mim1 fused to C-terminus of CD4
D1D2) (SEQ ID NO: 11):
MPMGSLQPLATLYLLGMLVASVLAKKVVLGKKGDTVELTCTASQKKSI
QFHWKNSNQIKILGNQGSFLTKGPSKLNDRADSRRSLWDQGNFPLIIK
NLKIEDSDTYICEVEDQKEEVQLLVFGLTANSDTHLLQGQSLTLTLES
PPGSSPSVQCRSPRGKNIQGGKTLSVSQLELQDSGTWTCTVLQNQKKV
EFKIDIVVLAAADPEPKSCDKTHTCPPCPAPELLGGPSVFLFPPKPKD
TLMISRTPEVTCVVVDVSHEDPEVKFNWYVDGVEVHNAKTKPREEQYN
STYRVVSVLTVLHQDWLNGKEYKCKVSNKALPAPIEKTISKAKGQPRE
PQVYTLPPSRDELTKNQVSLTCLVKGFYPSDIAVEWESNGQPENNYKT
TPPVLDSDGSFFLYSKLTVDKSRWQQGNVFSCSVMHEALHNHYTQKSL
SLSPGKGGGGDYADYDGGYYYDMD eCD4-Ig$^{mim2}$ variant (containing CCR5mim2)
(SEQ ID NO: 16):
MPMGSLQPLATLYLLGMLVASVLAKKVVLGKKGDTVELTCTASQKKSI
QFHWKNSNQIKILGNQGSFLTKGPSKLNDRADSRRSLWDQGNFPLIIK
NLKIEDSDTYICEVEDQKEEVQLLVFGLTANSDTHLLQGQSLTLTLES
PPGSSPSVQCRSPRGKNIQGGKTLSVSQLELQDSGTWTCTVLQNQKKV
EFKIDIVVLAAADPEPKSCDKTHTCPPCPAPELLGGPSVFLFPPKPKD
TLMISRTPEVTCVVVDVSHEDPEVKFNWYVDGVEVHNAKTKPREEQYN
STYRVVSVLTVLHQDWLNGKEYKCKVSNKALPAPIEKTISKAKGQPRE
PQVYTLPPSRDELTKNQVSLTCLVKGFYPSDIAVEWESNGQPENNYKT
TPPVLDSDGSFFLYSKLTVDKSRWQQGNVFSCSVMHEALHNHYTQKSL
SLSPGKGGGGDYYDYDGGYYYDMD eCD4-Ig$^{Q40A}$ variant (containing CD4$^{Q40A}$ mutation)
(SEQ ID NO: 17):
MPMGSLQPLATLYLLGMLVASVLAKKVVLGKKGDTVELTCTASQKKSI
QFHWKNSNQIKILGNAGSFLTKGPSKLNDRADSRRSLWDQGNFPLIIK
NLKIEDSDTYICEVEDQKEEVQLLVFGLTANSDTHLLQGQSLTLTLES
PPGSSPSVQCRSPRGKNIQGGKTLSVSQLELQDSGTWTCTVLQNQKKV
EFKIDIVVLAAADPEPKSCDKTHTCPPCPAPELLGGPSVFLFPPKPKD
TLMISRTPEVTCVVVDVSHEDPEVKFNWYVDGVEVHNAKTKPREEQYN
STYRVVSVLTVLHQDWLNGKEYKCKVSNKALPAPIEKTISKAKGQPRE
PQVYTLPPSRDELTKNQVSLTCLVKGFYPSDIAVEWESNGQPENNYKT
TPPVLDSDGSFFLYSKLTVDKSRWQQGNVFSCSVMHEALHNHYTQKSL
SLSPGKGGGGDYYDYDGGYYYDMD eCD4-Ig$^{Q40A, mim2}$ variant (having CCR5mim2 and
CD4$^{Q40A}$) (SEQ ID NO: 18):
MPMGSLQPLATLYLLGMLVASVLAKKVVLGKKGDTVELTCTASQKKSI
QFHWKNSNQIKILGNAGSFLTKGPSKLNDRADSRRSLWDQGNFPLIIK
NLKIEDSDTYICEVEDQKEEVQLLVFGLTANSDTHLLQGQSLTLTLES
PPGSSPSVQCRSPRGKNIQGGKTLSVSQLELQDSGTWTCTVLQNQKKV
EFKIDIVVLAAADPEPKSCDKTHTCPPCPAPELLGGPSVFLFPPKPKD
TLMISRTPEVTCVVVDVSHEDPEVKFNWYVDGVEVHNAKTKPREEQYN
STYRVVSVLTVLHQDWLNGKEYKCKVSNKALPAPIEKTISKAKGQPRE
PQVYTLPPSRDELTKNQVSLTCLVKGFYPSDIAVEWESNGQPENNYKT
TPPVLDSDGSFFLYSKLTVDKSRWQQGNVFSCSVMHEALHNHYTQKSL
SLSPGKGGGGDYYDYDGGYYYDMD rh-eCD4-IgG2$^{I39N, mim2}$ variant (SEQ ID NO: 19): This
variant contains rhesus CD4 leader sequence,
rhesus CD4 D1D2 with I39N mutation, rhesus IgG2
hinge and Fc, tetraglycine linker; and CCR5mim2.
MNRGIPFRHLLLVLQLALLLPAVTQGKKVVLGKKGDTVELTCNASQKKN
TQFHWKNSNQIKILGNQGSFLTKGPSKLSDRADSRKSLWDQGCFSMII
KNLKIEDSDTYICEVENKKEEVELLVFGLTANSDTHLLEGQSLTLTLE
SPPGSSPSVKCRSPGGKNIQGGRTISVPQLERQDSGTWTCTVSQDQKT
VEFKIDIVVLAFQKASSTGLPCRSTCPPCPAELLGGPSVFLFPPKPKD
TLMISRTPEVTCVVVDVSQEEPDVKFNWYVDGVEVHNAQTKPREEQFN
STYRVVSVLTVTHQDWLNGKEYTCKVSNKALPAPRQKTVSKTKGQPRE
PQVYTLPPPREELTKNQVSLTCLVKGFYPSDIVVEWASNGQPENTYKT
TPPVLDSDGSYFLYSKLTVDKSRWQQGNTFSCSVMHEALHNHYTQKSL
SVSPGKGGGGDYYDYDGGYYYDMD CD4-Ig (SEG ID NO: 20):
MPMGSLQPLATLYLLGMLVASVLAKKVVLGKKGDTVELTCTASQKKSI
QFHWKNSNQIKILGNQGSFLTKGPSKLNDRADSRRSLWDQGNFPLIIK
NLKIEDSDTYICEVEDQKEEVQLLVFGLTANSDTHLLQGQSLTLTLES
PPGSSPSVQCRSPRGKNIQGGKTLSVSQLELQDSGTWTCTVLQNQKKV
```

-continued

EFKIDIVVLAAADPEPKSCDKTHTCPPCPAPELLGGPSVFLFPPKPKD

TLMISRTPEVTCVVVDVSHEDPEVKFNWYVDGVEVHNAKTKPREEQYN

STYRVVSVLTVLHQDWLNGKEYKCKVSNKALPAPIEKTISKAKGQPRE

PQVYTLPPSRDELTKNQVSLTCLVKGFYPSDIAVEWESNGQPENNYKT

TPPVLDSDGSFFLYSKLTVDKSRWQQGNVFSCSV1VfHEALHNHYTQK

SLSLSPGK

The invention thus has been disclosed broadly and illustrated in reference to representative embodiments described above. It is understood that various modifications can be made to the present invention without departing from the spirit and scope thereof.

It is further noted that all publications, patents and patent applications cited herein are hereby expressly incorporated by reference in their entirety and for all purposes as if each is individually so denoted. Definitions that are contained in text incorporated by reference are excluded to the extent that they contradict definitions in this disclosure.

---

What is claimed is:

1. A therapeutic composition comprising (a) a first polynucleotide sequence expressing a tyrosylprotein sulfotransferase (TPST), and (b) a second polynucleotide sequence expressing a fusion polypeptide comprising
   (i) a CCR5 mimetic comprising SEQ ID NO: 21 that binds a gp120 protein of a primate lentivirus,
   (ii) a CD4 polypeptide having at least 90% sequence identity to SEQ ID NO: 3 or SEQ ID NO: 4, and (iii) an immunoglobulin Fc domain; wherein the molar ratio of the first polynucleotide sequence to the second polynucleotide sequence, or the molar ratio of the TPST expressed from the first polynucleotide sequence to the fusion polypeptide expressed from the second polynucleotide sequence, is at least 1:2.

2. The therapeutic composition of claim 1, wherein the molar ratio is at least about 1:1.

3. The therapeutic composition of claim 1, wherein the first polynucleotide sequence and the second polynucleotide sequence are each present in an expression vector.

4. The therapeutic composition of claim 1, wherein the first polynucleotide sequence and the second polynucleotide sequence are both present in one expression vector.

5. The therapeutic composition of claim 3 or claim 4, wherein the expression vector is an adeno-associated virus (AAV) vector, an adenovirus vector, a retrovirus vector, a lentivirus vector, or a herpesvirus vector.

6. The therapeutic composition of claim 1, wherein the TPST is tyrosylprotein sulfotransferase 2 (TPST2) or an enzymatically active fragment thereof.

7. The therapeutic composition of claim 1, wherein the fusion polypeptide binds to a coreceptor binding site on the gp120 protein.

8. The therapeutic composition of claim 1, wherein the fusion polypeptide comprises an amino acid sequence that is at least 80% identical to a sequence selected from the group consisting of SEQ ID Nos:9-11 and 16-19.

9. The therapeutic composition of claim 8, wherein the fusion polypeptide is eCD4-Ig having an amino acid sequence shown in SEQ ID NO: 11.

10. An expression system, comprising a polynucleotide sequence that expresses a first polypeptide and a second polypeptide at a molar ratio of at least 1:2, wherein the first polypeptide is a tyrosine-protein sulfotransferase (TPST) 1 or TPST2, and the second polypeptide is a fusion protein comprising (i) a CCR5 mimetic comprising SEQ ID NO: 21 that binds a gp120 protein of a primate lentivirus, (ii) a CD4 polypeptide having at least 90% sequence identity to SEQ ID NO: 3 or SEQ ID NO: 4, and (iii) an immunoglobulin Fc domain.

11. The expression system of claim 10, further comprising one or more expression regulatory elements to control the molar ratio, wherein the regulatory elements are selected from the group consisting of an enhancer element, an intron, an internal ribosome entry site (IRES), and a woodchuck response element (WPRE).

12. A method of treating a lentiviral viral infection in a subject, comprising administering to the subject at risk of developing or suffering from the lentiviral infection a therapeutically or prophylactically effective amount of the therapeutic composition of claim 1, thereby treating the viral infection in the subject.

13. The method of claim 12, wherein the subject is a human, and the wherein the lentiviral infection is HIV- I infection.

14. The method of claim 12, wherein the TPST is TPST2, and the fusion polypeptide comprises eCD4-Ig (SEQ ID NO: 11), eCD4-Igmim 2 (SEQ ID NO: 16), eCD4-IgQ40A (SEQ ID NO: 17), or eCD4-IgQ40A,mim2 (SEQ ID NO: 18).

* * * * *

UNITED STATES PATENT AND TRADEMARK OFFICE
CERTIFICATE OF CORRECTION

PATENT NO. : 10,626,161 B2
APPLICATION NO. : 15/140919
DATED : April 21, 2020
INVENTOR(S) : Gardner et al.

Page 1 of 1

It is certified that error appears in the above-identified patent and that said Letters Patent is hereby corrected as shown below:

In the Specification

Column 1, Lines 14-19, the paragraph STATEMENT OF GOVERNMENT SUPPORT should be changed to:
-- STATEMENT OF GOVERNMENT LICENSE RIGHTS
This invention was made with government support under grant numbers AI091476, AI080324, AI100263, and RR000168 awarded by the National Institutes of Health. The government has certain rights in the invention. --

Signed and Sealed this
Sixteenth Day of June, 2020

Andrei Iancu
*Director of the United States Patent and Trademark Office*